(12) United States Patent
Budnik et al.

(10) Patent No.: US 11,719,703 B2
(45) Date of Patent: Aug. 8, 2023

(54) MASS SPECTROMETRY TECHNIQUE FOR SINGLE CELL PROTEOMICS

(71) Applicants: Northeastern University, Boston, MA (US); President and Fellows of Harvard College, Cambridge, MA (US)

(72) Inventors: Bogdan Budnik, Brookline, MA (US); Nikolai Slavov, Cambridge, MA (US); Harrison Specht, Arlington, MA (US); Ezra Levy, Boston, MA (US)

(73) Assignees: NORTHEASTERN UNIVERSITY, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 577 days.

(21) Appl. No.: 16/251,039

(22) Filed: Jan. 17, 2019

(65) Prior Publication Data

US 2019/0219592 A1    Jul. 18, 2019

Related U.S. Application Data

(60) Provisional application No. 62/725,864, filed on Aug. 31, 2018, provisional application No. 62/678,261, (Continued)

(51) Int. Cl.
*G01N 33/68* (2006.01)
*G01N 1/40* (2006.01)

(52) U.S. Cl.
CPC ....... *G01N 33/6848* (2013.01); *G01N 1/4022* (2013.01); *G01N 2440/00* (2013.01); (Continued)

(58) Field of Classification Search
CPC ............ G01N 33/6848; G01N 1/4022; G01N 2440/00; G01N 2570/00; G01N 2560/00; G01N 2458/15
See application file for complete search history.

(56) References Cited

U.S. PATENT DOCUMENTS 7,521,246 B2 * 4/2009 Yang ................. C12M 47/20
436/63
2007/0031911 A1 * 2/2007 Leite ................. G01N 33/6851
435/23
(Continued)

FOREIGN PATENT DOCUMENTS

WO    2019/232226 A1    12/2019

OTHER PUBLICATIONS

ThermoFisher (Overview of Post-Translational Modifications, ThermoFisher Scientific, 2015, see attached document) (Year: 2015).*
(Continued)

*Primary Examiner* — Benjamin R Whatley
*Assistant Examiner* — Jean Caraballo-Leon
(74) *Attorney, Agent, or Firm* — Hamilton, Brook, Smith & Reynolds, P.C.

(57) ABSTRACT

The present invention generally provides, in various embodiments, methods of analyzing samples having a low abundance of proteins, e.g., single cells, utilizing liquid chromatography and tandem mass spectroscopy (LC-MS/MS).

17 Claims, 39 Drawing Sheets
(37 of 39 Drawing Sheet(s) Filed in Color)

Related U.S. Application Data filed on May 30, 2018, provisional application No. 62/618,301, filed on Jan. 17, 2018.

(52) U.S. Cl.
CPC ..... *G01N 2458/15* (2013.01); *G01N 2560/00* (2013.01); *G01N 2570/00* (2013.01)

(56) References Cited

U.S. PATENT DOCUMENTS

| | | | |
|---|---|---|---|
| 2007/0054345 A1* | 3/2007 | Hunter | G01N 33/6851 435/23 |
| 2019/0219592 A1 | 7/2019 | Budnik et al. | |
| 2021/0080469 A1 | 3/2021 | Zhu et al. | |

OTHER PUBLICATIONS

Budnik, et al., "Mass-spectrometry of single mammalian cells quantifies proteome heterogeneiity during cell differentiation," https://web.northeastern.edu/slavovlab/Slavov-Lab-Publications/2017_Slavov_SCoPE-MS.pdf (2017).
Bendall, et al., "Single-Cell Mass Cytometry of Differential Immune and Drug Responses Across a Human Hematoppietic Continuum," Science, vol. 332, pp. 687-696, May 6, 2011.
Cohen, et al., "Dyanmic Proteomics of Individual Cancer Cells in Response to a Drug," Science, vol. 322, 1511-1516 (2008).
Darmanis, et al., "Simultaneous Multiplexed Measurement of RNA and Proteins in Single Cells," Cell Reports 14, 380-389, Jan. 12, 2016.
Franks, et al., "Post-Transciptional Regulation Across Human Tissues," PLOS Computational Biology, 13(5), e1005535, May 8, 2017.
Hicks, et al., On the Widespread and Critical Impact of Systematic Bias and Batch Effects in a Single-Cell RNA-Seq Data, bioRxiv 1, 025525, Aug. 25, 2015.
Klein, et al., Droplet Barcoding for Single Cell Transcriptomics Applied to Embryonic Stem Cells, Cell, 161(5): 1187-1201, May 21, 2015.
Landgraf, et al., "Segregation of Molecules at Cell Division Reveals Native Protein Localization," Nature Methods; 9(5): 480-482 (2012).
Li, et al., "An Integrated Platform for Isolation, Processing, and Mass Spectrometry-Based Proteomic Profiling of Rare Cells in Whole Blood," Molecular and Cellular Proteomics, 14.6, 1672-1683 (2015).
Lombard-Banek, et al., Single-Cell Mass Spectrometry for Discovery Proteomics: Quantifying Translational Cell Heterogeneity in the 16-Cell Frog (Xenopus), Angewandte Chemie International Edition, vol. 55; 2454-2458 (2016).
Milo, et al., "BioNumbers—the Database of Key Numbers in Molecular and Cell Biology," Nucleic Acids Research, vol. 38, D750-D753 (2010).
Ross, et al., Multiplexed Protein Quantitation in *Saccharomyces cerevisiae* Using Amine-reactive Isobaric Tagging Reagents, Molecular & Cellular Proteomics, 3.12; 1154-1169 (2004).
Semrau, et al., "Studying Lineage Decision-Making in Vitro: Emerging Concepts and Novel Tools," Annual Review of Cell and Development Biology, vol. 31:317-345 (2008).
Slavov, et al., "Constant Growth Rate Can Be Supported by Decreasing Energy Flux and Increasing Aerobic Glycolysis," Cell Reports 7, 705-714 (May 8, 2014).
Slavov, et al., "Correlation Signature of the Macroscopic States of the Gene Regulatory Network in Cancer," Proceedings of the National Academy of Sciences, vol. 106(11): 4079-4084 (Mar. 17, 2009).
Slavov, et al., "Differential Stoichiometry Among Core Ribosomal Proteins," Cell Reports 13, 865-873 (Nov. 3, 2015).
Virant-Klun, et al., "Identification of Maturation-Specific Proteins by Single-Cell Proteomics of Human Oocytes," Molecular & Cellular Proteomics, 15.8; 2616-2627 (2016).

Dean, et al., "Tumour Stem Cells and Drug Resistance," Nature Reviews Cancer, vol. 5, pp. 275-284 (Apr. 2005).
Savitski, et al., "Measuring and Managing Ratio Compression for Accurate iTRAQ/TMT Quantification," Journal of Proteome Researrch, vol. 12, pp. 3586-3598 (2013).
Cox, et al., "MaxQuant enables high peptide identification rates, individualized p.p.b.-range mass accuracies and proteome-wide protein quantification," Nature Biotechnology, vol. 26, No. 12, pp. 1367-1372 (Dec. 2008).
Wilhelm, et al., "Mass-spectrometry-based draft of the human proteome," Nature, vol. 509 May 29, 2014).
Yang, et al., "Deep Profiling of Cellular Heterogeneity by Emerging Single-Cell Proteomic Technologies," Proteomics 2020, 20, 1900226, 12 pages.
Aebersold, et al., "Mass-spectrometric exploration of proteome structure and function," Nature 537, 347-355. ISSN: 1476-4687. https://www.nature.com/articles/nature19949 (2018) (Sep. 2016).
Aguilar, et al., "Cycling through metabolism." EMBO molecular medicine 2, 338-348 (2010).
Bekker-Jensen, et al., "An optimized shotgun strategy for the rapid generation of comprehensive human proteomes," Cell systems 4, 587-599 (2017).
Boersema, et al. "Multiplex peptide stable isotope dimethyl labeling for quantitative proteomics." Nature protocols 4, 484-494 (2009).
Budnik, B., "Single Cell ProtEomics by Mass Spectrometry (SCoPE-MS) new technique for quantification proteomes of single mammalian cells," https://virtual.keystonesymposia.org/ks/articles/1169/view (abstract) (May 2017).
Chen, et al., "DART-ID increases single-cell proteome coverage," bioRxiv (2018).
Cooper, "The synchronization manifesto: a critique of whole-culture synchronization," Tire FEBS Journal 286, 4650-4656 (2019).
Cox, et al., "Andromeda: a peptide search engine integrated into the MaxQuant environment," Journal of proteome research 10, 1794-1805 (2011).
Cravatt, et al., "The biological impact of mass-spectrometry-based proteomics," Nature 450, 991 (2007).
Gillet, et al., "Targeted data extraction of the MS/MS spectra generated by data-independent acquisition: a new concept for consistent and accurate proteome analysis," Molecular & Cellular Proteomics 11 (2012).
Glotzer, et al., "Cyclin is degraded by the ubiquitin pathway," Nature 349, 132-138 (1991).
Haynes, et al, "DIA-SIFT: A Precursor and Product Ion Filter for Accurate Stable Isotope Data-Independent Acquisition Proteomics," Analytical Chemistry 90, 8722-8726 (2018).
Huffman, et al., "DO-MS: Data-Driven Optimization of Mass Spectrometry Methods," bioRxiv (2019).
Hughes, et al., "Single-pot, solid-phase-enhanced sample preparation for proteomics experiments," Nature Protocols, 1 (2018).
Hughes, et al., "Single-Cell Western Blotting," Nature Methods. 11(7): 749-755, Jul. 2014.
Hughes, et al., "Ultrasensitive proteome analysis using paramagnetic bead technology," Molecular systems biology 10, 757 (2014).
Kang, et al., "Quantitative Analysis of mTRAQ-Labeled Proteome Using Full MS Scans," Journal of Proteome Research 9, 3750-3758. https://doi. org/10.1021/pr9011014 (2010).
Kulak, et al., "Minimal, encapsulated proteomic—sample processing applied to copy-number estimation in eukaryotic cells," Nature methods 11, 319 (2014).
Levy, et al., "Single cell protein analysis for systems biology," Essays In Biochemistry 62 (Apr. 2018).
Li, et al., "Nanoliter-scale oil-air-droplet chip-based single cell proteomic analysis," Analytical chemistry 90, 5430-5438 (2018).
Liu, et al., "Systematic proteome and proteostasis profiling in human Trisomy 21 fibroblast cells," Nature communications 8, 1-15 (2017).
Malumbres, et al., "Cell cycle, CDKs and cancer: a changing paradigm," Nature review's cancer 9, 153-166 (2009).
Marx, "A dream of single-cell proteomics," Nature Methods 16, 809-812 (2019).

(56) References Cited

OTHER PUBLICATIONS

Mellors, et al., "Integrated microfluidic device for automated single cell analysis using electrophoretic separation and electrospray ionization mass spectrometry," Analytical chemistry 82, 967-973 (2010).
Mertins, et al., "iTRAQ labeling is superior to mTRAQ for quantitative global proteomics and phosphoproteomics," Molecular & Cellular Proteomics 11 (2012).
Minogue, et al., "Multiplexed Quantification for Data-Independent Acquisition," Analytical Chemistry 87, 2570-2575 (2015).
Muntel, et al., "Comparison of Protein Quantification in a Complex Background by DIA and TMT Workflows with Fixed Instrument Time," Journal of Proteome Research 18. PMID: 30726097, 1340-1351 (2019).
Murray, et al., "Cyclin synthesis drives the early embryonic cell cycle," Nature 339, 275-280 (1989).
Navarro, et al., "A multicenter study benchmarks software tools for label-free proteome quantification." eng. Nature Biotechnology 34, 1130-1136, ISSN: 1546-1696 (Nov. 2016).
O'Connell, et al., "Proteome-Wide Evaluation of Two Common Protein Quantification Methods," Journal of Proteome Research 17. PMID: 29635916, 1934-1942 (2018).
Rauniyar, et al., "Isobaric labeling-based relative quantification in shotgun proteomics," Journal of proteome research 13, 5293-5309 (2014).
Sinitcyn, et al., "Computational methods for understanding mass spectrometry—based shotgun proteomics data," Annual Review of Biomedical Data Science 1, 207-234 (2018),.
Slavov, et al., "Coupling among growth rate response, metabolic cycle, and cell division cycle in yeast," Molecular Biology of the Cell 22, 1997-2009 (2011).
Slavov, et al., "Metabolic cycling without cell division cycling in respiring yeast," Proceedings of the National Academy of Sciences 108, 19090-19095, ISSN: 1091-6490 (Nov. 2011).
Specht, et al., "Transformative opportunities for single-cell proteomics," Journal of Proteome Research 17, 2563-2916 (Jun. 8, 2018).
Specht, et al., "Automated sample preparation for high-throughput single-cell proteomics," bioRxiv (2019).
Tsou, et al., "DIA-Umpire: comprehensive computational framework for data-independent acquisition proteomics," Nature methods 12, 258-264 (2015).
Tyanova, et al., "The MaxQuant computational platform for mass spectrometry-based shotgun proteomics," Nature protocols 11, 2301 (2016).
Venable, et al., "Automated approach for quantitative analysis of complex peptide mixtures from tandem mass spectra," en. Nature Methods 1, 39-45, ISSN: 1548-7105. (2020) (Oct. 2004).
Zhang, et al., "Protein analysis by shotgun/bottom-up proteomics," Chemical reviews 113, 2343-2394 (2013).
Zhu, et al., "Nanodroplet processing platform for deep and quantitative proteome profiling of 10-100 mammalian cells," Nature communications 9, 882 (2018).
Ziegenhain, et al., "Comparative analysis of single-cell RNA sequencing methods," Molecular cell 65, 631-643 (2017).
Mertins, et al.. "iTRAQ Labeling is Superior to mTRAQ for Quantitative Global Proteomics and Phosphoproteomics," Mol. & Cell. Proteomics, 11.6:10.1074/mcp.Mill.014423-12 (2012).
Messner, C. B. et al.. "Ultra-fast proteomics with Scanning SWATH," Nature Biotechnology, https://doi.org/10.1038/s41587-021-00860-4 (2021).

Messner, C. B. et al., "Ultra-High-Throughput Clinical Proteomics Reveals Classifiers of COVID-19 Infection," Cell systems, 11(1): 11-24 (2020).
Minogue, et al., "Multiplexed Quantification for Data-independent Acquisition," Anal Chem., 87(5), 2570-2575 (2015).
Muntel, et al., "Comparison of Protein Quantification in a Complex Background by DIA and TMT Workflows with Fixed Instrument Time," J. Proteome Res., 18, 1340-1351, doi: 10.1021/acs.jproteome.8b00898 (2019).
Petelski, et at., "Analyzing Ribosome Remodeling in Health and Disease." Proteomics. Sep. 2020; 20(17-18): e2000039.doi:10.1002/pmic.202000039.
Pino, et al., "Improved SILAC Quantification with Data-Independent Acquisition to Investigate Bortezomib-Induced Protein Degradation," J. Proteome Res., 2021; 20(4): 1918-1927, doi: 10.1021/acs.jprotcomc.0c00938.
Rauniyar, et al., "Isobaric Labeling-Based Relative Quantification in Shotgun Proteomics," J. Proleome Res., 13, 5293-5309 (2014).
Salovska, et al., "BoxCarmax: a high-selectivity data-independent acquisition mass spectrometry method for the analysis of protein turnover and complex samples" bioRxiv preprint doi: https://doi.org/10.1101/2020.11.20.392043 (2020).
Salovska, et al., "Isoform-resolved correlation analysis between mRNA abundance regulation and protein level degradation," Molecular Systems Biology, 16: e9170 (2020).
Sinitcyn, et al., "Computational Methods for Understanding Mass Spectrometry-Based Shotgun Proteomics Data," Annu. Rev. Biomed. Data Sci., 1, 207-234 (2018).
Slavov, N., "Increasing proteomics throughput," Nature Biotech., 39:809-812 (2021).
Tsou, et al., "DIA-Umpire: comprehensive computational framework for data-independent acquisition proteomics," Nature Methods, 12(3):258-264 (2015).
Williams et al.: "Automated Coupling of Nanodroplet Sample Preparation with Liquid Chromatography-Mass Spectrometry for High-Throughput Single-Cell Proteomics", Analytical Chemistry, vol. 92, No. 15, Aug. 4, 2020 (Aug. 4, 2020), pp. 10588-10596.
Dou et al.: "High-Throughput Single Cell Proteomics Enabled by Multiplex Isobaric Labeling in a Nanodroplet Sample Preparation Platform", Analytical Chemistry, vol. 91, No. 20, Sep. 11, 2019 (Sep. 11, 2019), pp. 13119-13127.
Petelski et al.: "Multiplexed single-cell proteomics using SCoPE2", bioRxiv, Mar. 15, 2021 (Mar. 15, 2021).
Slavov: "Single-cell protein analysis by mass-spectrometry", arxiv.org, Cornell University Library, 201 Olin Library Cornell University Ithaca, NY 14853, Jun. 20, 2020 (Jun. 20, 2020).
Specht et al.: "Single-cell proteomic and transcriptomic analysis of macrophage heterogeneity using SCoPE2", Genome Biology, vol. 22, No. 1, Jan. 27, 2021 (Jan. 27, 2021).
Leduc et al.: "Exploring functional protein covariation across single cells using nPOP", bioRxiv, Mar. 30, 2022 (Mar. 30, 2022).
Leduc et al.: "Exploring functional protein covariation across single cells using nPOP", bioRxiv, Apr. 26, 2021 (Apr. 26, 2021) *This reference is being provided with Mar. 30, 2022 (Mar. 30, 2022) copy noted above.
Leduc et al.: "Droplet sample preparation for single-cell proteomics applied to the cell cycle", bioRxiv, Sep. 28, 2021 (Sep. 28, 2021).
International Search Report for International Application No. PCT/US2022/071883, consisting of 17 pages dated Jul. 15, 2022.

* cited by examiner

Experimental Design Table

| Label | Set 1 | Set 2 | Set 3 |
|---|---|---|---|
| 126 | U-937 | Jurkat | Jurkat |
| 127N | Jurkat | U-937 | Jurkat |
| 127C | U-937 | Jurkat | Jurkat |
| 128N | Jurkat | U-937 | Jurkat |
| 128C | U-937 | Jurkat | U-937 |
| 129N | Jurkat | U-937 | U-937 |
| 129C | U-937 | Jurkat | U-937 |
| *130N* | *empty* | *empty* | *empty* |
| 130C | Jurkat | U-937 | U-937 |
| 131 Carriers | 100 Jurkat 100 U-937 | 100 Jurkat 100 U-937 | 100 Jurkat 100 U-937 |

Fig. 1B

Experimental Design Table

| Label | Set 1 | Set 2 | Set 3 |
|---|---|---|---|
| 126 | Jurkat | Jurkat | Jurkat |
| 127N | U-937 | U-937 | U-937 |
| 127C | Jurkat | Jurkat | Jurkat |
| 128N | U-937 | U-937 | U-937 |
| 128C | Jurkat | Jurkat | Jurkat |
| 129N | U-937 | U-937 | U-937 |
| 129C | Jurkat | Jurkat | Jurkat |
| *130N* | *empty* | *empty* | *empty* |
| 130C | U-937 | U-937 | U-937 |
| 131 Carriers | 200 Jurkat | 200 U-937 | 200 HEK-293 |

Fig. 6A

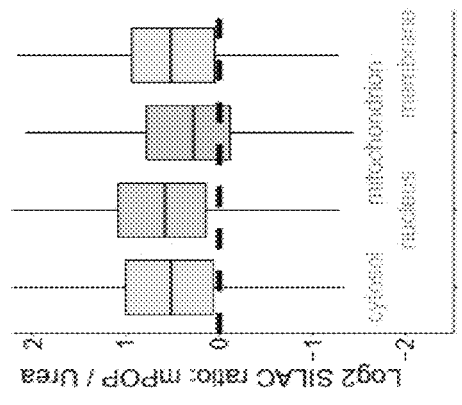
Fig. 9D
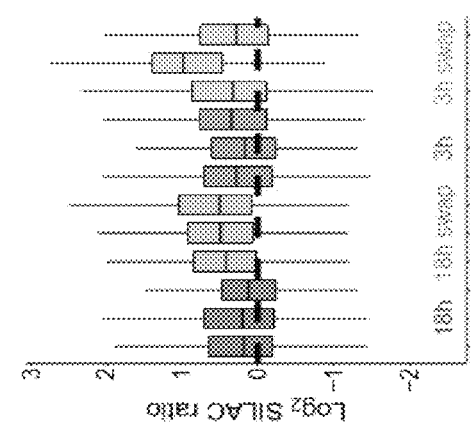
Fig. 9C
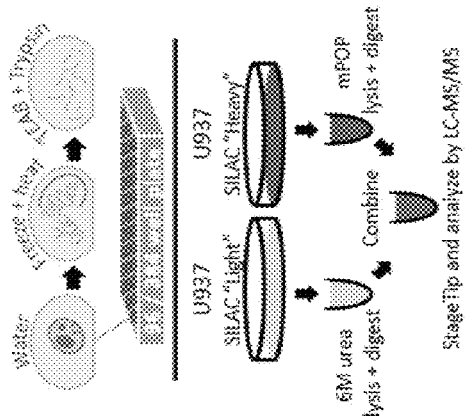
Fig. 9A
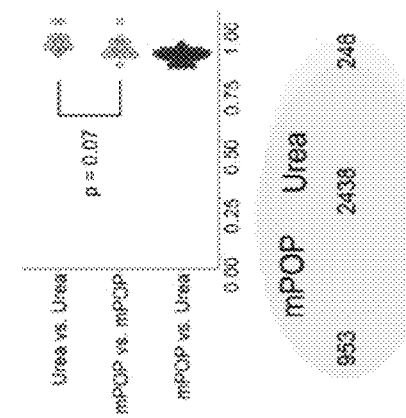
Fig. 9G
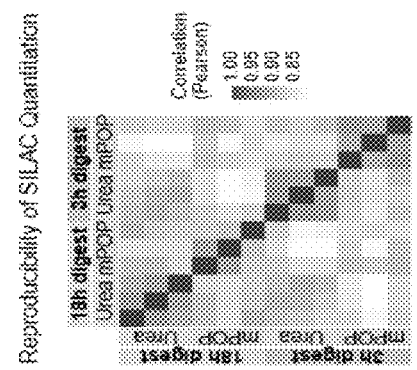
Fig. 9H
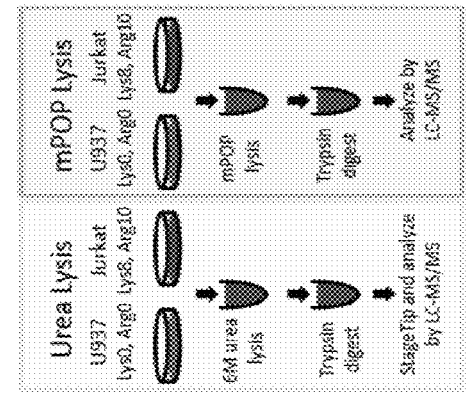
Fig. 9F
Fig. 9B
Fig. 9E

| Label (TMT tag) | 100xM set | 1xM set |
|---|---|---|
| 126 | 5,000 Jurkat cells | 50 Jurkat cells |
| 127N | 5,000 U-937 cells | 50 U-937 cells |
| 127C | empty | empty |
| 128N | empty | empty |
| 128C | 100 Jurkat cells | 1 Jurkat cell |
| 129N | 100 U-937 cells | 1 U-937 cell |
| 129C | 100 Jurkat cells | 1 Jurkat cell |
| 130N | 100 U-937 cells | 1 U-937 cell |
| 130C | 100 Jurkat cells | 1 Jurkat cell |
| 130N | 100 U-937 cells | 1 U-937 cell |
| 130C | empty | empty |

Fig. 12A

MASS SPECTROMETRY TECHNIQUE FOR SINGLE CELL PROTEOMICS

RELATED APPLICATIONS

This application claims the benefit of U.S. Provisional Application No. 62/618,301, filed on Jan. 17, 2018, U.S. Provisional Application No. 62/678,261, filed on May 30, 2018, and U.S. Provisional Application No. 62/725,864, filed on Aug. 31, 2018. The entire teachings of the above applications are incorporated herein by reference.

GOVERNMENT SUPPORT

This invention was made with government support under Grant No. 1DP2GM123497-01 awarded by the National Institutes of Health. The government has certain rights in the invention.

BACKGROUND

Cellular systems, such as tissues, cancers, and cell cultures, consist of a variety of cells with distinct molecular and functional properties. Characterizing such cellular differences is key to understanding normal physiology, combating cancer recurrence, and enhancing targeted stem cell differentiation for regenerative therapies (Dean M, Fojo T, Bates S. Tumour stem cells and drug resistance. *Nat Rev Cancer.* 2005; 5(4):275-84; Cohen A A, Geva-Zatorsky N, Eden E, Frenkel-Morgenstern M, Issaeva I, Sigal A, et al. Dynamic proteomics of individual cancer cells in response to a drug. *Science.* 2008; 322(5907):1511-6; Semrau S, van Oudenaarden A. Studying lineage decision-making in vitro: emerging concepts and novel tools. *Annu Rev Cell Dev Biol.* 2015; 31:317-45; Symmons O, Raj A. What's luck got to do with it: single cells, multiple fates, and biological nondeterminism. *Mol Cell.* 2016; 62(5):788-802; Levy E, Slavov N. Single cell protein analysis for systems biology. *Essays Biochem.* 2018; 62).

SUMMARY

The present invention provides methods for analyzing peptides in samples with a low abundance of proteins, e.g., single cell samples, utilizing mass spectroscopy, e.g., tandem mass spectroscopy.

In various aspects, the invention provides methods of analyzing a test peptide in a test sample, the methods comprising: mixing labeled test peptides from the test sample, the sample having a low abundance of proteins, with labeled carrier peptides from a sample having a high abundance of proteins to form a mixture, wherein the labeled test peptides and the labeled carrier peptides have different labels; and performing liquid chromatography and tandem mass spectroscopy (LC-MS/MS) on the mixture to obtain an analysis of the labeled test peptides.

In particular embodiments, the test sample having a low abundance of proteins is from a single cell.

In some embodiments, the sample having a high abundance of proteins is obtained from the same type of cell as the test sample having a low abundance of proteins. In further embodiments, the sample having a high abundance of proteins is obtained from a plurality of cells, such as e.g., about 10 cells or greater, about 20 cells or greater, about 30 cells or greater, about 40 cells or greater, about 50 cells or greater, about 100 cells or greater, about 200 cells or greater, or about 300 cells or greater.

In some embodiments, the analysis of the labeled test peptides can comprise obtaining a relative quantification of labeled test peptides. In some embodiments, the analysis of the labeled test peptides can comprise sequencing the labeled test peptides.

In another aspect, the invention provides methods of analyzing a post-translationally modified peptide in a test sample, the methods comprising: mixing labeled test peptides from the test sample, the sample having a low abundance of proteins, with labeled carrier peptides from a sample having a high abundance of post-translationally modified proteins to form a mixture, wherein the labeled test peptides and the labeled carrier peptides have different labels; and performing LC-MS/MS on the mixture to obtain an analysis of the labeled test peptides.

In one embodiment, the sample having a high abundance of post-translationally modified proteins is enriched for post-translationally modified proteins. In some embodiments, the post-translationally modified proteins are enriched by antibody-based selection for post-translationally modified proteins. In some embodiments, the post-translationally modified proteins are enriched by chemically-based selection for post-translationally modified proteins.

In particular embodiments, the test sample having a low abundance of post-translationally modified proteins is from a single cell.

In some embodiments, the sample having a high abundance of post-translationally modified proteins is obtained from the same type of cell as the test sample having a low abundance of proteins. In further embodiments, the sample having a high abundance of post-translationally modified proteins is obtained from a plurality of cells, such as, e.g., about 10 cells or greater, about 20 cells or greater, about 30 cells or greater, about 40 cells or greater, about 50 cells or greater, about 100 cells or greater, about 200 cells or greater, or about 300 cells or greater.

In some embodiments, the analysis of the labeled test peptides can comprise obtaining a relative quantification of labeled test peptides having a post-translational modification. In some embodiments, the analysis of the labeled test peptides can comprise sequencing the labeled test peptides having a post-translation modification.

In certain embodiments, the post-translational modification is selected from the group consisting of phosphorylation, acetylation, ubiquitination, O-glycosylation, N-glycosylation, methylation, sumoylation and combinations thereof.

In embodiments of the various aspects provided herein, the test peptide from the test sample having a low abundance of proteins can be obtained by: freezing the test sample to about −80 degrees Celsius and then heating the test sample to about 90 degrees Celsius to obtain a lysate; digesting the lysate to obtain digested test peptides; and labeling the digested test peptides to obtain labeled test peptides.

In another aspect, the present invention provides methods of lysing a cell sample, e.g., a single cell, for protein extraction, comprising:
  freezing the cell sample to about −80 degrees Celsius; and
  heating the cell sample after freezing to about 90 degrees Celsius to obtain a lysate for protein extraction.

In some embodiments, the methods of lysing a cell sample can further comprise digesting the lysate to obtain peptides. In some embodiments, the methods further comprise labeling the peptides to obtain labeled peptides.

BRIEF DESCRIPTION OF THE DRAWINGS

The foregoing will be apparent from the following more particular description of example embodiments, as illustrated in the accompanying drawings.

The patent or application file contains at least one drawing executed in color. Copies of this patent or patent application publication with color drawings will be provided by the Office upon request and payment of the necessary fee.

FIGS. 1A-1E show example experimental data validating SCoPE-MS by classifying single cancer cells based on their proteomes. FIG. 1A shows a conceptual diagram and work flow of SCoPE-MS. Individually picked live cells are lysed by sonication, the proteins in the lysates are digested with trypsin, and the resulting peptides are labeled with TMT™ labels, and combined and analyzed by LC-MS/MS (Orbitrap Elite). FIG. 1B shows the design of control experiments used to test the ability of SCoPE-MS to distinguish U-937 cells from Jurkat cells. Each set was prepared and quantified on a different day to evaluate day-to-day batch artifacts. FIG. 1C shows unsupervised principal component (PC) analysis using data for quantified proteins from the experiments described in FIG. 1B stratifies the proteomes of single cancer cells by cell type. Protein levels from six bulk samples from Jurkat and U-937 cells are also projected and marked with filled semitransparent circles. The two largest PCs explain over 50% of the variance. Similar separation of Jurkat and U-937 cells is observed when different carrier cells are used (see FIGS. 6A-6C). FIG. 1D shows distributions of protein levels across single U-937 and Jurkat cells indicate cell-type-specific protein abundances. FIG. 1E shows results of adenocarcinoma cells (MDA-MB-231) expressing mCherry and LifeAct-iRFP670 sorted by Aria FACS into a 96-well plate, one cell per well. The relative levels of mCherry and iRFP were estimated by the sorter (from their florescence intensity) and by SCoPE-MS, and the two estimates compared by their Spearman correlations ($\rho$).

FIG. 2A shows clustergrams of pairwise protein-protein correlations in cells differentiating for 3, 5, and 8 days after LIF withdrawal. The correlation vectors were hierarchically clustered based on the cosine of the angles between them. All single-cell sets used the same carrier channel which was comprised of cells mixed from different time points. FIG. 2B shows the similarity between the correlation matrices shown in FIG. 2A is quantified by the distribution of correlations between corresponding correlation vectors, as previously described (Slavov N, Dawson K A. Correlation signature of the macroscopic states of the gene regulatory network in cancer. *Proc Natl Acad Sci*. 2009; 106(11):4079-84). Medians are marked with green squares and means with red pluses. FIG. 2C shows all pairwise Pearson correlations between ribosomal proteins (RPs) were computed by averaging across cells. The correlation matrix was clustered, using the cosine between the correlation vectors as a similar measure. In FIG. 2D, to evaluate the similarity in the relative levels of functionally related proteins, Pearson correlations within sets of functionally related proteins as defined by the gene ontology (GO) were computed. These sets included protein complexes, lineage-specific proteins, and proteins functioning in cell growth and division. The distribution of correlations for all quantified proteins is also displayed and used as a null distribution. To remove a positive bias from the null distribution, the contribution of the first pair of singular vectors was subtracted from the matrix of protein levels since this pair often concentrates global effects, which include batch effects and other system-wide trends (Slavov N, Dawson K A. Correlation signature of the macroscopic states of the gene regulatory network in cancer. *Proc Natl Acad Sci*. 2009; 106(11):4079-84; Plerou V, Gopikrishnan P, Rosenow B, Amaral L A N, Guhr T, Stanley H E. Random matrix approach to cross correlations in financial data. *Phys Rev E*. 2002; 65(6):066126). The difference between the distributions of correlations for the protein clusters and the null distribution is present in the raw data before this normalization.

FIG. 3A illustrates distributions of protein abundances for all proteins quantified from $10^7$ differentiating ES cells (van den Berg P R, Budnik B, Slavov N, Semrau S. Dynamic post-transcriptional regulation during embryonic stem cell differentiation. *bioRxiv*. 2017; 1) or in at least one single-cell SCoPE-MS set at FDR 1%. The probability of quantifying a protein by SCoPE-MS is close to 100% for the most abundant proteins quantified in bulk samples and decreases with protein abundance, for a total of 1526 quantified proteins. FIG. 3B shows the proteomes of all single EB cells were projected onto their PCs, and the marker of each cell color-coded by day. The single-cell proteomes cluster partially based on the days of differentiation. FIG. 3C shows a tabular display of the variance explained by the principal components and their correlations to the days of differentiation and the missing data points for each cell. FIGS. 3D and 3E show the proteomes of cells differentiating for 8 days were projected onto their PCs, and the marker of each cell color-coded based on the normalized levels of all proteins from the indicated gene-ontology groups.

FIG. 4A shows a clustergram of pairwise correlations between mRNAs with 2.5 or more reads per cell as quantified by inDrop in single EB cells (Klein A M, Mazutis L, Akartuna I, Tallapragada N, Veres A, Li V, et al. Droplet barcoding for single-cell transcriptomics applied to embryonic stem cells. *Cell*. 2015; 161(5):1187-201.) FIG. 4B shows a clustergram of pairwise correlations between proteins quantified by SCoPE-MS in 12 or more single EB cells. FIG. 4C illustrates the overlap between corresponding RNA from FIG. 4A and protein clusters from FIG. 4B indicates similar clustering patterns. FIG. 4D illustrates protein-protein correlations correlate to their corresponding mRNA-mRNA correlations. Only genes with significant mRNA-mRNA correlations were used for this analysis. FIG. 4E illustrates the concordance between corresponding mRNA and protein correlations (computed as the correlation between corresponding correlations (Slavov N, Dawson K A. Correlation signature of the macroscopic states of the gene regulatory network in cancer. *Proc Natl Acad Sci*. 2009; 106(11):4079-84)) is high for ribosomal proteins (RPL and RPS) and lower for developmental genes; distribution medians are marked with red pluses. Only the subset of genes quantified at both RNA and protein levels were used for all panels FIGS. 5A-5D provide analysis of the contribution of background noise to quantification of peptides in single cells.

FIGS. 6A-6C provides example results showing that relative quantification is independent from the carrier channel. FIG. 6A shows the design of control experiments used to test the ability of SCoPE-MS to distinguish U-937 cells from Jurkat cells independently from the cells in the carrier channel. The carrier channel in each SCoPE-MS set contained 200 cells: 200 Jurkat cells in set 1, 200 U-937 cells in set 2, and 200 HEK-293 cells in set 3. FIG. 6B illustrates unsupervised principal component (PC) analysis using data for quantified proteins from the experiments described in FIG. 6A stratifies the proteomes of single cancer cells by cell type regardless of the type of cells used in the carrier channel. FIG. 6C. To explore the extent to which peptides from the carrier channel might affect relative quantification in the single-cell channels, the pairwise correlations between the relative peptide levels of a SCoPEMS set were computed. Relative peptide levels were computed by first normalizing the RI intensities in each channel to a median of 1 (to correct for different amount of total protein, especially in the carrier channel) and then by dividing the vector of RI intensities for each peptide by its mean, to remove the large differences in abundances between different peptides. The correlations between these relative estimates indicate that Jurkat cells correlate positively to Jurkat cells and negatively to U-937 cells. The converse holds for U-937 cells. Importantly, the carrier channel correlates negatively with most single cells, except for a weak correlation with one U-937 cell, perhaps reflecting slightly high contribution of U-937 cells to the carrier channel.

FIG. 7A illustrates a comparison between protein levels estimates from bulk samples and from single cells. The single-cell protein estimates are the average from 12 Jurkat cells from the experiments described in FIG. 1B and equal as the summed-up precursor ion areas apportioned by RI intensities. FIG. 7B illustrates a comparison between relative protein levels (fold changes) estimated from bulk samples and from single cells. The single-cell protein estimates are the ratio between average levels summed across 12 Jurkat cells over the average level summed across 12 U-937 cells. Proteins whose bulk estimates did not change between Jurkat and U-937 cells (fold change less than 10%) were omitted from the plot. FIG. 7C illustrates a correlation matrix of all pairwise Pearson correlations among the ratios of peptide abundances in U-937 and in Jurkat cells from Set 2 in FIG. 1B. The superscripts correspond to the TMT™ labels ordered by mass, with 1 being 126, 2 being 127N and so on. The positive correlations among estimates from different combinations of TMT™ channels suggest good consistency of relative quantification. FIG. 7D illustrates distributions of correlations between technical replicates of peptide ratios measured in two halves of the same single-cell set; each measurement estimated the peptide ratios from peptides corresponding to ½ cell. The first distribution corresponds to correlations from across all measured peptides. The other distributions correspond to the correlations computed from the subset of peptides having coefficient of variation (CV) above the indicated percentile, i.e., peptides with larger fold changes. The red crosses mark the distribution medians. Correlations were computed with log transformed protein levels and ratios.

FIG. 8A illustrates the peptides from a few SCoPE-MS sets from FIGS. 1A-1E and FIGS. 7A-7D rank sorted by the confidence of their identification as quantified by the posterior error probability (PEP). The rank sorted PEPs for each set are color-coded based on the number of quantified peptides at PEP<0:03, excluding peptides from contaminant proteins. The results exemplify the variability in the number of peptides quantified in different SCoPE-MS sets. For some sets, relaxing the false discovery rate (FDR) to 3% increases significantly the number of quantified peptides while keeping false positives below 3%. FIG. 8B illustrates that protein ratios derived from peptides having PEP 2 (0:01; 0:03] correlate positively with the corresponding protein ratios derived from peptides having PEP<0:01, thus indicating that peptides identified with lower confidence carry quantitative information. FIG. 8C illustrates the protein ratios derived from two non-overlapping subsets of peptides having PEP<0:01. The correlation for peptides identified with lower confidence FIG. 8B is lower than for those identified with high confidence FIG. 8C. This might be due in part to the fact that factors reducing the confidence of identification, such as lower abundance or higher co-isolation, are also likely to affect quantification.

FIGS. 9A-9H show example experimental data validating mPOP cell lysis by comparison to urea lysis using SILAC labeling. FIG. 9A shows a conceptual diagram of a high-throughput mPOP workflow: cells are lysed by a freeze-heat cycle (−80° C. to 90° C.), pH adjusted by triethylammonium bicarbonate (TEAB) and enzymatically digested to peptides. FIG. 9B shows a schematic of experiments comparing lysis yield: Cells were sorted by FACS, lysed by either mPOP or 6M urea, and the proteins digested to peptides by trypsin. Lysates were combined, cleaned from urea by StageTip, concentrated, and analyzed by LC-MS/MS. FIG. 9C. Lysis by mPOP compared to 6M urea across 12 replicates, including SILAC label swaps and two digestion conditions, 3 hours and 18 hours. Lysis efficiency was quantified by the distribution of mPOP/Urea peptide SILAC ratios, with equivalent lysis and digestion displayed with the dotted line at zero. FIG. 9D. SILAC ratios from FIG. 9C grouped by cellular compartment indicate that mPOP efficiently extracts proteins from all compartments. FIG. 9E. Schematic of comparing quantification by in cells lysed by urea or mPOP. Cells were sorted by FACS into tubes to contain 10,000 "heavy" Jurkat cells and "light" U-937 cells, lysed by either mPOP or 6M urea, the proteins digested to peptides by trypsin, urea removed by StageTip clean-up if necessary, concentrated, and analyzed by LC-MS/MS. FIG. 9F. Correlation matrix of all biological replicates produced from the experiment described in FIG. 9D including two digestion conditions: 3 hours and 18 hours. FIG. 9G. Correlations from FIG. 9E displayed as distributions. Differences between mPOP and urea are insignificant, pvalue=0.07, based on Kolmogorov-Smirnov test. FIG. 9H. Proteins identified and quantified by mPOP and urea lysis overlap significantly, but mPOP identified 953 proteins not identified in the urea lysates.

FIG. 10A. FACS sorted Jurkat and U-937 cells were lysed with mPOP, and a 1×M SCoPE-MS set was prepared as described in FIG. 12A. Direct injections of 1×M SCoPE-MS set on a commercial Waters column resulted in reproducible and rich spectra. The y-axes of all panels range from 0 to $3 \times 10^8$. FIG. 10B. Proteome coverage increases with the number of quantified cells. All identifications are based on spectra only, not using retention times. FIG. 10C. The reporter ion (RI) signal in single-cell channels is much larger than in the empty channels. FIG. 10D. mPOP and SCoPE-MS allow for pure MS2 spectra. FIG. 10E. Relative peptide levels estimated from single-cell SCoPE-MS channels are very similar to the corresponding estimates from the carrier (bulk) channels. FIG. 10F. Principal component analysis separates perfectly single-cell and carrier channels dependent on whether they correspond to Jurkat or to U-937 cells. All quantified proteins were used for this analysis and each protein was normalized separately to a mean level of one for the carrier channels and the single-cell channels. Without this normalization, PC2 separated the carrier from the single-cell channels (see FIG. 12B).

FIG. 11A. Experimental design for high-throughput, low-input proteomics with mPOP combined with SCoPE-MS. Single cells are sorted into 96-well plates and used for SCoPE-MS sets. While these sets can include up to nine single cells/set, the data shown in FIGS. 11B and 11C used seven and six single cells/set respectively, because some TMT™ channels were used for controls; see Materials and Methods. FIG. 11B. A principal component analysis (PCA) of single HEK-293 and U-937 cells. The cells were sorted by FACS in a 96-well plate, one cell per well, and processed by mPOP and SCoPE-MS. The first principal component (PC1) separates the projected single-cell proteomes by cell type. FIG. 11C. Mouse embryonic stem cells expressing the FUCCI system (Sladitschek, H. L. & Neveu, P. A. MXS-chaining: a highly efficient cloning platform for imaging and flow cytometry approaches in mammalian systems. *PloS one* 10, e0124958 (2015)) were sorted by Aria FACS into a 96-well plate, one cell per well, from two distinct phases of the cell division cycle. The phases were inferred from the fluorescent protein Citrine, fused to partial sequences of Geminin that is a ubiquitin-target of the anaphase promoting complex. FIG. 11D. The proteins with the largest variance separate the single cells by cell cycle phase.

FIGS. 12A-12B show example design and quantification of 100×M SCoPE-MS sets. FIG. 12A. Schematic for the design of 100×M sets and the proteome amounts corresponding to 1×M sets. FIG. 12B. PCA of 1×M sets without normalization of the carrier and the single-cell channels.

DETAILED DESCRIPTION

Figure 1A:
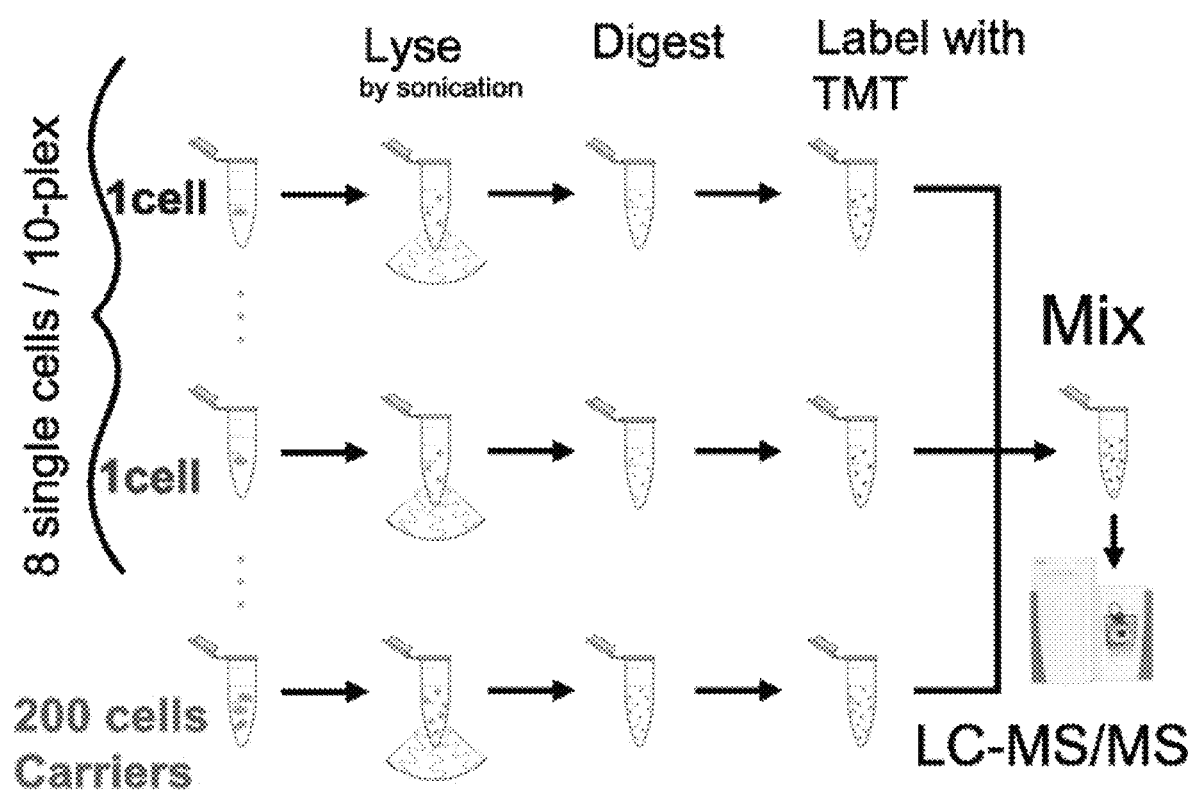
Figure 1C:
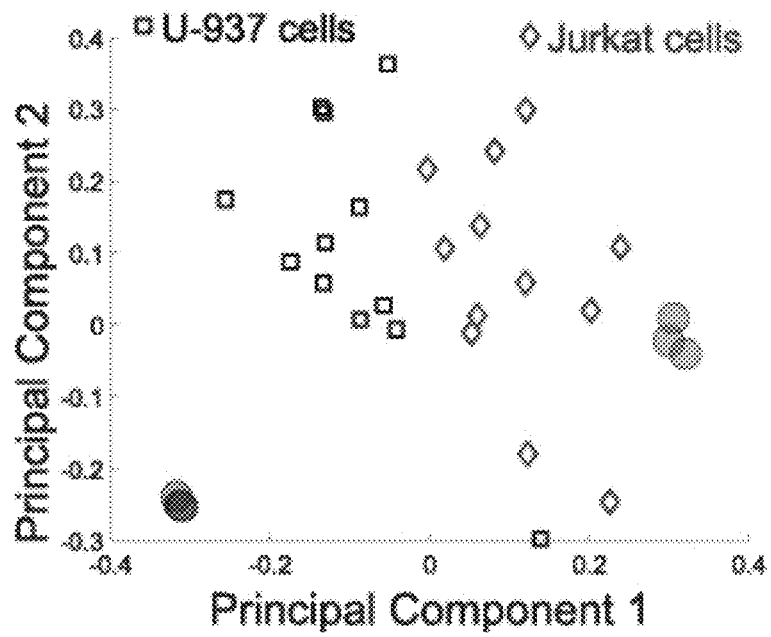
Figure 1D:
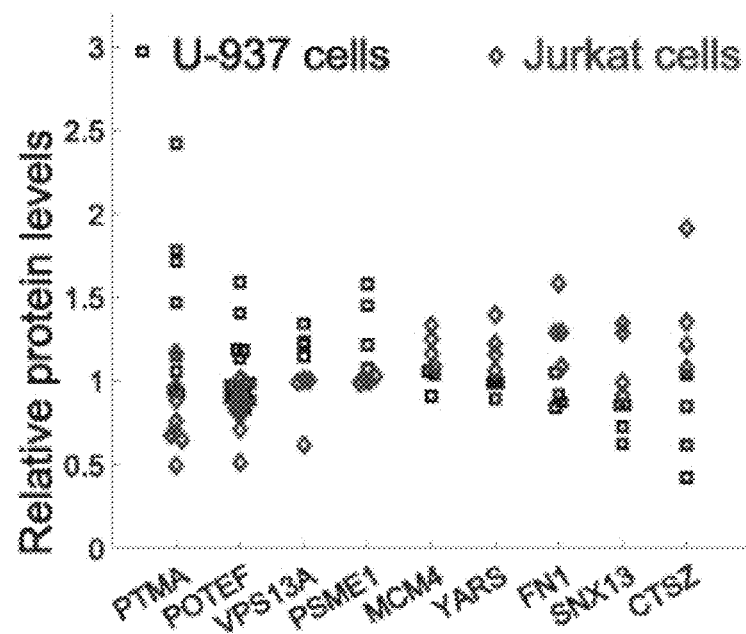

A description of example embodiments follows.

Unless defined otherwise, all technical and scientific terms used herein have the same meaning as commonly understood by one of ordinary skill in the art to which this invention pertains.

It should be noted that throughout this specification the terms "comprising" and "having" are used to denote that embodiments of the invention "comprise" the noted features and as such, may also include other features. However, in the context of this invention, the terms "comprising" and "having" may also encompass embodiments in which the invention "consists essentially of" the relevant features or "consists of" the relevant features.

There is a need for better methods of quantifying proteins in single mammalian cells, as current methods have remained confined to fluorescent imaging and antibodies. Fluorescent proteins have proved tremendously useful but are limited to quantifying only a few proteins per cell and sometimes introduce artifacts (Levy E, Slavov N. Single cell protein analysis for systems biology. *Essays Biochem.* 2018; 62; Landgraf D, Okumus B, Chien P, Baker T A, Paulsson J. Segregation of molecules at cell division reveals native protein localization. *Nat Methods.* 2012; 9(5):480-2). Multiple antibody-based methods for quantifying proteins in single cells have been recently developed, including CyTOF (Bandura D R, Baranov V I, Ornatsky O I, Antonov A, Kinach R, Lou X, et al. Mass cytometry: technique for real time single cell multitarget immunoassay based on inductively coupled plasma time-of-flight mass spectrometry. *Anal Chem.* 2009; 81(16):6813-22; Bendall S C, Simonds E F, Qiu P, El-ad D A, Krutzik P O, Finck R, et al. Single-cell mass cytometry of differential immune and drug responses across a human hematopoietic continuum. *Science.* 2011; 332(6030):687-96), single-cell Western blots (Hughes A J, Spelke D P, Xu Z, Kang C C, Schaffer D V, Herr A E. Single-cell western blotting. *Nat Methods.* 2014; 11(7):749-55), and Proseek Multiplex, an immunoassay readout by PCR (Darmanis S, Gallant C J, Marinescu V D, Niklasson M, Segerman A, Flamourakis G, et al. Simultaneous multiplexed measurement of RNA and proteins in single cells. *Cell Rep.* 2016; 14(2):380-9). These methods can quantify up to a few dozen endogenous proteins recognized by highly specific cognate antibodies and have enabled exciting research avenues (Levy E, Slavov N. Single cell protein analysis for systems biology. *Essays Biochem.* 2018; 62). Still, the throughput and accuracy of antibody-based methods are limited by cellular permeability, molecular crowding, epitope accessibility, and the availability of highly specific antibodies that bind their cognate proteins stoichiometrically (Levy E, Slavov N. Single cell protein analysis for systems biology. *Essays Biochem.* 2018; 62; Marcon E, Jain H, Bhattacharya A, Guo H, Phanse S, Pu S, et al. Assessment of a method to characterize antibody selectivity and specificity for use in immunoprecipitation. *Nat Methods.* 2015; 12(8):725).

The present invention provides methods for analyzing peptides in samples with a low abundance of proteins, e.g., single cell samples. Some biological questions require quantifying thousands of proteins in single cells; however, there is very little abundance of some proteins, often making analyses difficult. To achieve the goal of allowing analysis of low abundance proteins in samples, e.g., single cells, Applicants developed Single Cell ProtEomics by Mass Spectrometry (SCoPE-MS) and have also validated its ability to identify distinct human cancer cell types based on their proteomes. (see Budnik, B., Levy, E., Harmange, G. and Slavov, N. SCoPE-MS: mass spectrometry of single mammalian cells quantifies proteome heterogeneity during cell differentiation. *Genome Biology.* 2018; 19:161; incorporated herein by reference in its entirety). Further, SCoPE-MS has been further validated by being utilized to quantify over a thousand proteins in differentiating mouse embryonic stem cells. The single-cell proteomes enable one to deconstruct cell populations and infer protein abundance relationships. Comparison between single-cell proteomes and transcriptomes indicates coordinated mRNA and protein covariation, yet many genes exhibit functionally concerted and distinct regulatory patterns at the mRNA and the protein level. The present invention can also be applied to any cell type that one wishes to perform a proteomic analysis.

Tandem mass spectrometry, also referred to herein as MS/MS or MS2, involves multiple steps of mass spectrometry selection, with some form of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other processes known to those skilled in the art. The resulting ions are then separated and detected in a second stage of mass spectrometry (MS2). A common use is for analysis of proteins and peptides.

Quantitative proteomics is used to determine the relative or absolute amount of proteins in a sample. Several quantitative proteomics methods are based on MS/MS. One method commonly used for quantitative proteomics is isobaric tag labeling. Isobaric tag labeling enables simultaneous identification and quantification of proteins from multiple samples in a single analysis. To quantify proteins, peptides are labeled with chemical tags that have the same structure and nominal mass, but vary in the distribution of heavy isotopes in their structure. These tags, commonly referred to as tandem mass tags (TMT™), are designed so that the mass tag is cleaved at a specific linker region upon higher-energy collisional-induced dissociation during tandem mass spectrometry, yielding reporter ions of different masses. Protein quantitation is accomplished by comparing the intensities of the reporter ions in the MS/MS spectra. Two commercially available isobaric tags are iTRAQ® and TMT™ reagents.

In isobaric labeling for tandem mass spectrometry, proteins are extracted from cells, digested, and labeled with tags of the same mass. When fragmented during MS/MS, the reporter ions show the relative amount of the peptides in the samples.

An isobaric tag for relative and absolute quantitation (iTRAQ®) is a reagent for tandem mass spectrometry that is used to determine the amount of proteins from different sources in a single experiment. iTRAQ® uses stable isotope labeled molecules that can form a covalent bond with the N-terminus and side chain amines of proteins. The iTRAQ® reagents are used to label peptides from different samples that are pooled and analyzed by liquid chromatography and tandem mass spectrometry. The fragmentation of the attached tag generates a low molecular mass reporter ion that can be used to relatively quantify the peptides and the proteins from which they originated.

A tandem mass tag (TMT™) is an isobaric mass tag chemical label used for protein quantification and identification. The tags contain four regions: mass reporter, cleavable linker, mass normalization, and protein reactive group. TMT™ reagents can be used to simultaneously analyze 2 to 11 different peptide samples prepared from cells, tissues or biological fluids. Three types of TMT™ reagents are available with different chemical reactivities: (1) a reactive NHS ester functional group for labeling primary amines (TMT-duplex™, TMT™ sixplex™, TMT10plex plus™, TMT11-131C™), (2) a reactive iodoacetyl functional group for labeling free sulfhydryls (iodoTMT™) and (3) reactive alkoxyamine functional group for labeling of carbonyls (aminoxyTMT™).

MS/MS can also be used for protein sequencing, as is understood by those skilled in the art. When intact proteins are introduced to a mass analyzer, it is called "top-down proteomics," and when proteins are digested into smaller peptides and subsequently introduced into the mass spectrometer, it is called "bottom-up proteomics". Shotgun proteomics is a variant of bottom up proteomics in which proteins in a mixture are digested prior to separation and tandem mass spectrometry.

The application of liquid chromatography (LC) and MS/MS (referred to herein as "LC-MS/MS") to bulk samples comprised of many cells allows for the confident identification and quantification of thousands of proteins (Aebersold R, Mann M. Mass spectrometry-based proteomics. *Nature.* 2003; 422(6928):198-207; De Godoy L M, Olsen J V, Cox J, Nielsen M L, Hubner N C, Fröhlich F, et al. Comprehensive mass-spectrometry-based proteome quantification of haploid versus diploid yeast. *Nature.* 2008; 455(7217):1251; Cox J, Mann M. MaxQuant enables high peptide identification rates, individualized ppb range mass accuracies and proteome-wide protein quantification. *Nat Biotechnol.* 2008; 26(12):1367-72; Slavov N, Budnik B, Schwab D, Airoldi E, van Oudenaarden A. Constant growth rate can be supported by decreasing energy flux and increasing aerobic glycolysis. *Cell Rep.* 2014; 7:705-14; Wilhelm M, Schlegl J, Hahne H, Gholami A, Lieberenz M, et al. Mass-spectrometry-based draft of the human proteome. *Nature.* 2014; 509:582-7; van den Berg P R, Budnik B, Slavov N, Semrau S. Dynamic post-transcriptional regulation during embryonic stem cell differentiation. *bioRxiv.* 2017; 1; Nesvizhskii A I. Proteogenomics: concepts, applications and computational strategies. *Nat Methods.* 2014; 11(11):1114).

The present invention utilizes the utility of LC-MS/MS and applies new methodology to single mammalian cells. Most proteins are present at over 50,000 copies per cell (Milo R, Jorgensen P, Moran U, Weber G, Springer M. BioNumbers—the database of key numbers in molecular and cell biology. *Nucleic Acids Res.* 2010; 38: D750-3; Schwanhausser B, Busse D, Li N, Dittmar G, Schuchhardt J, Wolf J, et al. Corrigendum: global quantification of mammalian gene expression control. *Nature.* 2013; 495: 126127) while modern mass spectrometry instruments have sensitivity to identify and quantify ions present at hundreds of copies (Zubarev R A, Makarov A. Orbitrap mass spectrometry. *Anal Chem.* 2013; 85(11):5288-96; Specht H, Slavov N. Transformative opportunities for single-cell proteomics. *J Proteome Res.* 2018; 17: 2565-2571). Thus, the methods described herein attempt to deliver enough of the protein copies from a single cell as ions for MS/MS analysis such that they may be quantified accurately (Specht H, Slavov N. Transformative opportunities for single-cell proteomics. *J Proteome Res.* 2018; 17:2565-2571). The article, Transformative opportunities for single-cell proteomics. *J Proteome Res.* 2018; 17:2565-2571, is incorporated herein by reference in its entirety.

To this end, in various aspects, the invention provides methods of analyzing a test peptide in a test sample, the methods comprising: mixing labeled test peptides from the test sample, the sample having a low abundance of proteins, with labeled carrier peptides from a sample having a high abundance of proteins to form a mixture, wherein the labeled test peptides and the labeled carrier peptides have different labels; and performing LC-MS/MS on the mixture to obtain an analysis of the labeled test peptides. In some embodiments, the methods can be applied to multiple test peptides and/or multiple test samples. In such embodiments, the test peptides in a test sample receive a unique label from the other test peptides in other test samples to allow one to distinguish from which test sample each of the test peptides originates. In the various embodiments described herein, isobaric tags, such as e.g., iTRAQ® and TMT™, may be utilized.

As used herein, the phrase "low abundance of proteins" refers to a protein level that is below the level that is readily detectable by current prior art methods of tandem mass spectrometry. As used herein, the phrase "high abundance of proteins" refers to a protein level that is readily detectable by current prior art methods of tandem mass spectrometry. In some embodiments, a "high abundance of proteins" may be artificially created, or "spiked," by enriching for a specific protein or proteins that one wishes to analyze by the methods described herein.

In particular embodiments, the test sample having a low abundance of proteins is from a single cell. In some embodiments, the test sample having a low abundance of proteins can be from a population of cells that have an overall low abundance of proteins to be analyzed.

Most protocols for bulk LC-MS/MS begin by lysing the cells with detergents or urea (Dhabaria A, Cifani P, Reed C, Steen H, Kentsis A. A high-efficiency cellular extraction system for biological proteomics. *J Proteome Res.* 2015; 14(8):3403-8). Since these chemicals are incompatible with MS, they must be removed by cleanup procedures. These cleanup procedures can result in substantial losses of protein, and colleagues have developed advanced methods, such as SP3 (Hughes C S, Foehr S, Garfield D A, Furlong E E, Steinmetz L M, Krijgsveld J. Ultrasensitive proteome analysis using paramagnetic bead technology. *Mol Syst Biol.* 2014; 10(10):757) and iST (Kulak N A, Pichler G, Paron I, Nagaraj N, Mann M. Minimal, encapsulated proteomic sample processing applied to copy-number estimation in eukaryotic cells. *Nat Methods.* 2014; 11(3):319), that minimize cleanup losses and allow for quantifying thousands of proteins from samples having just a few micrograms of total protein (Dhabaria A, Cifani P, Reed C, Steen H, Kentsis A. A high-efficiency cellular extraction system for biological proteomics. *J Proteome Res.* 2015; 14(8):3403-8; Sielaff M, Kuharev J, Bohn T, Hahlbrock J, Bopp T, Tenzer S, et al. Evaluation of FASP, SP3, and iST protocols for proteomic sample preparation in the low microgram range. *J Proteome Res.* 2017; 16(11):4060-72). Indeed, the SP3 method has been successfully used for purifying and quantifying proteins from single human oocytes (~100 µm diameter) (Virant-Klun I, Leicht S, Hughes C, Krijgsveld J. Identification of maturation-specific proteins by single-cell proteomics of human oocytes. *Mol Cell Proteomics.* 2016; 15(8):2616-27). Still, most mammalian cells are smaller (10-15 µm diameter) (Milo R, Jorgensen P, Moran U, Weber G, Springer M. BioNumbers—the database of key numbers in molecular and cell biology. *Nucleic Acids Res.* 2010; 38:D750-3), and one may not be able to confidently clean up their cell lysates (having about 500 pg of total protein) without incurring large protein losses. Thus, Applicants sought to obviate cleanup (and therefore eliminate cleanup-related losses) by replacing chemical lysis with mechanical lysis by focused acoustic sonication (Dhabaria A, Cifani P, Reed C, Steen H, Kentsis A. A high-efficiency cellular extraction system for biological proteomics. *J Proteome Res.* 2015; 14(8):3403-8; Li S, Plouffe B D, Belov A M, Ray S, Wang X, Murthy S K, et al. An integrated platform for isolation, processing, and mass spectrometry-based proteomic profiling of rare cells in whole blood. *Mol Cell Proteomics.* 2015; 14(6):1672-83).

Before being ionized and sent for MS analysis, peptides must be separated (Aebersold R, Mann M. Mass spectrometry-based proteomics. *Nature.* 2003; 422(6928):198-207; Slavov N, Budnik B, Schwab D, Airoldi E, van Oudenaarden A. Constant growth rate can be supported by decreasing energy flux and increasing aerobic glycolysis. *Cell Rep.* 2014; 7:705-14; Wilhelm M, Schlegl J, Hahne H, Gholami A, Lieberenz M, et al. Mass-spectrometry-based draft of the human proteome. *Nature.* 2014; 509:582-7). The separation for bulk samples is usually accomplished by nanoliquid chromatography (nLC). To reduce losses due to proteins adhering to the large surface area of nLC columns, low-input samples can also be separated by capillary electrophoresis (Lombard-Banek C, Moody S A, Nemes P. Single-cell mass spectrometry for discovery proteomics: quantifying translational cell heterogeneity in the 16-cell frog (Xenopus) embryo. *Angew Chem Int Ed.* 2016; 55(7):2454-8). Applicants sought to minimize nLC losses by mixing labeled peptides from single cells with labeled carrier peptides so that many of the peptides lost due to nLC adhesion will be carrier peptides rather than single-cell peptides. This strategy deviates from standard protocols for bulk LC-MS/MS.

Once injected into an MS instrument, peptide ions need at least two rounds of MS analysis for confident sequence identification (Sinitcyn P, Rudolph J D, Cox J. Computational methods for understanding mass spectrometry-based shotgun proteomics data. *Annu Rev Biomed Data Sci.* 2018; 1:207-34; Cox J, Mann M. MaxQuant enables high peptide identification rates, individualized ppb range mass accuracies and proteome-wide protein quantification. *Nat Biotechnol.* 2008; 26(12):1367-72; Eng J K, McCormack A L, Yates J R. An approach to correlate tandem mass spectral data of peptides with amino acid sequences in a protein database. *J Am Soc Mass Spectrom.* 1994; 5(11):976-89). The first MS scan (MS1) determines the mass over charge ratio (M/z) for ions that entered the instrument. Then, selected ions are accumulated and fragmented, and their fragments are analyzed by an MS2 scan (Sinitcyn P, Rudolph J D, Cox J. Computational methods for understanding mass spectrometry-based shotgun proteomics data. *Annu Rev Biomed Data Sci.* 2018; 1:207-34; Aebersold R, Mann M. Mass spectrometry-based proteomics. *Nature.* 2003; 422(6928):198-207). The most commonly used fragmentation methods break peptides at the peptide bonds with efficiency that varies much from bond to bond (Sinitcyn P, Rudolph J D, Cox J. Computational methods for understanding mass spectrometry-based shotgun proteomics data. *Annu Rev Biomed Data Sci.* 2018; 1:207-34). Since some fragments are produced with low efficiency, they will not be detected if the peptide ions have low abundance; if not enough fragments are detected, the peptide cannot be sequenced. The present invention alleviates this limitation by sending for MS2 analysis-labeled peptide ions having the same M/z (and thus the same sequence labeled with sample-specific barcodes/labels) from multiple single cells and from carrier cells so that a larger number of peptide ions are fragmented and used for sequence identification. This strategy utilizes isobaric tandem mass tags (TMT™) (Sinitcyn P, Rudolph J D, Cox J. Computational methods for understanding mass spectrometry-based shotgun proteomics data. *Annu Rev Biomed Data*

Sci. 2018; 1:207-34; Thompson A, Schafer J, Kuhn K, Kienle S, Schwarz J, Schmidt G, et al. Tandem mass tags: a novel quantification strategy for comparative analysis of complex protein mixtures by MS/MS. *Anal Chem.* 2003; 75(8):1895-904; Ross P L, Huang Y N, Marchese J N, Williamson B, Parker K, Hattan S, et al. Multiplexed protein quantitation in *Saccharomyces cerevisiae* using amine-reactive isobaric tagging reagents. *Mol Cell Proteomics.* 2004; 3(12):1154-69). TMT™ labels are used with conventional bulk LC-MS/MS to label samples of equal total protein amount (Sinitcyn P, Rudolph J D, Cox J. Computational methods for understanding mass spectrometry-based shotgun proteomics data. *Annu Rev Biomed Data Sci.* 2018; 1:207-34; Slavov N, Budnik B, Schwab D, Airoldi E, van Oudenaarden A. Constant growth rate can be supported by decreasing energy flux and increasing aerobic glycolysis. *Cell Rep.* 2014; 7:705-14; Slavov N, Semrau S, Airoldi E, Budnik B, van Oudenaarden A. Differential stoichiometry among core ribosomal proteins. *Cell Rep* 2015; 13:865-873) and offer many advantages, albeit quantification can be affected by ion co-isolation (Savitski M M, Mathieson T, Zinn N, Sweetman G, Doce C, Becher I, et al. Measuring and managing ratio compression for accurate iTRAQ/TMT quantification. *J Proteome Res.* 2013; 12(8):3586-98); the implementation of TMT™ as it relates to the present invention uses a carrier channel with much higher total protein abundance than the single cells and deviates from the standard protocols.

MS instruments have expanding, but limited, capacity for parallel ion processing and analysis (Aebersold R, Mann M. Mass spectrometry-based proteomics. *Nature.* 2003; 422 (6928):198-207; Michalski A, Damoc E, Hauschild J P, Lange O, Wieghaus A, Makarov A, et al. Mass spectrometry-based proteomics using Q Exactive, a high-performance benchtop quadrupole Orbitrap mass spectrometer. *Mol Cell Proteomics.* 2011; 10(9):M111-011015; Meier F, Beck S, Grassl N, Lubeck M, Park M A, Raether O, et al. Parallel accumulation—serial fragmentation (PASEF): multiplying sequencing speed and sensitivity by synchronized scans in a trapped ion mobility device. *J Proteome Res.* 2015; 14(12):5378-87). Thus, increase in throughput has been driven in part by decreasing the time for each step, reaching low millisecond ranges for MS scans and for ion accumulation for bulk LC-MS/MS analysis (Slavov N, Budnik B, Schwab D, Airoldi E, van Oudenaarden A. Constant growth rate can be supported by decreasing energy flux and increasing aerobic glycolysis. *Cell Rep.* 2014; 7:705-14; Michalski A, Damoc E, Hauschild J P, Lange O, Wieghaus A, Makarov A, et al. Mass spectrometry-based proteomics using Q Exactive, a high-performance benchtop quadrupole Orbitrap mass spectrometer. *Mol Cell Proteomics.* 2011; 10(9):M111-011015). On the other hand, nLC elution peaks have widths on the order of seconds (Specht H, Slavov N. Transformative opportunities for single-cell proteomics. *J Proteome Res.* 2018; 17: 2565-2571; Li S, Plouffe B D, Belov A M, Ray S, Wang X, Murthy S K, et al. An integrated platform for isolation, processing, and mass spectrometry-based proteomic profiling of rare cells in whole blood. *Mol Cell Proteomics.* 2015; 14(6): 1672-83). Thus, if a peptide elutes from the nLC for 8 s and is accumulated (sampled) for only 50 ms by an MS instrument, the instrument will measure only a small fraction of the peptide molecules in the sample (Specht H, Slavov N. Transformative opportunities for single-cell proteomics. *J Proteome Res.* 2018; 17: 2565-2571). This inefficient sampling is compensated for in standard bulk methods by the large input amount but becomes problematic for low-input samples; counting noise alone can undermine quantification (Specht H, Slavov N. Transformative opportunities for single-cell proteomics. *J Proteome Res.* 2018; 17: 2565-2571). The present invention alleviates the sampling limitation by increasing the ion accumulation (sampling) time at the expense of quantifying fewer peptides per unit time. Additional strategies for increasing sampling and mitigating its trade-offs are described in a recent perspective (Specht H, Slavov N. Transformative opportunities for single-cell proteomics. *J Proteome Res.* 2018; 17: 2565-2571), the entire teachings of which are incorporated herein by reference.

In various aspects, the invention provides methods of analyzing a test peptide in a test sample, the methods comprising: mixing labeled test peptides from the test sample, the sample having a low abundance of proteins, with labeled carrier peptides from a sample having a high abundance of proteins to form a mixture, wherein the labeled test peptides and the labeled carrier peptides have different labels; and performing liquid chromatography and tandem mass spectroscopy (LC-MS/MS) on the mixture to obtain an analysis of the labeled test peptides.

In particular embodiments, the test sample having a low abundance of proteins is from a single cell. In some embodiments, the test sample having a low abundance of proteins can be from a population of cells that have an overall low abundance of proteins to be analyzed.

In some embodiments, the sample having a high abundance of proteins is obtained from the same type of cell as the test sample having a low abundance of proteins. In further embodiments, the sample having a high abundance of proteins is obtained from a plurality of cells, such as e.g., about 10 cells or greater, about 20 cells or greater, about 30 cells or greater, about 40 cells or greater, about 50 cells or greater, about 100 cells or greater, about 200 cells or greater, about 300 cells or greater, about 400 cells or greater, about 500 cells or greater, about 600 cells or greater, about 700 cells or greater, about 800 cells or greater, about 900 cells or greater, or about 1000 cells or greater. In further embodiments, the sample having a high abundance of proteins may be enriched for one or more specific proteins that one wishes to analyze.

In some embodiments, the analysis of the labeled test peptides can comprise obtaining a relative quantification of labeled test peptides. In some embodiments, the analysis of the labeled test peptides can comprise sequencing the labeled test peptides. The phrase "relative quantification" as used herein, refers to the abundance of a protein in one sample relative to its abundance in another sample, i.e, the ratio. The peptide signal in each run provides a relative quantitation of the same peptides coming from each of the individual cells, meaning, e.g., peptide A can be compared to another peptide A in other, e.g. 7, single cells per each MS run.

In another aspect, the invention provides methods of analyzing a post-translationally modified peptide in a test sample utilizing mass spectrometry, the methods comprising: mixing labeled test peptides from the test sample, the sample having a low abundance of proteins, with labeled carrier peptides from a sample having a high abundance of post-translationally modified proteins to form a mixture, wherein the labeled test peptides and the labeled carrier peptides have different labels; and performing LC-MS/MS on the mixture to obtain an analysis of the labeled test peptides.

The present invention provides a method for quantifying post-translational modifications (PTMs) by mass spectrometry (MS) in very limited samples of complex proteomes, ranging from femtograms to nanograms and including the proteomes of single mammalian cells. Existing methods for the quantification of PTMs in complex samples require one to first enrich the sample for the PTMs of interest. Such enrichment steps typically result in significant losses of material. In the case of very small samples, such as the proteomes of single cells, the enrichment step is not feasible, i.e., it will result in losing the samples. In some embodiments, the methods provided herein overcome this challenge by making it possible to quantify PTMs in very small samples that are not enriched but are combined with larger amount(s) of labeled enriched material.

In particular embodiments, the test sample having a low abundance of post-translationally modified proteins is from a single cell. The proposed method applied to single cells, Single Cell ProtEomics by Mass Spectrometry, PTM-SCoPE, increases the sensitivity and throughput of PTM quantification by orders of magnitude over previous state of the art methods.

PTM-SCoPE allows quantifying PTMs in single human cancer and stem cells (or any cell type), and, thus, the inference of signaling activities in single human cells from heterogenous mixtures. As such, the methods can be utilized in disease diagnosis based on patient samples, including biopsies. Further, the methods provide new tools for research and development of pharmaceuticals. For example, the efficiency of a treatment (e.g., a cancer drug) can be assessed by comparing the protein(s) (e.g., levels/quantities and/or protein post-translational modifications) of cells which have undergone the treatment to cells that have not undergone the treatment (e.g., from the same patient before treatment or from a different patient or patients).

In some embodiments, the present invention comprises kits with elements and/or reagents and/or instructions for carrying out the methods described herein. In one embodiment, a kit comprises a container comprising peptides of high abundance. In one embodiment, the peptides are labeled. In another embodiment, labels are included for labeling the peptides of high abundance. In some embodiments, the kit comprises a container comprising labels for the test sample (e.g., the test sample comprising low abundance peptides).

In some embodiments, the sample having a high abundance of post-translationally modified proteins is obtained from the same type of cell as the test sample having a low abundance of proteins. In further embodiments, the sample having a high abundance of post-translationally modified proteins is obtained from a plurality of cells, such as e.g., about 10 cells or greater, about 20 cells or greater, about 30 cells or greater, about 40 cells or greater, about 50 cells or greater, about 100 cells or greater, about 200 cells or greater, about 300 cells or greater, about 400 cells or greater, about 500 cells or greater, about 600 cells or greater, about 700 cells or greater, about 800 cells or greater, about 900 cells or greater, or about 1000 cells or greater.

In some embodiments, the analysis of the labeled test peptides can comprise obtaining a relative quantification of labeled test peptides having a post-translational modification. In some embodiments, the analysis of the labeled test peptides can comprise sequencing the labeled test peptides having a post-translation modification.

A non-limiting list of post-translational modifications that can be analyzed by the methods described herein include phosphorylation, acetylation, ubiquitination, O-glycosylation, N-glycosylation, methylation, sumoylation and combinations thereof.

In one embodiment, the sample having a high abundance of post-translationally modified proteins is enriched for post-translationally modified proteins. In some embodiments, the post-translationally modified proteins are enriched by antibody based selection for post-translationally modified proteins. In some embodiments, the post-translationally modified proteins are enriched by chemically based selection for post-translationally modified proteins. Any chemical or antibody based mechanism for enrichment can be used. For example, one can enrich cells from biofluids by, e.g., by using an antibody and then use the enriched cells as a carrier channel to boost sensitivity for the particular type of cell.

Procedurally, the first step of, for example, phosphor SCoPE involves PTM enrichment of a bulk sample (the carrier) with similar protein composition as the low-input samples that one aims to analyze, e.g., quantify. The enrichment may include, e.g., (1) TiO2 and/or IMAC procedures for phosphorylated peptides or (2) antibody-based pull down for modifications such as N-terminus acetylation, and/or ubiquitination, or (3) lectin agarose beads for O-glycosylation and N-glycosylation. Based on the enrichment step, one can use an enriched material in each case as a "carrier" channel for selective identification of only modified peptides in the whole proteome mixtures of each individually TMT™ labeled channel of low abundant material based on peptides that dominate by abundance of enriched material in the "carrier" channel.

As a result of data independent MS/MS TMT™ based quantitation analysis, in some embodiments, one can quantify the levels of PTM-labeled peptides from low ultra-low amount samples, down to the proteomes of single mammalian cells with diameters of 11 microns.

In embodiments of the various aspects provided herein, the test peptide from the test sample having a low abundance of proteins can be obtained by: freezing the test sample to about −80 degrees Celsius and then heating the test sample to about 90 degrees Celsius to obtain a lysate; digesting the lysate to obtain digested test peptides; and labeling the digested test peptides to obtain labeled test peptides.

A major limitation, as previously discussed herein, to applying quantitative LC-MS/MS proteomics to small samples, such as single cells, are the losses incurred during sample cleanup. To relieve this limitation, a Minimal ProteOmic sample Preparation (mPOP) method for culture-grown mammalian cells was also developed. (see Specht, H. Harmange, G. Perlman, D. H., Emmott, E., Niziolek, Z., Budnik, B. and Slavov, N. Automated sample preparation for high-throughput single-cell proteomics. *bioRxiv*. https://doi.org/10.1101/399774; incorporated herein by reference in its entirety). mPOP obviates cleanup and thus eliminates cleanup-related losses while expediting sample preparation and simplifying its automation. As exemplified later herein, bulk SILAC samples processed by mPOP or by conventional urea-based methods indicated that mPOP results in complete cell lysis and accurate relative quantification. mPOP lysis was then integrated with the Single Cell ProtEomics by Mass Spectrometry (SCoPE-MS) sample preparation methods described herein, and the quantification of such samples were benchmarked on a Q-exactive instrument. The results as described later herein demonstrate low noise and high technical reproducibility. Additionally, Applicants FACS sorted single U-937, HEK-293, and mouse ES cells into 96-well plates and analyzed them by automated mPOP and SCoPE-MS. The quantified proteins enabled separating the single cells by cell-type and cell-division-cycle phase.

Methods for preparing sub-microgram protein samples for LC-MS/MS often use sophisticated custom-made equipment (Specht, H. & Slavov, N. Transformative opportunities for single-cell proteomics. *Journal of Proteome Research* 17, 2563-2916 (8 Jun. 2018); Zhu, Y. et al. Nanodroplet processing platform for deep and quantitative proteome profiling of 10-100 mammalian cells. *Nature communications* 9,882 (2018); Levy, E. & Slavov, N. Single cell protein analysis for systems biology. *Essays In Biochemistry* 62.doi:10.1042/EBC20180014 (4 2018)) and generally lyse cells by detergents or chaotropic agents like urea (Levy, E. & Slavov, N. Single cell protein analysis for systems biology. *Essays In Biochemistry* 62.doi:10.1042/EBC20180014 (4 2018); Dhabaria, A., Cifani, P., Reed, C., Steen, H. & Kentsis, A. A high-efficiency cellular extraction system for biological proteomics. *Journal of proteome research* 14, 3403-3408 (2015)). Techniques using these chemicals are robust but require that the chaotropic agents or detergents be removed before MS analysis since these chemicals are incompatible with MS (Dhabaria, A., Cifani, P., Reed, C., Steen, H. & Kentsis, A. A high-efficiency cellular extraction system for biological proteomics. *Journal of proteome research* 14, 3403-3408 (2015)). Some cleanup methods, such as SP3 (Hughes, C. S. et al. Ultrasensitive proteome analysis using paramagnetic bead technology. *Molecular systems biology* 10, 757 (2014)) and iST (Kulak, N. A., Pichler, G., Paron, I., Nagaraj, N. & Mann, M. Minimal, encapsulated proteomic-sample processing applied to copy-number estimation in eukaryotic cells. *Nature methods* 11, 319 (2014)) perform very well even for microgram samples (Dhabaria, A., Cifani, P., Reed, C., Steen, H. & Kentsis, A. A high-efficiency cellular extraction system for biological proteomics. *Journal of proteome research* 14, 3403-3408 (2015); Sielaff, M. et al. Evaluation of FASP, SP3, and iST Protocols for Proteomic Sample Preparation in the Low Microgram Range. *Journal of proteome research* 16, 4060-4072 (2017)). Yet losses are more significant for the preparation of low-abundance samples, such as single cells. Furthermore, cleanup steps complicate automation and may introduce variability between samples. Thus, avoiding cleanup stages can reduce losses while increasing throughput and consistency (Specht, H. & Slavov, N. Transformative opportunities for single-cell proteomics. *Journal of Proteome Research* 17, 2563-2916 (8 Jun. 2018)). A cell lysis method that does not require MS-incompatible chemicals and thus can be used for LC-MS/MS without cleaning is focused acoustic sonication (FAS) (Dhabaria, A., Cifani, P., Reed, C., Steen, H. & Kentsis, A. A high-efficiency cellular extraction system for biological proteomics. *Journal of proteome research* 14, 3403-3408 (2015); Li, S. et al. An integrated platform for isolation, processing, and mass spectrometry-based proteomic profiling of rare cells in whole blood. *Molecular & Cellular Proteomics* 14, 1672-1683 (2015)). Applicants successfully used FAS to obviate cleaning up single-cell lysates and to develop Single Cell ProtEomics by Mass Spectrometry (SCoPE-MS) (Budnik, B., Levy, E., Harmange, G. & Slavov, N. Mass-spectrometry of single mammalian cells quantifies proteome heterogeneity during cell differentiation. *bioRxiv*1, DOI:10.1101/102681 (2017)). While FAS resulted in clean lysis, it required significant volumes (5-10 µl), was low-throughput, and used expensive consumables and equipment (Budnik, B., Levy, E., Harmange, G. & Slavov, N. Mass-spectrometry of single mammalian cells quantifies proteome heterogeneity during cell differentiation. *bioRxiv*1, DOI:10.1101/102681 (2017)). These limitations hinder its potential for high-throughput single-cell proteomics (Specht, H. & Slavov, N. Transformative opportunities for single-cell proteomics. *Journal of Proteome Research* 17, 2563-2916 (8 Jun. 2018)).

As such, in another aspect, the present invention provides methods of lysing a cell sample, e.g., a single cell, for protein extraction, comprising:

freezing the cell sample to about −80 degrees Celsius; and
heating the cell sample after freezing to about 90 degrees Celsius to obtain a lysate for protein extraction. In one embodiment, the freezing step is performed before the heating step. In other embodiments, the heating step is performed before the freezing step.

In some embodiments, the methods of lysing a cell sample can further comprise digesting the lysate to obtain peptides. In some embodiments, the methods further comprise labeling the peptides to obtain labeled peptides.

The methods described herein can apply to multiple cells (a plurality of cells) or to a single cell.

While example embodiments have been particularly shown and described, it will be understood by those skilled in the art that various changes in form and details may be made therein without departing from the scope of the embodiments encompassed by the appended claims.

EXAMPLES

Materials and Methods

The following materials and methods were utilized in the examples described herein.

Cell Culture

Mouse embryonic stem cells ($E_{14}$ 10th passage) were grown as adherent cultures in 10-cm plates with 10 ml Knockout DMEM media supplemented with 10% ES-certified FBS, nonessential amino acids (NEAA supplement), 2 mM L-glutamine, 110 µM β-mercapto-ethanol, 1% penicillin and streptomycin, and leukemia inhibitory factor (mLIF; 1000 U LIF/ml). ES cells were passaged every 2 days using StemPro Accutase on gelatin-coated tissue culture plates. ES differentiation was triggered by passaging the ES cells into media lacking mLIF in low adherence plates and growing the cells as suspension cultures. Jurkat and U937 cells were grown as suspension cultures in RPMI medium (HyClone 16777-145) supplemented with 10% FBS and 1% pen/strep. Cells were passaged when a density of $10^6$ cells/ml was reached, approximately every 2 days.

Cell Culture for mPOP Related Experimentation

Jurkat and U-937 cells were grown as suspension cultures in RPMI medium (HyClone 16777-145) supplemented with 10% fetal bovine serum (FBS) and 1% pen/strep. Cells were passaged when a density of $10^6$ cells/ml was reached, approximately every two days. HEK-293 were grown as adherent cultures in DMEM supplemented with 10% FBS and 1% pen/strep and passaged at 70% confluence, approximately every two days. Mouse embryonic stem cells expressing the FUCCI system were grown as adherent cultures in 10 cm plates with 10 ml Knockout DMEM media supplemented with 10% ES certified FBS, non-essential amino acids supplements, 2 mM L-glutamine, 110 µM β-mercapto-ethanol, 1% penicillin and streptomycin, and leukemia inhibitory factor (mLIF; 1,000 U LIF/ml). ES cells were passaged every two days using StemPro Accutase on gelatin coated tissue culture plates. Starting six passages prior to harvesting, ES cells were grown in media containing DMEM/F12 with N2, B27, and NEAA supplements, 1% pen/strep, 110 µM β-mercapto-ethanol, 3 mM L-glutamine, 200 ug/ml human insulin, 1 µM PD0325901, 3 µM CHIR99021, and 1e4 units/ml mLIF.

Harvesting Cells for SCoPE-MS

To harvest cells, embryoid bodies were dissociated by treatment with StemPro Accutase (Thermo Fisher #A1110501) and gentle pipetting. Cell suspensions of differentiating ES cells, Jurkat cells, or U-937 cells were pelleted and washed quickly with cold phosphate buffered saline (PBS). The washed pellets were diluted in PBS at 4° C. The cell density of each sample was estimated by counting at least 150 cells on a hemocytometer, and an aliquot corresponding to 200 cells was placed in a Covaris microTUBE-15, to be used for the carrier channel. For picking single cells, two 200-µL pools of PBS were placed on a cooled glass slide. Into one of the pools, 2 µL of the cell dilution was placed and mixed, to further dilute the solution. A single cell was then picked under a microscope into a micropipette from this solution. Then, to verify that only one cell was picked, the contents of the micropipette were ejected into the other pool of PBS, inspected, then taken back into the pipette and placed in a chilled Covaris microTUBE-15. Cell samples in Covaris microtubes were frozen as needed before cell lysis and labeling.

Harvesting Cells for mPOP

To harvest cells, embryoid bodies were dissociated by treatment with StemPro Accutase (ThermoFisher #A1110501) and gentle pipetting. HEK-293 cells were dissociated by gently pipetting. Cell suspensions of differentiating ES cells, Jurakt cells or U-937 cells were pelleted and washed quickly with cold phosphate buffered saline (PBS) at 4° C. The washed pellets were diluted in PBS at 4° C. The cell density of each sample was estimated by counting at least 150 cells on a hemocytometer.

Sorting Cells by FACS

Adenocarcinoma cells (MDA-MB-231) expressing mCherry and LifeAct-iRFP670 were sorted by Aria FACS into PCR strip-tubes, one cell per tube. Each tube contained 2 µL of water and had a max volume of 200 µL. The fluorescence of each protein was measured and the protein abundance estimated after compensation for the spectral overlap between mCherry and iRFP.

HEK-293 and U-937 cells were sorted by FACS (Beckman Coulter MoFlo Astrios EQ Cell Sorter) into 2 µL of pure water in 96-well PCR plates (Eppendorf twin.tec E951020303). Mouse embryonic stem cells were sorted by FACS (BD FACSAria I) into the same type of 96-well PCR plates. The mouse embryonic stem cells express the fucci system, and were sorted based on fluorescence of the citrine-geminin fusion protein.

Cell Lysis and Digestion

Each sample—containing a single cell or carrier cells—was lysed by sonication in a Covaris 5220 instrument (Woburn, Mass.) (Li S, Plouffe B D, Belov A M, Ray S, Wang X, Murthy S K, et al. An integrated platform for isolation, processing, and mass spectrometry-based proteomic profiling of rare cells in whole blood. *Mol Cell Proteomics*. 2015; 14(6):1672-83). Samples were sonicated for 180 s at 125 W power with 10% peak duty cycle, in a degassed water bath at 6° C. During the sonication, samples were shaken to coalesce droplets and bring them down to the bottom of the tube. After lysis, the samples were heated for 15 min at 90° C. to denature proteins. Then, the samples were spun at 3000 rpm for 1 min, and (50 ng/µL) trypsin was added: 0.5 µL to single cells and 1 µL to carrier cells. The samples were digested overnight, shaking at 45° C. Once the digest was completed, each sample was labeled with 1 µL of 85 mM TMT™ label (TMT™10 kit, Thermo Fisher, Germany). The samples were shaken for 1 h in a tray at room temperature. The unreacted TMT™ label in each sample was quenched with 0.5 µL, of 5% hydroxylamine for 15 min according to the manufacturer's protocol. The samples corresponding to one TMT™10 plex were then mixed in a single-glass HPLC vial and dried down to 10 µL in a speed vacuum (Eppendorf, Germany) at 35° C.

Cell Lysis and Digestion for mPOP

Bulk and single cells alike were lysed by freezing at −80° C. for at least 5 minutes and heating to 90° C. for 10 minutes. Then, samples were centrifuged briefly to collect liquid, and trypsin (Promega Trypsin Gold) and buffer triethylammonium bicarbonate (TEAB) (pH 8.5) were added to 10 ng/µl) and 100 mM, respectively. The samples were digested for 4 hours in a thermal cycler at 37° C. (BioRad T100). Samples were cooled to room temperature and labeled with 1 µl of 43 mM TMT™ label (TMT™11 kit, ThermoFisher, Germany) for 1 hour. The unreacted TMT™ label in each sample was quenched with 0.5 µl of 0.5% hydroxylamine for 30 minutes at room temperature. Samples were centrifuged briefly following all reagent additions to collect liquid. The samples corresponding to one TMT™11 plex were then mixed in a single glass HPLC vial and dried down to 10 µl in a speed-vacuum (Eppendorf, Germany) at 35° C.

Master Mix Preparation

Figure 12B:
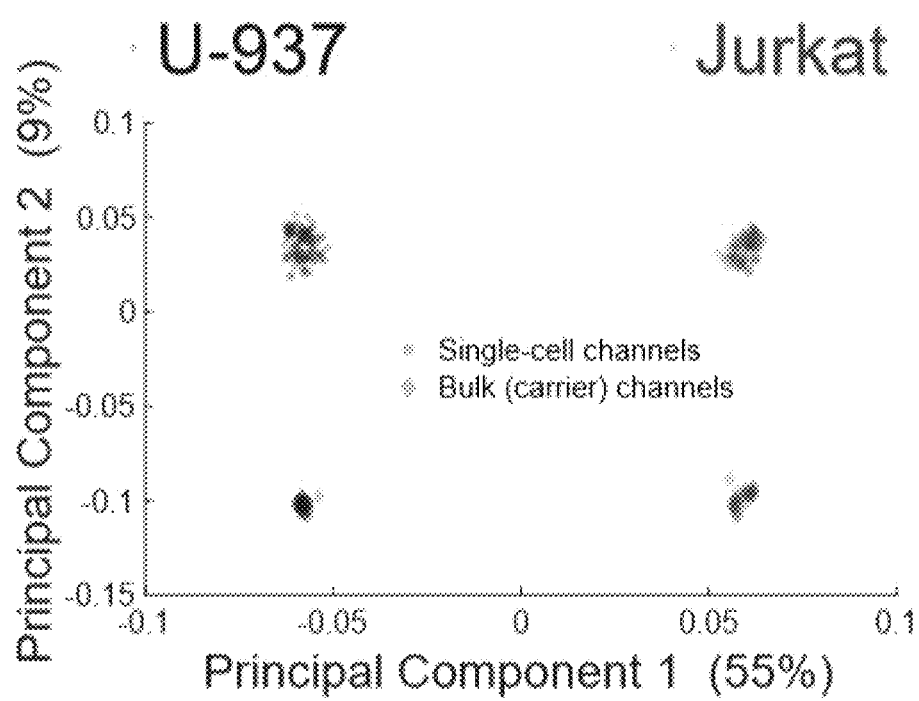

Jurkat and U-937 cells were harvested and counted as described above. Five thousand three hundred cells from each type were digested (100 mM TEAB pH 8.5, 10 ng/µl trypsin at 37° C. for 4 hours), divided into 5000, 100, 100, and 100 cell equivalents, labeled with TMT™11, and combined such that there are two carrier channels of 5000 cell equivalents (one of Jurkat, one of U-937) and six channels of 100 cell equivalents, three of Jurkat and three of U-937 (FIG. 12A). This sample was diluted 100× and aliquoted into glass HPLC vials. Material equivalent to 50 cells in the two carrier channels and 1 cell in the six other channels was injected for analysis by LC-MS/MS.

Bulk Set

The six bulk samples of Jurkat and U-937 cells contained 2500 cells per sample. The cells were harvested, lysed, and processed using the same procedure as for the single cells but with increased amount of trypsin and TMT™ labels. The samples were labeled, mixed, and run as a 6-plex TMT™ set.

Mass Spectrometry Analysis

Each TMT™ labeled set of samples was submitted for single LC-MS/MS experiment that was performed on a LTQ Orbitrap Elite (Thermo Fisher) equipped with a Waters (Milford, Mass.) NanoAcquity HPLC pump. Peptides were first trapped and washed onto a 5 cm×150 µm inner diameter microcapillary trapping column packed with C18 Reprosil resin (5 µm, 10 nm, Dr. Maisch GmbH, Germany). The peptides were separated on an analytical column 20 cm×75 µm of C18 TPP beads (1.8 µm, 20 nm, Waters, Milford, Mass.) that was heated to 60° C. Separation was achieved through applying an active gradient from 7 to 27% ACN in 0.1% formic acid over 170 min at 200 nl/min. The active gradient was followed by a 10-min 27-97% ACN wash step. Electrospray ionization was enabled through applying a voltage of 1.8 kV using a homemade electrode junction at the end of the microcapillary column and sprayed from fused silica pico-tips (20 µm ID, 15 µm tip end New Objective, MA). The LTQ Orbitrap Elite was operated in data-dependent mode for the mass spectrometry methods. The mass spectrometry survey scan (MS1) was performed in the Orbitrap in the range of 395-1,800 m/z at a resolution of $6×10^4$, followed by the selection of up to 20 most intense ions (TOP20) for HCD-MS2 fragmentation in the Orbitrap using the following parameters: precursor isolation width window of 1 or 2 Th, AGC setting of 100,000, a maximum ion accumulation time of 150 ms or 250 ms, and $6\times10^4$ resolving power. Singly charged and 4+ charge ion species were excluded from HCD fragmentation. Normalized collision energy was set to 37 V and an activation time of 1 ms. Ions in a 7.5-ppm m/z window around ions selected for MS2 were excluded from further selection for fragmentation for 20 s.

SILAC data was acquired using a Dionex UltiMate 3000 UHPLC with a 25 cm length×75 µm inner diameter microcapillary column packed with C18 Reprosil resin (1.9 µm resin, Dr. Maisch GmbH, Germany). Peptides were separated at 150 nL/min over a 180-minute gradient and analyzed on a Thermo Scientific Lumos mass spectrometer. After a precursor scan from 400 to 2000 m/z at 50,000 resolution, the top 10 most intense multiply-charged precursors (charges 2 to 4) were selected for alternating HCD and CID fragmentation at 50,000 and 35,000 resolutions, respectively. Mouse embryonic stem cell (SCoPE-MS) data was acquired using a Proxeon Easy nLC1200 UHPLC (Thermo Scientific) at a flow rate of 200 nL/min using a 25 cm length×75 µm Waters nanoEase column (1.7 µm resin, Waters PN:186008795) over a 60 minute gradient. Peptides were analyzed by a Thermo Scientific Q-Exactive mass spectrometer. After a precursor scan from 450 to 1600 m/z at 70,000 resolution, the top 5 most intense precursors with charges 2 to 4 were selected for HCD fragmentation at resolution 70,000 with a max fill time of 300 ms. A 0.7 Th isolation window was used for MS2 scans.

Analysis of Raw MS Data

Raw data were searched by MaxQuant (Cox J, Mann M. MaxQuant enables high peptide identification rates, individualized ppb range mass accuracies and proteome-wide protein quantification. *Nat Biotechnol*. 2008; 26(12):1367-72; Cox J, Neuhauser N, Michalski A, Scheltema R A, Olsen J V, Mann M. Andromeda: a peptide search engine integrated into the MaxQuant environment. *J Proteome Res*. 2011; 10(4):1794-805) 1.5.7.0 against a protein sequence database including all entries from a SwissProt database and known contaminants such as human keratins and common lab contaminants. The SwissProt databases were the human SwissProt database for the U-937 and the Jurkat cells and the mouse SwissProt database for the differentiating ES cells. MaxQuant searches were performed using the standard work flow (Tyanova S, Temu T, Cox J. The MaxQuant computational platform for mass spectrometry-based shotgun proteomics. *Nat Protoc*. 2016; 11(12):2301). Applicants specified trypsin specificity and allowed for up to two missed cleavages for peptides having from 5 to 26 amino acids. Methionine oxidation (+15.99492 Da) was set as a variable modification. All peptide-spectrum matches (PSMs) and peptides found by MaxQuant were exported in the msms.txt and the evidence.txt files.

Figure 2A:
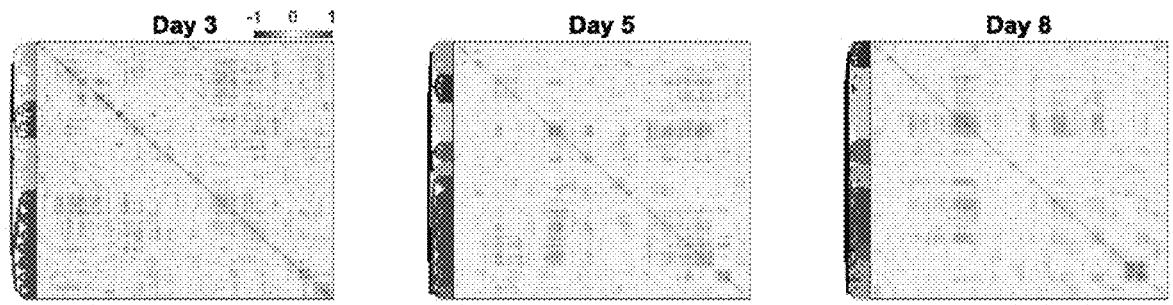
FIGS. 2A-2D provide example experimental data identifying protein covariation across differentiating ES cells.

In addition to a standard search with the full SwissProt databases, the MS data was also searched with custom sequence databases since such searches have advantages when the sequences can be better tailored to the peptides analyzed by MS (Nesvizhskii A I. Proteogenomics: concepts, applications and computational strategies. *Nat Methods*. 2014; 11(11):1114; Woo S, Cha S W, Merrihew G, He Y, Castellana N, Guest C, et al. Proteogenomic database construction driven from large scale RNA-seq data. *J Proteome Res*. 2013; 13(1):21-8). In the case of SCoPE-MS, sequences can be removed for lowly abundant proteins since their peptides are very unlikely to be sent for MS2. Indeed, searches with the full databases did not identify peptides from the least abundant proteins (FIG. 2A). Excluding such proteins from the search can narrow down the search space and increase the statistical power for identifying the correct peptide-spectrum matches (Nesvizhskii A I. Proteogenomics: concepts, applications and computational strategies. *Nat Methods*. 2014; 11(11):1114; Woo S, Cha S W, Merrihew G, He Y, Castellana N, Guest C, et al. Proteogenomic database construction driven from large scale RNA-seq data. *J Proteome Res*. 2013; 13(1):21-8). To take advantage of this approach, the MS data was searched with custom databases comprised from all proteins for which MaxQuant had identified at least one peptide across many single-cell and small-bulk sets in searches against the full SwissProt databases. These reduced fasta databases contained 5267 proteins for mouse and 4961 proteins for human. Searches with them slightly increased the number of identified peptides from SCoPE-MS sets but such customized databases are not essential for SCoPE-MS.

Figure 8A:
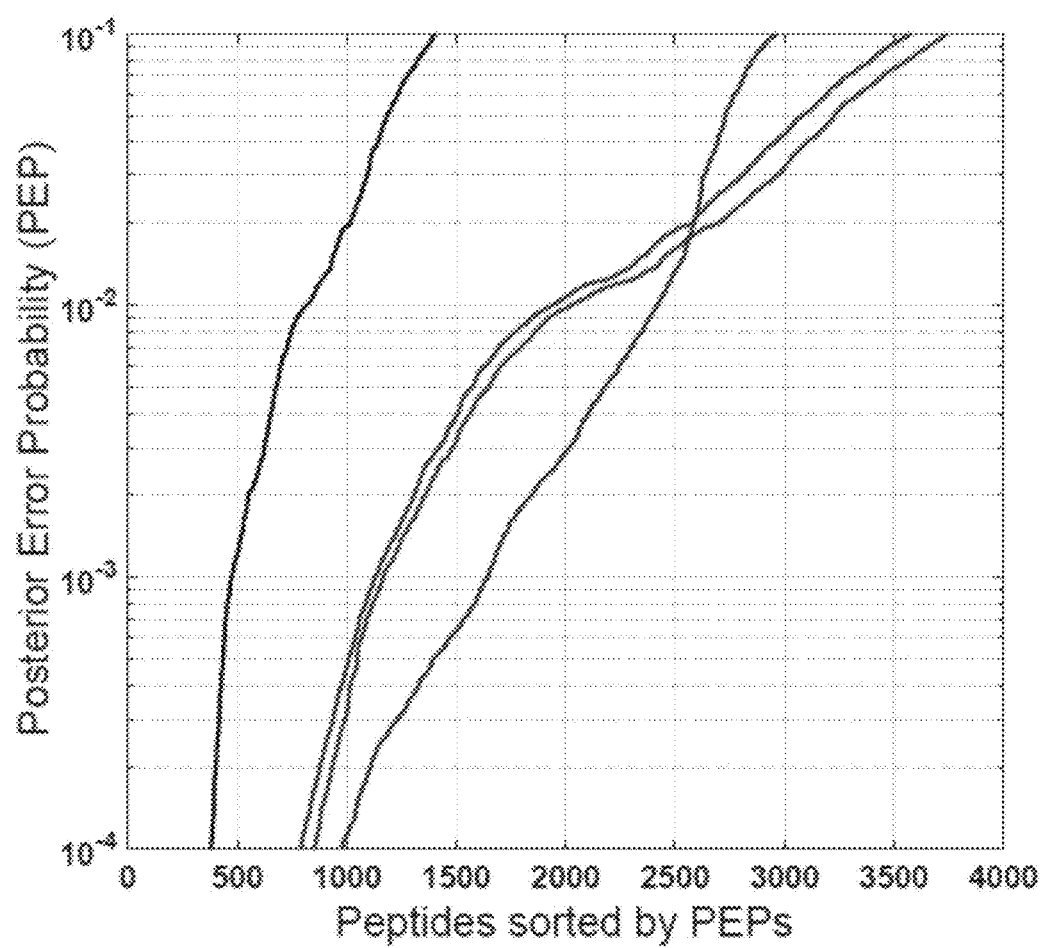
FIGS. 8A-8C illustrates the confidence of peptide identification and its effect on quantification.
Figure 8B:
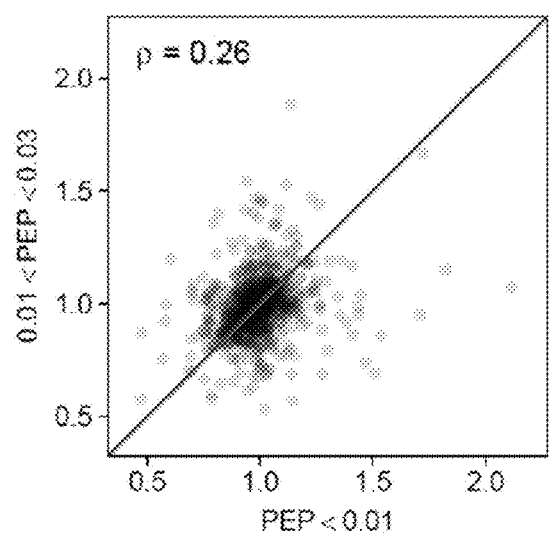
Figure 8C:
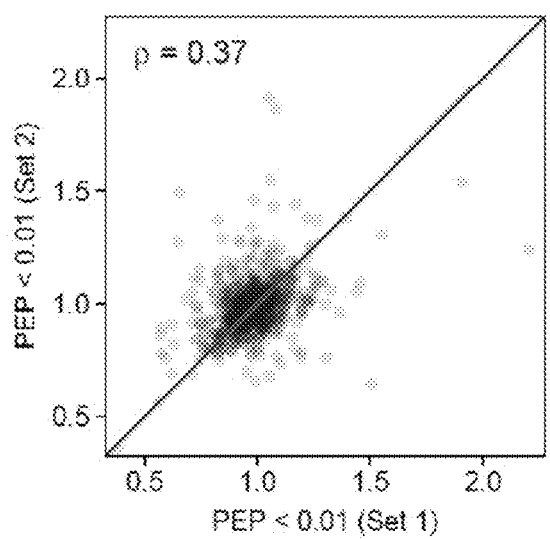

The shotgun approach results in identifying different peptides in different SCoPE-MS sets at different levels of confidence. Because of the lower protein levels in SCoPE-MS sets compared to bulk sets, fewer fragment ions are detected in the MS2 spectra and thus peptide identification is more challenging than with bulk datasets. As a result, the 1% FDR threshold that is optimal for bulk MS data may not be optimal for SCoPE-MS datasets. To determine the FDR threshold that is optimal for single-cell data, Applicants plotted the number of identified peptides at all levels of posterior error probability (PEP) (FIG. 8A). This analysis suggests that a slight increase in the arbitrary FDR threshold or 1% results in a significant increase in the peptides that can be usefully analyzed across single cells while still keeping false positives low. Thus, peptides from SCoPE-MS sets were filtered to 3% FDR computed as the mean of the PEP of all peptides below the PEP cutoff threshold (Franks A, Airoldi E, Slavov N. Post-transcriptional regulation across human tissues. *PLoS Comput Biol*. 2017; 13(5): e1005535). To validate the protein ratios derived from peptides having PEP∈(0.01, 0.03], Applicants correlated them to the corresponding protein ratios derived from peptides having PEP<0.01 (FIG. 8B). The positive correlation in FIG. 8B indicates that peptides identified with lower confidence carry quantitative information. Still, this correlation is lower than the correlations between ratios derived from two subsets of peptides having PEP<0.01 (FIG. 8C). This may be due at least in part to the fact that factors reducing the confidence of identification, such as lower abundance or higher co-isolation, are also likely to undermine quantification. All razor peptides were used for quantifying the proteins to which they were assigned by MaxQuant. The average number of identified peptides per TMT™ set is as shown for a few SCoPE-MS sets in FIG. 8A as a technical benchmark but it has much less practical significance than the number of proteins that are quantified across enough single cells to be useful for analysis (Specht H, Slavov N. Transformative opportunities for single-cell proteomics. *J Proteome Res*. 2018; 17:2563-916). This number of genes quantified across multiple sets is the standard measure for single-cell RNA sequencing methods (Klein A M, Mazutis L, Akartuna I, Tallapragada N, Veres A, Li V, et al. Droplet barcoding for single-cell transcriptomics applied to embryonic stem cells. *Cell*. 2015; 161(5):1187-201), and Applicants have adopted it for SCoPE-MS as the more meaningful measure of the proteins whose levels can be analyzed across multiple single cells.

Analysis of Raw MS Data for mPOP Experiments

Raw data were searched by MaxQuant 1.6.0.16 and 1.6.2.3 (Cox, J. & Mann, M. MaxQuant enables high peptide identification rates, individualized ppb-range mass accuracies and proteome-wide protein quantification. *Nature biotechnology* 26, 1367-1372 (2008); Cox, J. et al. Andromeda: a peptide search engine integrated into the MaxQuant environment. *Journal of proteome research* 10, 1794-1805 (2011)) against a protein sequence database including all entries from the appropriate mouse or human SwissProt database (downloaded Jul. 15, 2018 and Jul. 30, 2018, respectively) and known contaminants such as human keratins and common lab contaminants. MaxQuant searches were performed using the standard work flow (Tyanova, S., Temu, T. & Cox, J. The MaxQuant computational platform for mass spectrometry based shotgun proteomics. *Nature protocols* 11, 2301 (2016)). Applicants specified trypsin specificity and allowed for up to two missed cleavages for peptides having from 5 to 26 amino acids. Methionine oxidation (+15.99492 Da) and protein N-terminal acetylation (+42.01056 Da) were set as a variable modifications. Carbamidomethylation was disabled as a fixed modification. All peptide-spectrum-matches (PSMs) and peptides found by MaxQuant were exported in the msms.txt and the evidence.txt files. SILAC data was searched in two batches (by date acquired) with match between runs enabled, using the default settings.

Data Analysis

Relative peptide/protein levels were estimated from the TMT™ reporter ions (RI), and protein abundances from the precursor areas distributed according to the RI levels. While such estimates are well validated with bulk samples, extremely low input amounts pose unique challenges that may result in artifacts, e.g., RI intensities may reflect only background noise or the isotopic impurities of TMT™ tags may cross contaminate TMT™ channels. The degree of background noise was evaluated and found significantly below the signal coming from the labeled peptides (FIG. 5A-5D). To compensate for different amounts of total protein per channel or other channel-specific variability, the median RI intensities in each channel was set to one by diving all RI intensities by their median. In the FACS experiment, the normalization for mCherry was performed using iRFP as a control, analogous to loading controls in western blots. After this column normalization, the vector of RI intensities for each peptide was divided by its mean or median, to remove the large differences in abundances between different peptides. The relative level of each quantified razor protein was estimated as the median of the relative levels of its peptides. All analysis relied on relative levels, i.e., the level of protein in a cell relative to its mean or median level across all cells in which the protein is quantified. Missing peptide and protein levels were imputed using the k-nearest Neighbors algorithm, with k being set to 1 and the similarity measure for distance being the cosine of the angle between the proteome vectors.

Relative Quantification Across SCoPE-MS Sets

SCoPE-MS allows quantifying only eight cells per set (FIG. 1A-1E), but combining multiple sets can quantify the proteomes of hundreds and thousands of cells. Applicants were able to successfully combine relative protein levels across SCoPE-MS sets in two different ways: (i) When the carrier material used across sets is the same (FIG. 1B), Applicants used the carrier channel as a reference as established with bulk TMT™ samples (Slavov N, Budnik B, Schwab D, Airoldi E, van Oudenaarden A. Constant growth rate can be supported by decreasing energy flux and increasing aerobic glycolysis. *Cell Rep.* 2014; 7:705-14). (ii) When the carrier material differed across carrier channels (FIG. 6A-6C), Applicants excluded the carrier channel from the analysis and normalized the relative levels of each peptide to a mean 1 across the eight single cells in each set, four Jurkat and four U-937 cells. Approach (ii) worked well in this case because the single-cell composition of the different SCoPE-MS sets was balanced. Combining SCoPE-MS sets based on a reference channel that is kept the same across all sets is a more versatile strategy that generalizes to any experimental design and single-cell distribution across sets.

Principle Component Analysis for Single Cell Data Sets

Using the data analysis language R (v3.4.1), the matrix of peptide-level quantitation from TMT™ reporter ions was normalized prior to PCA analysis. Columns (corresponding to separate TMT™ channels) were divided by their median value. Rows (corresponding to peptides from individual TMT™11-plexes) were divided by their mean, then the mean of the resulting vector subtracted from all values in the vector.

SILAC Data Normalization

Expected SILAC ratios for peptides were computed by taking the mean of the SILAC ratios from samples containing equal number of SILAC heavy and SILAC light U-937 cells, processed by the urea-based method. All subsequent samples, processed either by mPOP or the urea-based method, were normalized by these values to account for artifacts from SILAC labeling.

EXAMPLE 1

Development of a High-Throughput Method for Single Cell Proteomics by Mass Spectrometry (SCoPE-MS)

To develop a high-throughput method for Single Cell ProtEomics by Mass Spectrometry (SCoPE-MS), LC-MS/MS methods were altered for bulk samples. In particular, two major challenges were resolved: (i) delivering the proteome of a mammalian cell to a MS instrument with minimal protein losses and (ii) simultaneously identifying and quantifying peptides from single-cell samples. To overcome the first challenge, live single cells were manually picked under a microscope and mechanically lysed (by Covaris sonication in glass microtubes) (FIG. 1A). This method was chosen to obviate chemicals that may undermine peptide separation and ionization or sample cleanup that may incur significant losses. The proteins from each cell lysate were quickly denatured at 90° C. and digested with trypsin at 45° C. overnight (FIG. 1A). Special care was taken to ensure that each tube contained only one cell. See "Materials and Methods" for full experimental details.

To overcome the second challenge, novel use of tandem mass tags (TMT™) was utilized. This technology was developed for multiplexing (Thompson A, Schafer J, Kuhn K, Kienle S, Schwarz J, Schmidt G, et al. Tandem mass tags: a novel quantification strategy for comparative analysis of complex protein mixtures by MS/MS. *Anal Chem.* 2003; 75(8):1895-904; Ross P L, Huang Y N, Marchese J N, Williamson B, Parker K, Hattan S, et al. Multiplexed protein quantitation in Saccharomyces cerevisiae using amine-reactive isobaric tagging reagents. *Mol Cell Proteomics.* 2004; 3(12):1154-69), which is usually employed for cost-effective increase in throughput. Even more crucial to our application, TMT™ allows quantifying the level of each TMT™-labeled peptide in each sample while identifying its sequence from the total peptide amount pooled across all samples (Thompson A, Schafer J, Kuhn K, Kienle S, Schwarz J, Schmidt G, et al. Tandem mass tags: a novel quantification strategy for comparative analysis of complex protein mixtures by MS/MS. *Anal Chem.* 2003; 75(8):1895-904; Ross P L, Huang Y N, Marchese J N, Williamson B, Parker K, Hattan S, et al. Multiplexed protein quantitation in *Saccharomyces cerevisiae* using amine-reactive isobaric tagging reagents. *Mol Cell Proteomics.* 2004; 3(12):1154-69). SCoPE-MS capitalizes on this capability by augmenting each single-cell set with a sample comprised of about 200 carrier cells that provide enough ions for peptide sequence identification (FIG. 1A). The carrier cells also help with the first challenge by reducing losses from single cells, since most of the peptides lost due to surface adhesion will likely originate from the carrier cells. Thus, the introduction of labeled carrier cells into single-cell TMT™ sets helps overcome the two major challenges.

Figure 5A:
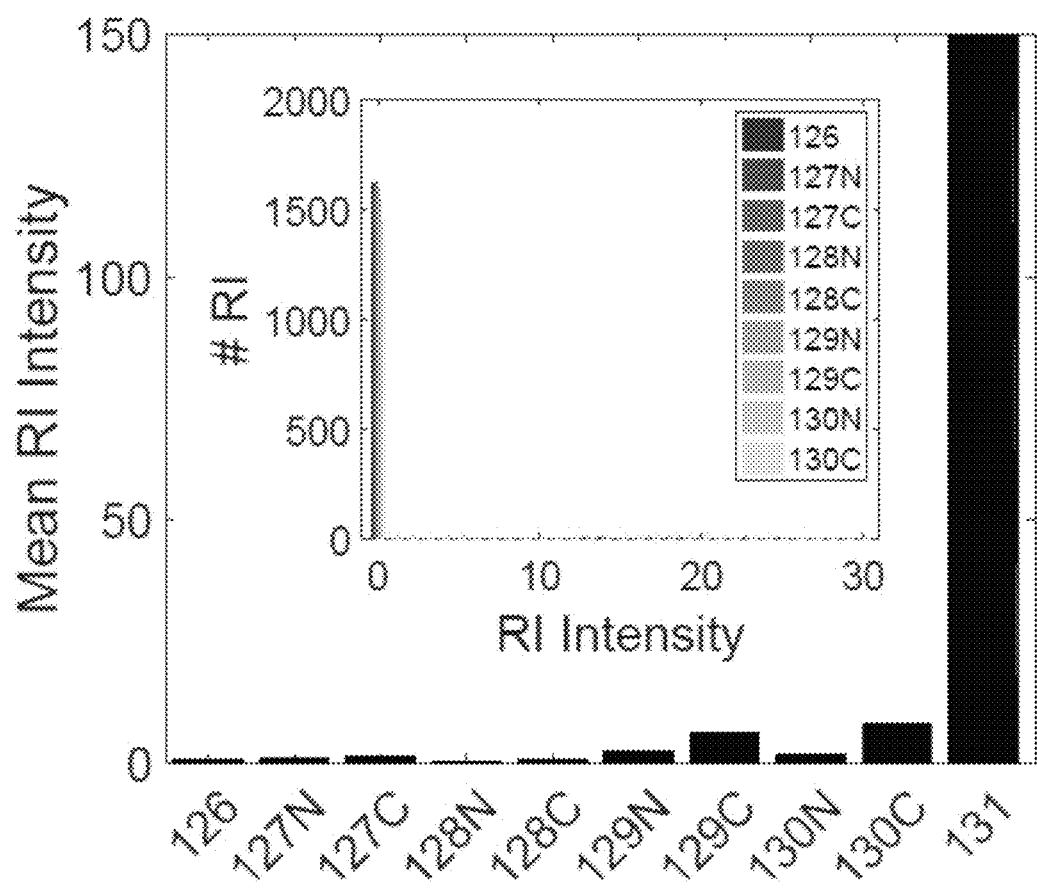
FIG. 5A illustrates the reporter ion (RI) intensities in a SCoPE set in which the single cells were omitted while all other steps were carried out, i.e., trypsin digestion, TMT™ labeling and addition of carrier cells in channel 131. Thus, RI intensities in channels 126-130C correspond to background noise. The distribution of RI intensities in the inset shows that the RI for most peptides in channels 126-130C are zero, i.e., below the MaxQuant noise threshold. The y-axis is limited to 150 to make the mean RI intensities visible. The mean RI intensity for single-cell channels is about 500.
Figure 5B:
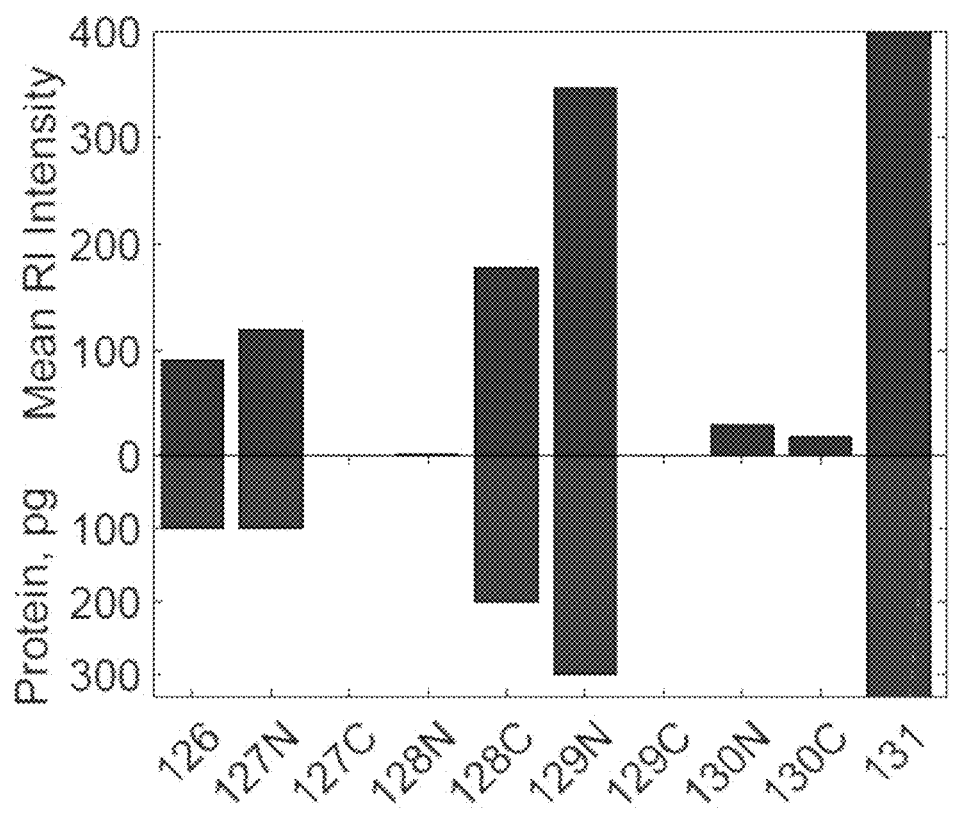
FIG. 5B illustrates the mean RI intensities for a TMT™ set in which only 6 channels contained labeled proteome digests and the other 4 were left empty. Channels 126, 127N, 128C, and 129N correspond to peptides diluted to levels corresponding to 100, 100, 200 and 300 picograms of cellular proteome, channel 131 corresponds to the carrier cells (bars truncated by axes), and the remaining channels were left empty. The RI for most peptides are not detected in the empty channels, and their mean levels very low. This suggests that background noise is low compared to the signal from peptides corresponding to a single cell.
Figure 5C:
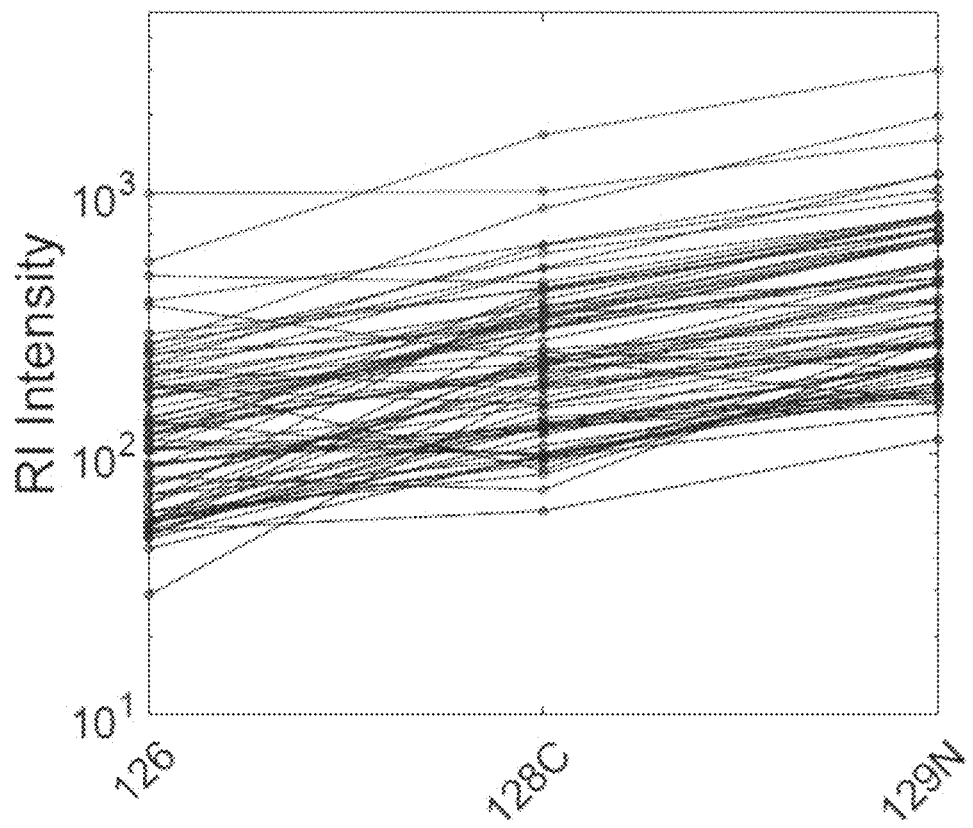
FIG. 5C illustrates the intensities for representative RIs from FIG. 5B are plotted, color coded by their mean intensity. The results show that both lowly (blue) and highly (red) abundant RIs exhibit the expected scaling with the increase of the labeled cell lysate.
Figure 5D:
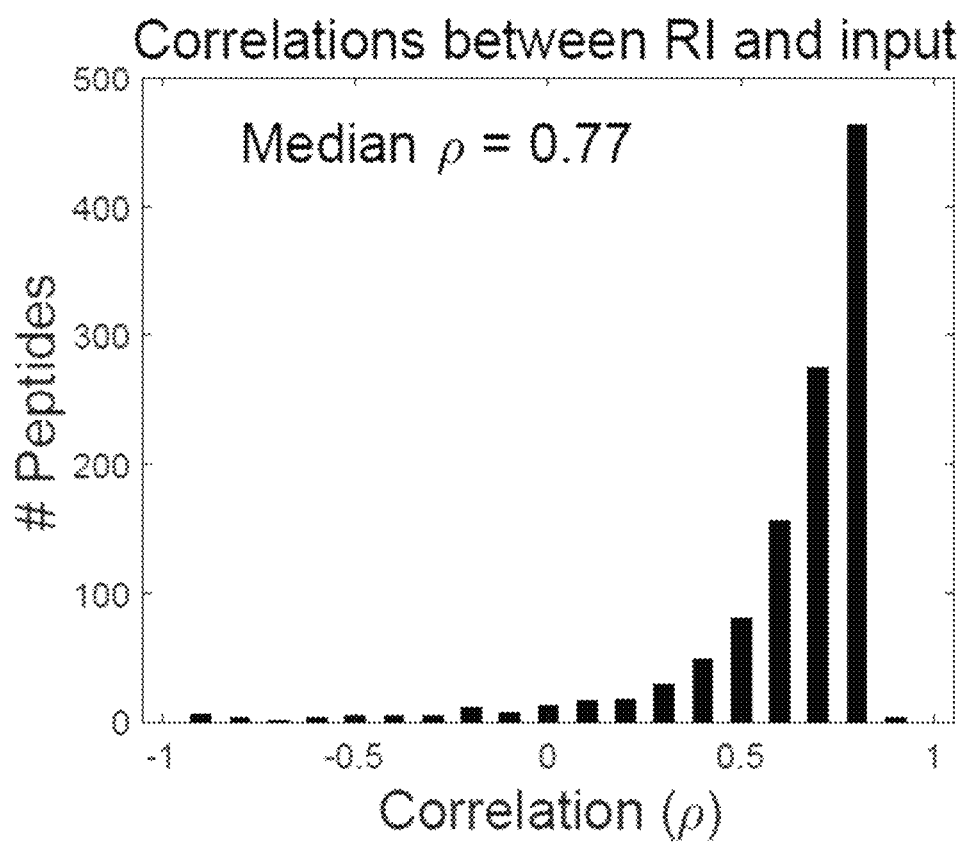
FIG. 5D. For more representative display of the scaling of each peptide with the input amount, the correlation between the sample input amount and the RI intensities for each peptide are computed and the distribution of correlations for all peptides displayed.

Quantification of TMT™-labeled peptides relies on reporter ions (RI) whose levels reflect both peptide abundances and noise contributions, such as coisolation interference and background noise (Sinitcyn P, Rudolph J D, Cox J. Computational methods for understanding mass spectrometry-based shotgun proteomics data. *Annu Rev Biomed Data Sci.* 2018; 1:207-34; Ross P L, Huang Y N, Marchese J N, Williamson B, Parker K, Hattan S, et al. Multiplexed protein quantitation in *Saccharomyces cerevisiae* using amine-reactive isobaric tagging reagents. *Mol Cell Proteomics.* 2004; 3(12):1154-69; Savitski M M, Mathieson T, Zinn N, Sweetman G, Doce C, Becher I, et al. Measuring and managing ratio compression for accurate iTRAQ/TMT quantification. *J Proteome Res.* 2013; 12(8):3586-98). The low protein abundance poses extreme challenges to the signal-to-noise ratio (SNR) and requires careful evaluation even of aspects that are well established and validated in bulk MS measurements. To evaluate the contribution of background noise to single-cell RI quantification, Applicants estimated the signal-to-noise ratio (SNR) (FIGS. 5A-5D). The estimates indicated that RI intensities are proportional to the amount of labeled single-cell proteomes, and very low for channels left empty. These data suggest that the signal measured in single cells exceeds the background noise by 10-fold or more. As an added SNR control for every TMT™ set, SCoPE-MS leaves the 130N channel empty, so that 130N RI reflect both isotopic cross-contamination from channel 131 and the background noise. Applicants further verified that RI intensities in a channel are proportional to the protein amount labeled in that channel for both lowly and highly abundant RIs (FIGS. 5B, 5C and 5D).

To evaluate the ability of SCoPE-MS to distinguish different cell types, Applicants prepared three label-swapped and interlaced TMT™ sets with alternating single Jurkat and U-937 cells, two blood cancer cell lines with average cell diameter of only 11 µm (FIG. 1B). The levels of all 767 proteins quantified in single cells were projected onto their principal components (PC) (Budnik B, Levy E, Harmange G, Slavov N. Mass-spectrometry of single mammalian cells quantifies proteome heterogeneity during cell differentiation. *MassIVE, MSV000082077*. https://massive.ucsd.edu/ProteoSAFe/dataset.jsp?task=4f30cbe81fc440f79bd73f6c27f1816b (2018); Budnik B, Levy E, Harmange G, Slavov N. Mass-spectrometry of single mammalian cells quantifies proteome heterogeneity during cell differentiation. *ProteomeXchange, PXD008985*. http://proteomecentral.proteomexchange.org/cgi/GetDataset?ID=PXD008985 (2018)). The two-dimensional projections of single-cell proteomes are clustered by cell type and in proximity to the projection of bulk samples from the same cell type (FIG. 1C), suggesting that SCoPE-MS can identify cell types based on their proteomes. This cell-type stratification is not driven just by highly abundant proteins since the mean levels of each protein across the single cells was set to one; thus, highly and lowly abundant proteins contributed equally to cell clustering. To further test the quantification of cell-type specific protein expression, Applicants identified proteins whose levels vary less within a cell type than between cell types. Based on a two-sample t-test, Applicants found 107 proteins showing such trends at FDR<2%; see representative distributions for such proteins in FIG. 1D.

Figure 6B:
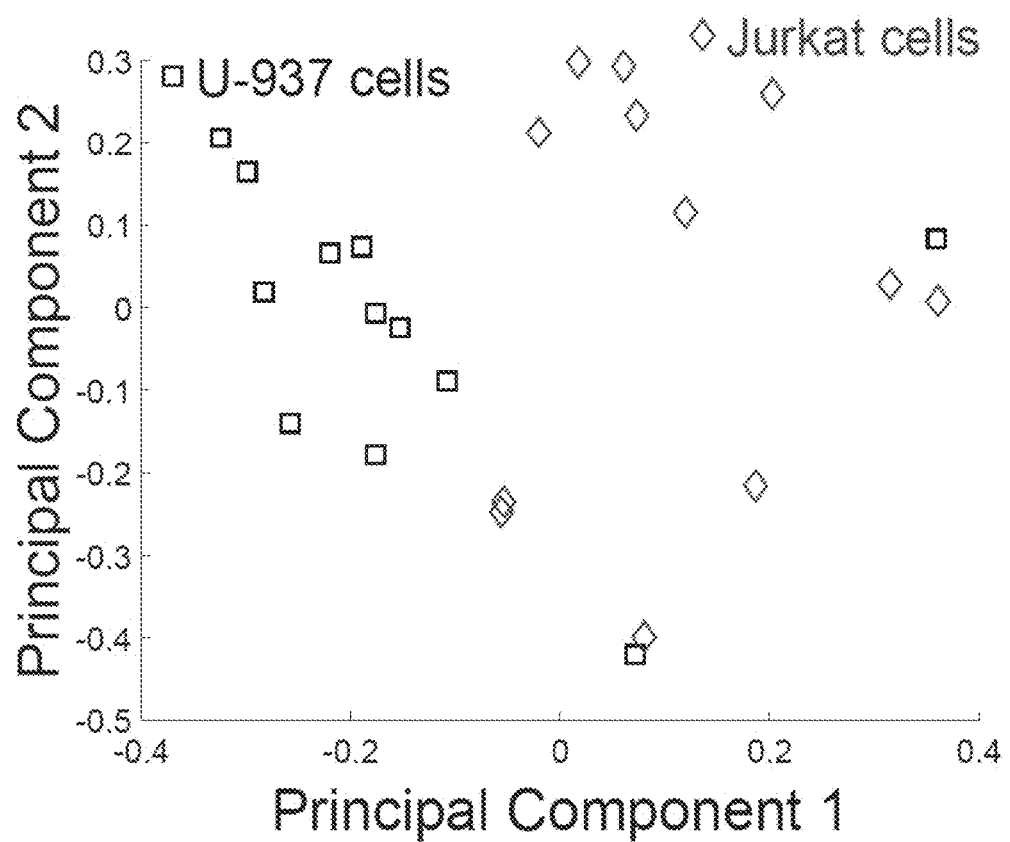
Figure 6C:
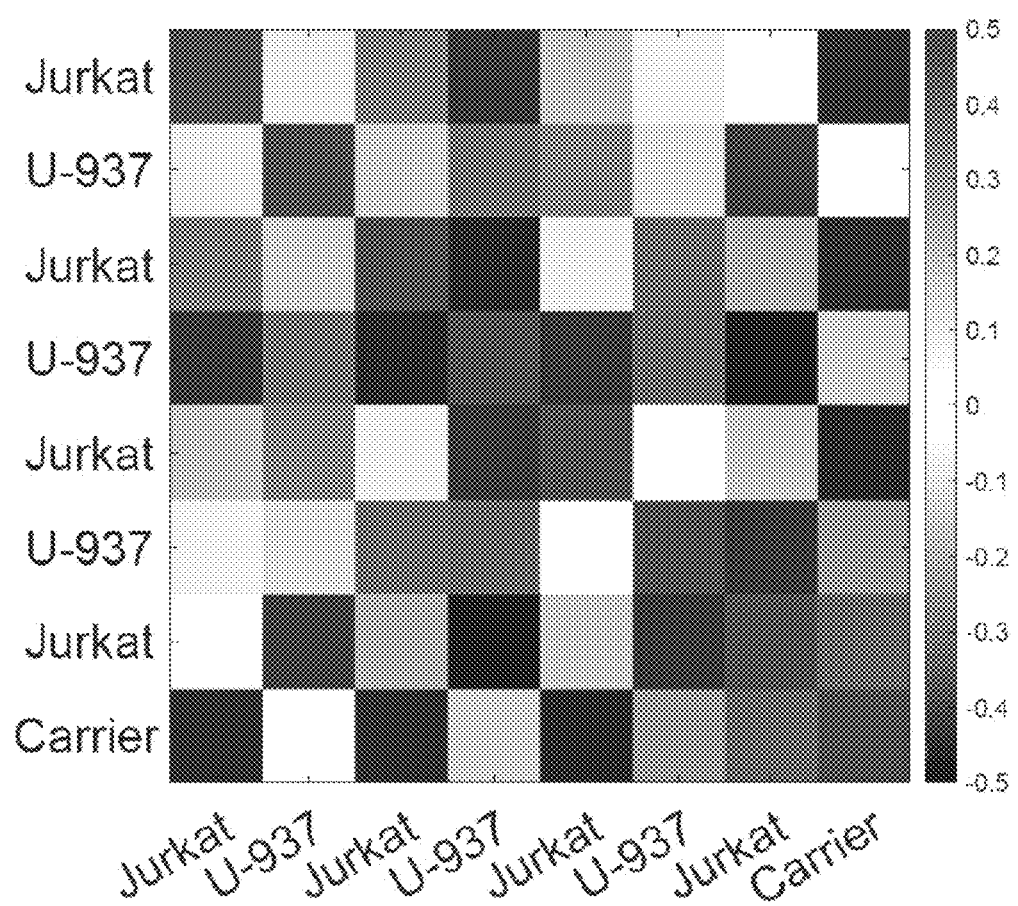

In FIGS. 1A-1E, the cell types of the carrier cells and the single cells are matched. If the proteomes of the carrier cells are significantly different from the proteomes of the single cells, the set of analyzed proteins will change. This is because in shotgun proteomics, peptide ions sent for MS/MS are chosen based on their abundance in the MS1 survey scan. Thus, only peptides with significant abundance in the carrier channel are likely to be sent for MS2 analysis and quantified in the single cells. Therefore, the composition of the carrier channel can affect the sets of peptides quantified across the single cells, i.e., SCoPE-MS samples analyzed by a shotgun method will preferentially provide relative quantification for proteins that are abundant in the carrier cells. However, the relative quantification of a peptide in the single cells, i.e., its RI intensities in the single-cell channels, should not be affected by its abundance in the carrier cells. Applicants tested this expectation with SCoPE-MS sets whose carrier channels contained only U-937 cells, only Jurkat cells, or only HEK-293 cells (FIGS. 6A-6C). These changes of the carrier cells changed the probability of quantifying some proteins; those with lower abundance in the carrier cells, but hundreds of abundant proteins, were quantified across all cells and carrier channels. Since most proteins have comparable (within an order of magnitude) abundances across different cell and tissue types (Wilhelm M, Schlegl J, Hahne H, Gholami A, Lieberenz M, et al. Mass-spectrometry-based draft of the human proteome. *Nature.* 2014; 509:582-7; Franks A, Airoldi E, Slavov N. Post-transcriptional regulation across human tissues. *PLoS Comput Biol.* 2017; 13(5):e1005535), many cell types can provide useful material for the carrier channel. This carrier dependence can be partially mitigated if SCoPE-MS samples are analyzed by targeted, as opposed to shotgun, LC-MS/MS (Specht H, Slavov N. Transformative opportunities for single-cell proteomics. *J Proteome Res.* 2018; 17:2563-916. https://doi.org/10.1021/acs.jproteome.8b00257).

Figure 1E:
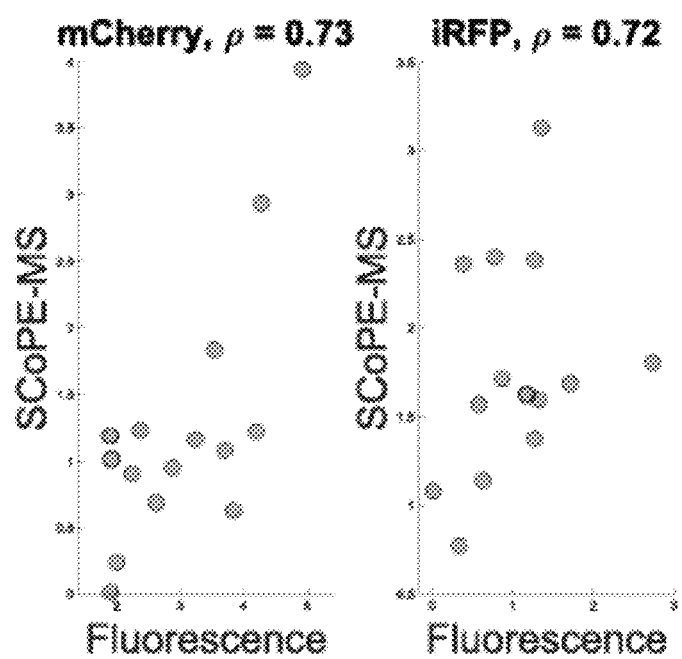

Next, SCoPE-MS quantification was compared against an orthogonal and reliable method for quantifying proteins in single cells, the fluorescence of mCherry and iRFP. To this end, the relative levels of the two proteins were quantified in each single cell by a fluorescence-activated cell sorting (FACS) sorter and by SCoPE-MS (FIG. 1E). For both proteins, the Spearman correlations between the SCoPE-MS and FACS measurements exceed 0.7, suggesting that estimates of relative protein levels by SCoPE-MS are comparable to those derived by FACS.

Figure 7A:
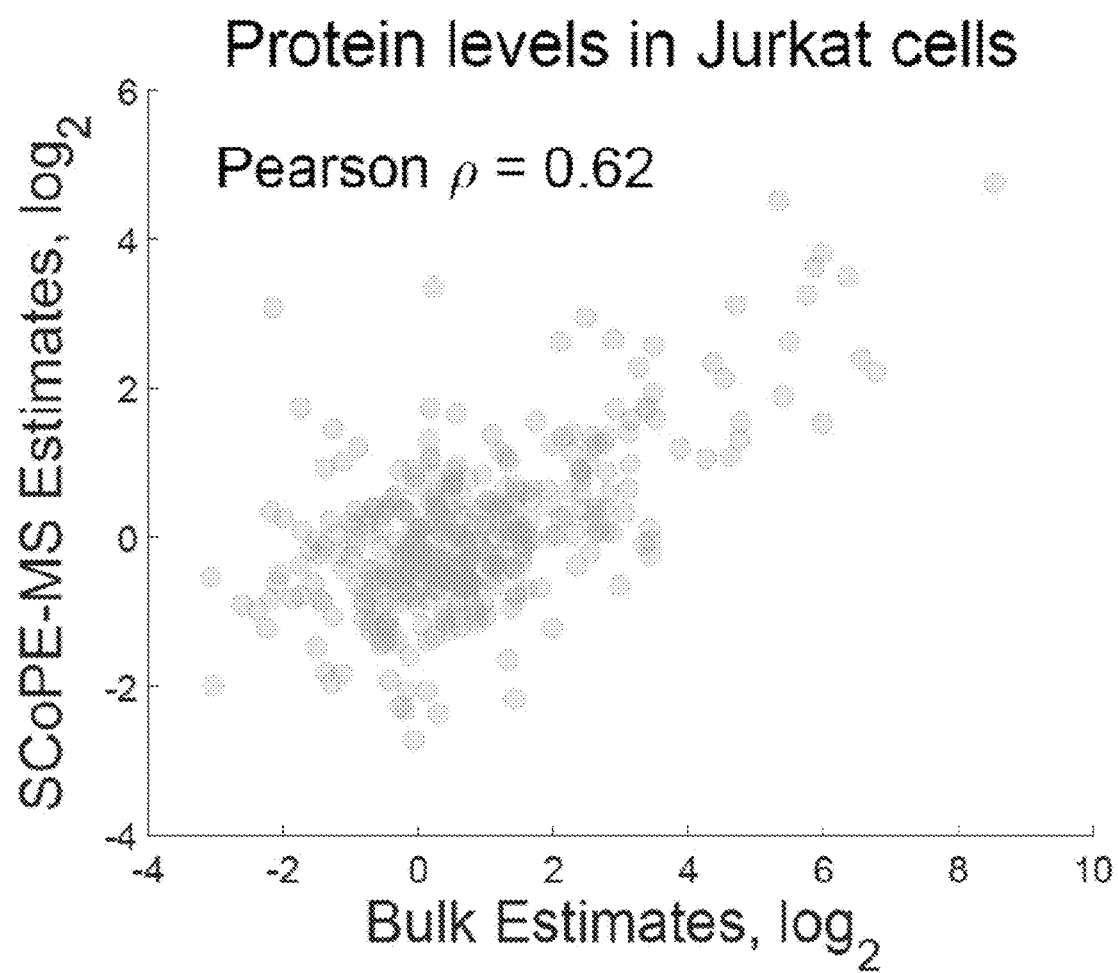
FIGS. 7A-7D illustrate the accuracy of SCoPE-MS quantification.
Figure 7B:
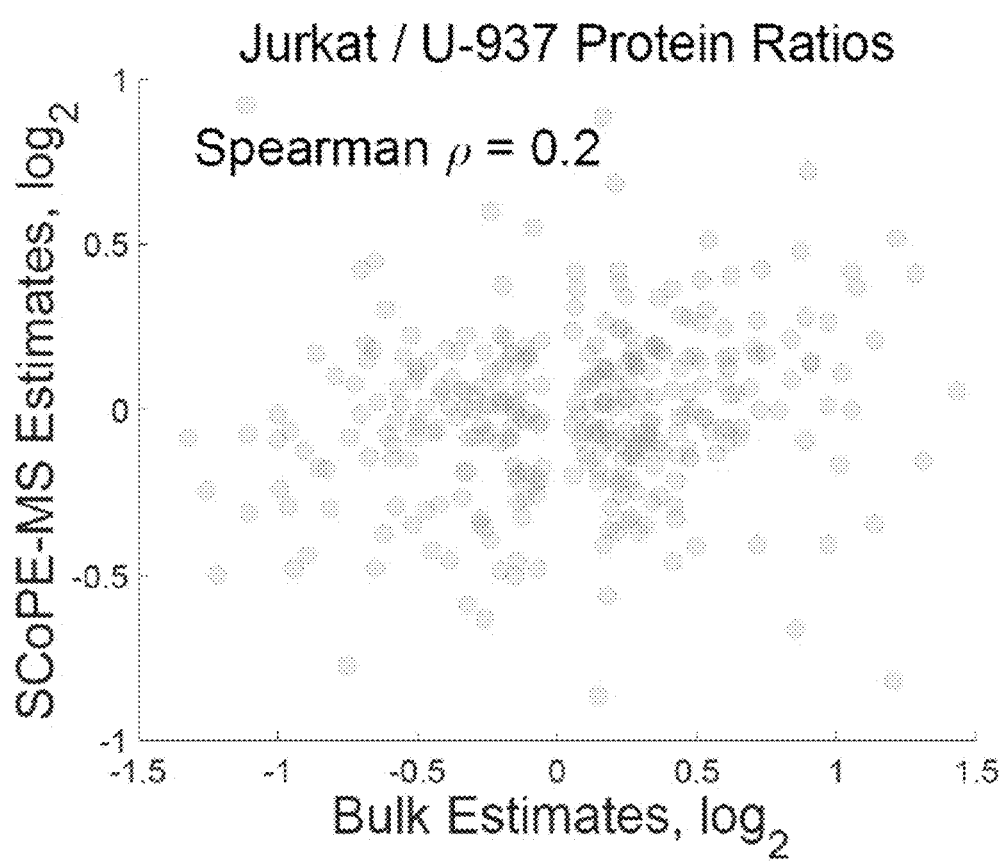
Figure 7C:
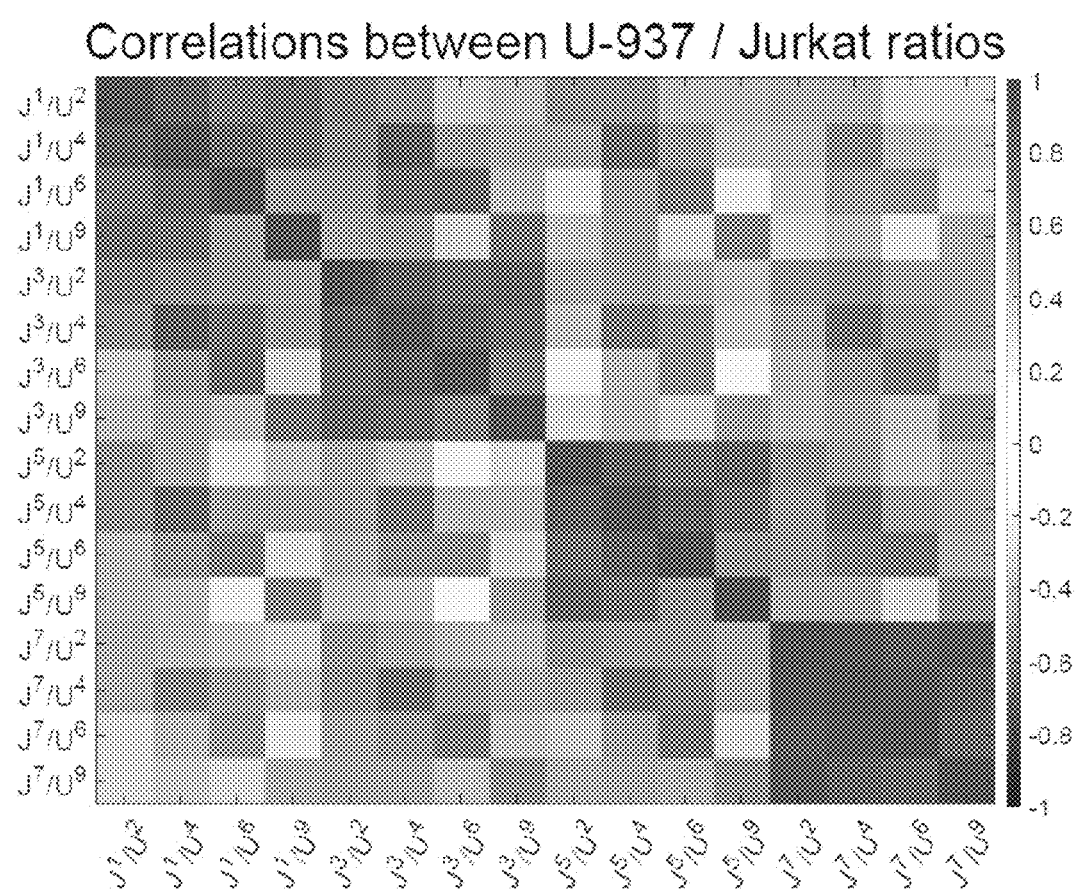
Figure 7D:
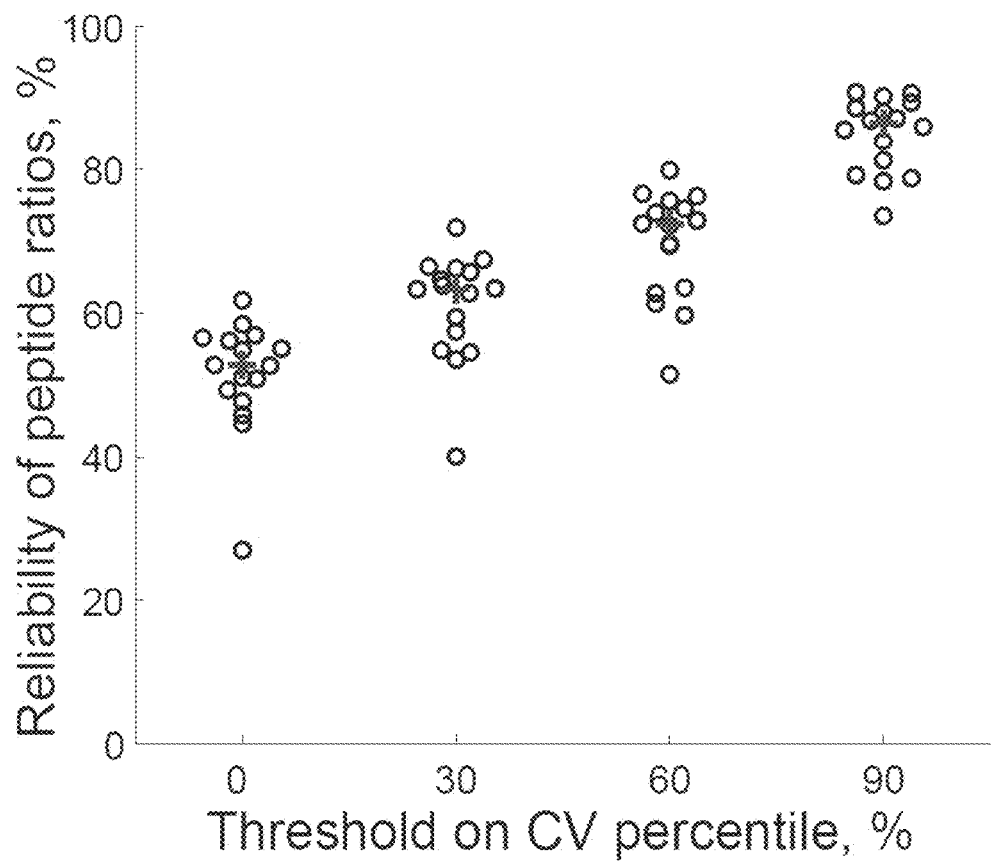

Given the difficulty of measuring extremely low protein levels, SCoPE-MS data was further evaluated by comparing the mean estimates across single cells from FIG. 1B to the corresponding estimates from bulk samples for both integrated precursor-ion-areas (FIG. 7A) and relative (FIG. 7B) protein levels. The correlations between bulk and single-cell estimates indicate good agreement despite the noise inherent in single-cell measurements. The relative quantification by SCoPE-MS was further evaluated by correlating protein fold-changes estimated from different pairs of Jurkat and U-937 cells labeled with different TMT™ tags, demonstrating good consistency of relative quantification for all cells and TMT™ tags (mean correlation ρ>0.5; FIG. 7C). To eliminate the contribution of biological variability and estimate the reproducibility of the MS measurement alone, Applicants split a SCoPE-MS set in two and quantified each half separately. Comparisons of corresponding protein ratios estimated from each half indicated reliability between 60 and 85% depending on the magnitude of the fold changes, FIG. 7D. This reliability is achieved with ⅓ of a single-cell proteome (about 100-150 ng of total protein) (Milo R, Jorgensen P, Moran U, Weber G, Springer M. BioNumbers—the database of key numbers in molecular and cell biology. *Nucleic Acids Res.* 2010; 38: D750-3) and compares favorably to reliability for bulk datasets (Franks A, Airoldi E, Slavov N. Post-transcriptional regulation across human tissues. *PLoS Comput Biol.* 2017; 13(5):e1005535). Taken together, these estimates of quantification accuracy and reproducibility demonstrate that while SCoPE-MS measurements are noisier than bulk MS measurements, they are accurate and reproducible, especially for larger fold-changes.

EXAMPLE 2

Protein Covariation Across Differentiating ES Cells

Figure 2B:
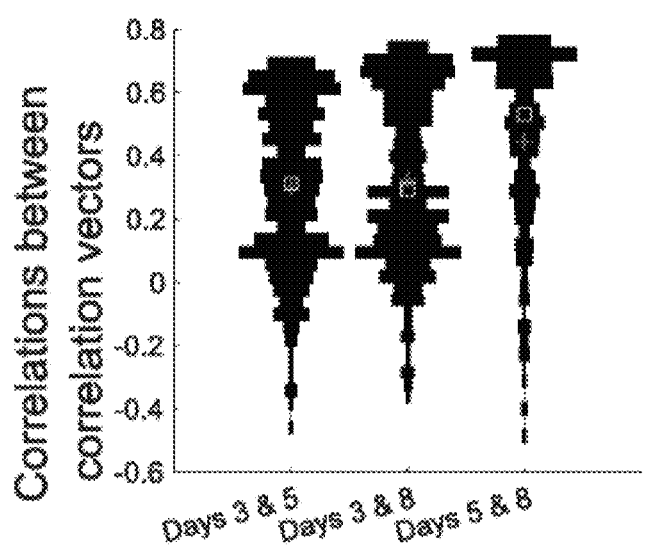

Using SCoPE-MS, single-cell proteome heterogeneity and dynamics during ES cell differentiation was quantified. To initiate differentiation, leukemia inhibitor factor (LIF) was withdrawn from ES cell cultures and transitioned to suspension culture; LIF withdrawal results in complex and highly heterogeneous differentiation of epiblast lineages in embryoid bodies (EB). SCoPE-MS was used to quantify over a thousand proteins at FDR=1%, and their pair-wise correlations (averaging across single cells) in days 3, 5, and 8 after LIF withdrawal (FIG. 2A); data are available at MassIVE (Budnik B, Levy E, Harmange G, Slavov N. Mass-spectrometry of single mammalian cells quantifies proteome heterogeneity during cell differentiation. *MassIVE*, MSV000082077. https://massive.ucsd.edu/ProteoSAFe/dataset.jsp?task=4f30cbe81fc440f79bd73f6c27f1816b (2018)) and at ProteomeXchange (Budnik B, Levy E, Harmange G, Slavov N. Mass-spectrometry of single mammalian cells quantifies proteome heterogeneity during cell differentiation. *ProteomeXchange*, PXD008985. http://proteomecentral.proteomexchange.org/cgi/GetDataset?ID=PXD008985 (2018)). Cells from different days were processed together to minimize batch biases (Hicks S C, Teng M, Irizarry R A. On the widespread and critical impact of systematic bias and batch effects in single-cell RNA-Seq data. *bioRxiv.* 2015; 1:025528). To explore the protein covariation across the differentiating single cells, all pairwise protein-protein correlations were computed and clustered (FIG. 2A). The clustered correlation matrices exhibit clusters of correlation vectors, and evaluation of their similarity across days was sought. To do so, the correlations between corresponding correlation vectors were computed (i.e., the vector of pair-wise correlations of the ith protein from 1 day was correlated to the ith vector of pair-wise correlations from another day); see Slavov N, Dawson K A. Correlation signature of the macroscopic states of the gene regulatory network in cancer. *Proc Natl Acad Sci.* 2009; 106(11):4079-84, for more details. The results shown in FIG. 2B indicate that most correlation vectors from day 3 are positively correlated to the corresponding correlation vectors from days 5 and 8. The corresponding correlation vectors from days 5 and 8 are substantially more similar to each other (FIG. 2B), reflecting the more advanced differentiation changes on those days.

Figure 2C:
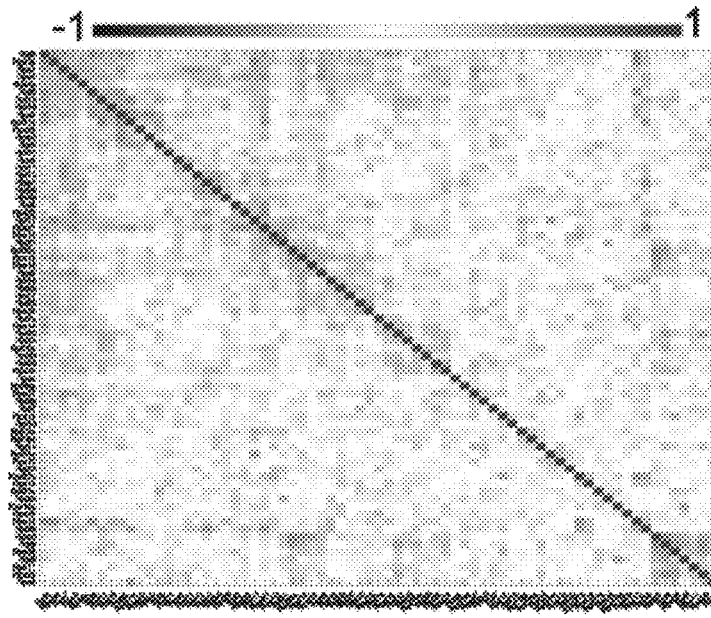
Figure 2D:
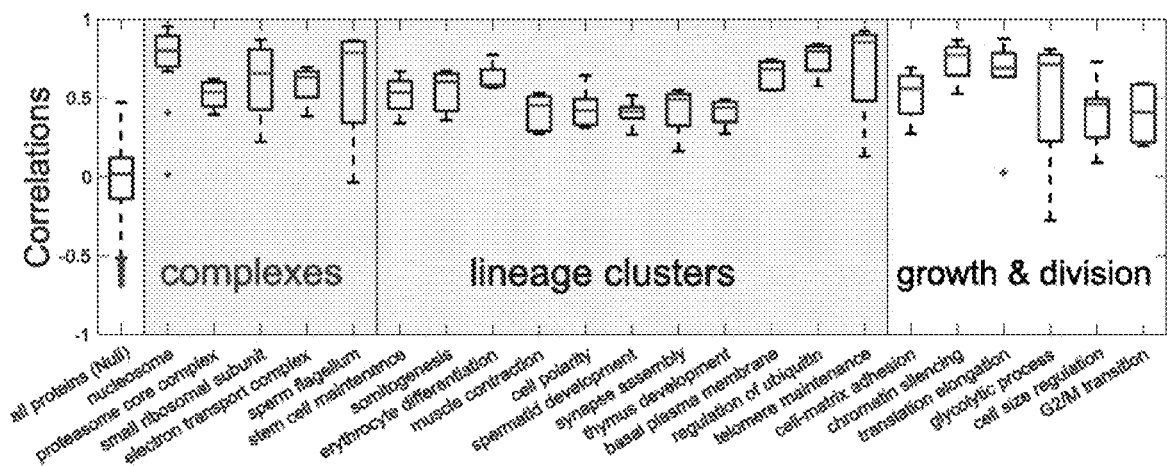

As cells differentiated and became more distinct from each other, so did the clusters of correlation vectors (FIG. 2A). Gene set enrichment analysis of the clusters indicated that functionally related proteins are over-represented. As expected, proteins forming protein complexes are strongly correlated to each other. For example, most ribosomal proteins (RPs) correlate positively to each other (FIG. 2C). A small subset of RPs covaries as a distinct cluster in the bottom right corner of FIG. 2C, and this might reflect ribosome specialization, i.e., variation among the RP stoichiometry across the cell lineages that contributes to specialized translation functions (Mauro V P, Edelman G M. The ribosome filter hypothesis. *Proc Natl Acad Sci.* 2002; 99(19):12031-6; Preiss T. All ribosomes are created equal. Really? *Trends Biochem Sci.* 2015; 41(2); Emmott E P, Jovanovic M, Slavov N. Ribosome stoichiometry: from form to function. *Peer J Preprints.* 2018; 6:e26991v1). Alternatively, the cluster might reflect extra-ribosomal functions (Wool I G. Extraribosomal functions of ribosomal proteins. *Trends Biochem Sci.* 1996; 21(5):164-5), and these possibilities need to be evaluated more directly with isolated ribosomes (Emmott E P, Jovanovic M, Slavov N. Ribosome stoichiometry: from form to function. *Peer J Preprints.* 2018; 6:e26991v1; Slavov N, Semrau S, Airoldi E, Budnik B, van Oudenaarden A. Differential stoichiometry among core ribosomal proteins. *Cell Rep* 2015; 13:865-873). The subunits from other complexes, e.g., the proteasome and the electron transport complex, also covary as indicated by the positive correlations within these complexes (FIG. 2D). A similar pattern of covariation is observed for sets of lineage-specific proteins, including proteins with functions specific to neuronal, blood, and muscle cells (FIG. 2D). Proteins functioning in mRNA translation, metabolism, and cell division also covary, most likely reflecting differences in cell growth and division among the single cells as they differentiate and slow their growth rate.

EXAMPLE 3

Principal Component Analysis of Differentiating ES Cells

Figure 3A:
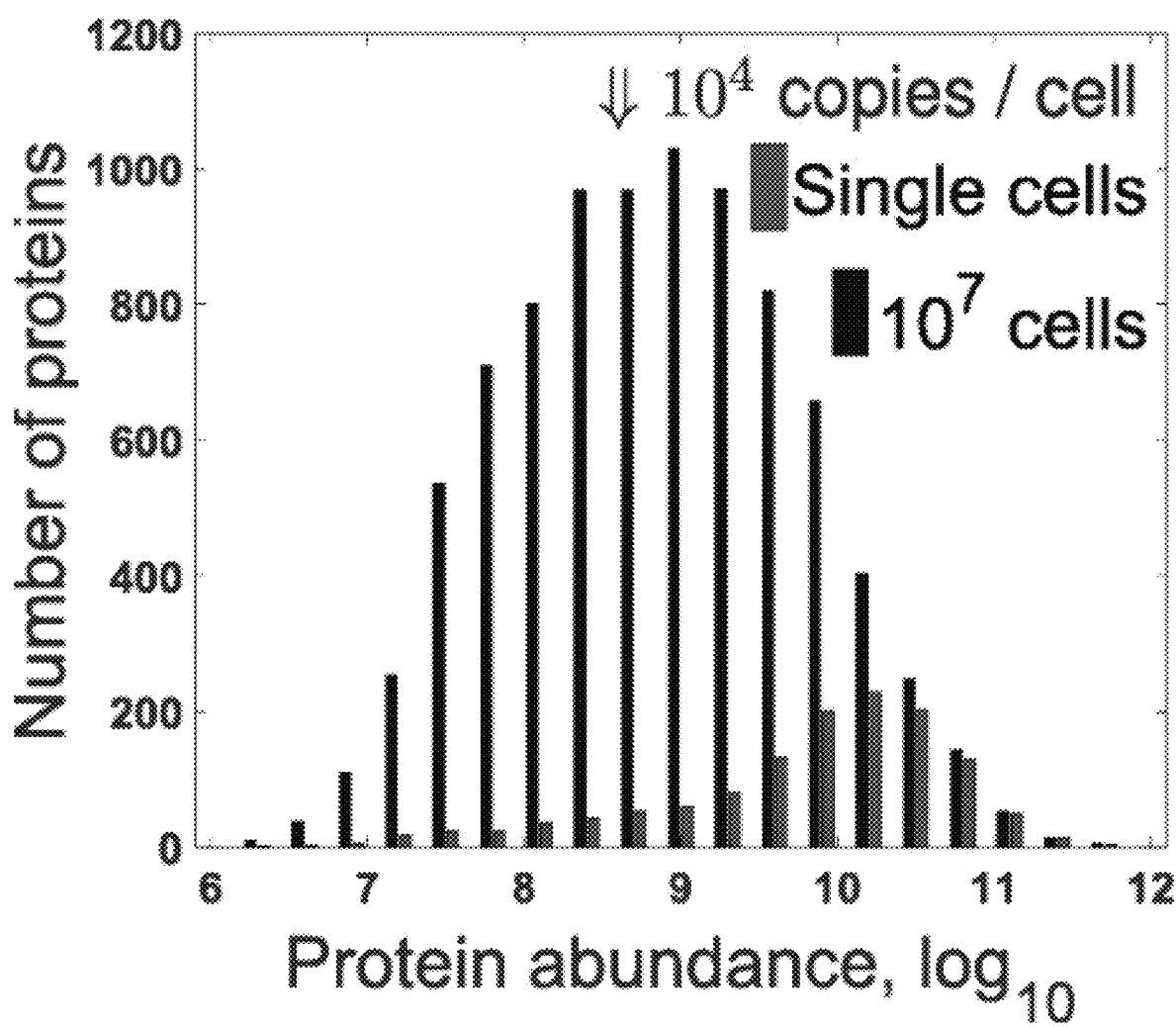
FIGS. 3A-3E provide example experimental data showing the principal component analysis of differentiating ES cells.

To estimate the abundance of proteins quantified in single cells, the distributions of abundances for over 10,000 proteins quantified in a bulk sample were compared (van den Berg P R, Budnik B, Slavov N, Semrau S. Dynamic post-transcriptional regulation during embryonic stem cell differentiation. *bioRxiv.* 2017; 1) and for the subset of these proteins quantified in SCoPE-MS sets (FIG. 3A). Most of the proteins quantified in the single cells tend to be abundant, mostly above the median of the bulk sets, which corresponds to about 50,000 copies per cell (Milo R, Jorgensen P, Moran U, Weber G, Springer M. BioNumbers—the database of key numbers in molecular and cell biology. *Nucleic Acids Res.* 2010; 38: D750-3). This is expected given that shotgun MS was used, but combining improvements in SCoPE-MS and targeted MS approaches will enable quantifying substantially less-abundant proteins (Specht H, Slavov N. Transformative opportunities for single-cell proteomics. *J Proteome Res.* 2018; 17:2563-916).

Figure 3B:
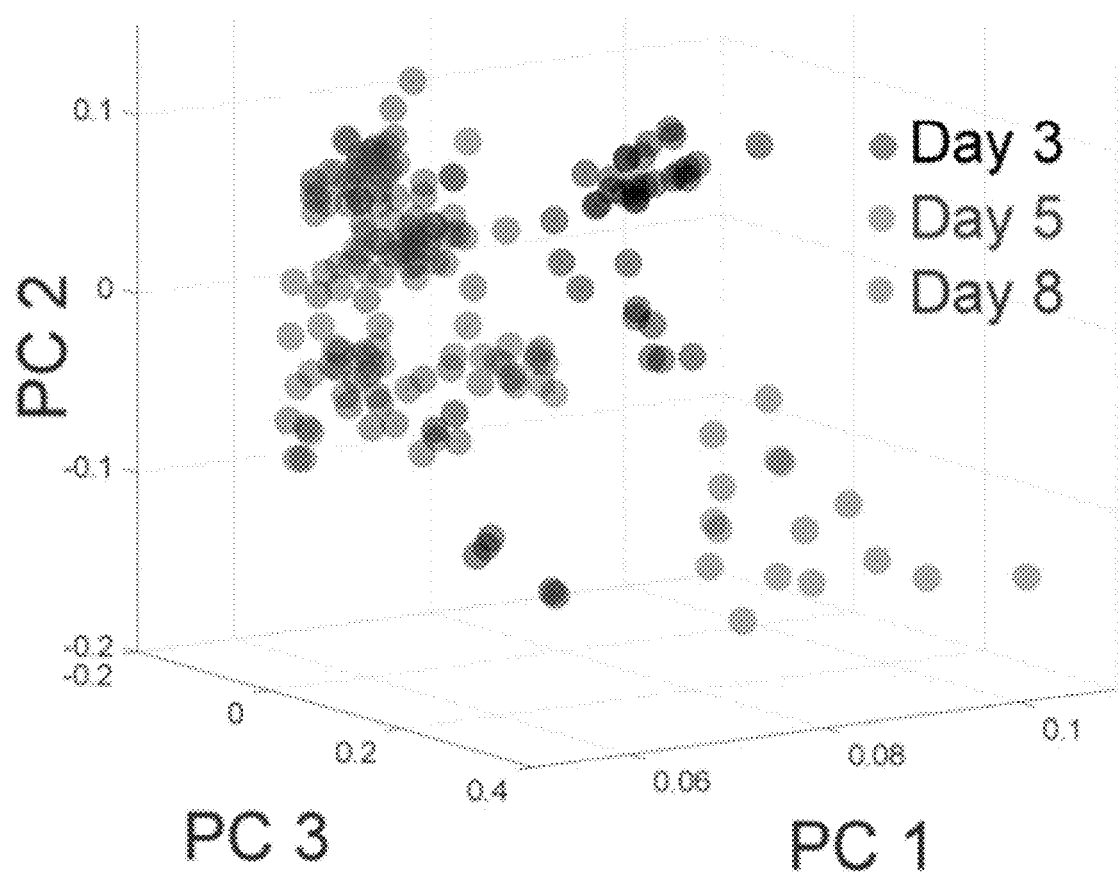
Figures 3C, 3D:
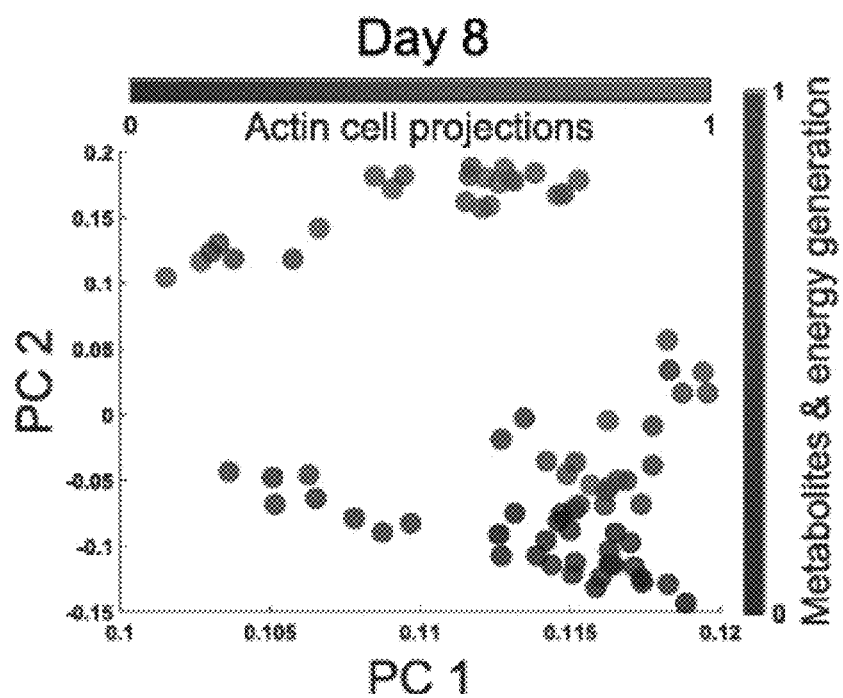

Next, classification of single cells using all proteins identified and quantified by SCoPE-MS in single ES and EB cells was sought. The proteomes of single cells from all days (190 cells) were projected onto their PCs (FIG. 3B). The cells partially cluster by time of differentiation; indeed, the loadings of the first three PCs correlate to the days post LIF withdrawal (FIG. 3C). However, the clustering by time of differentiation is incomplete, at least in part because of asynchrony in the differentiation (Klein A M, Mazutis L, Akartuna I, Tallapragada N, Veres A, Li V, et al. Droplet barcoding for single-cell transcriptomics applied to embryonic stem cells. *Cell*. 2015; 161(5):1187-201). Similar to single-cell RNA-seq, SCoPE-MS did not quantify each gene in each cell. The number of genes with missing quantification varies from cell to cell for single-cell RNAseq methods and this variation is one of the primary sources of variance in the estimated RNA levels (Hicks S C, Teng M, Irizarry R A. On the widespread and critical impact of systematic bias and batch effects in single-cell RNA-Seq data. *bioRxiv*. 2015; 1:025528). To test if this is the case for SCoPE-MS, Applicants computed the fraction of proteins with missing data for each cell and correlated that fraction to the PCs. The correlations shown in FIG. 3C suggest that the degree of missing data contributes to the variance but less than what has been described for some RNA datasets (Hicks S C, Teng M, Irizarry R A. On the widespread and critical impact of systematic bias and batch effects in single-cell RNA-Seq data. *bioRxiv*. 2015; 1:025528). The degree of missing data can be substantially reduced by using targeted MS (Specht H, Slavov N. Transformative opportunities for single-cell proteomics. *J Proteome Res*. 2018; 17:2563-916) or its influence mitigated by simply filtering out the proteins with the most missing data or perhaps by more sophisticated normalization approaches. Since the mechanisms generating missing data differ between RNAseq and SCoPE-MS, it is expected that the effects of missing data and their management will be different as well.

Figure 3E:
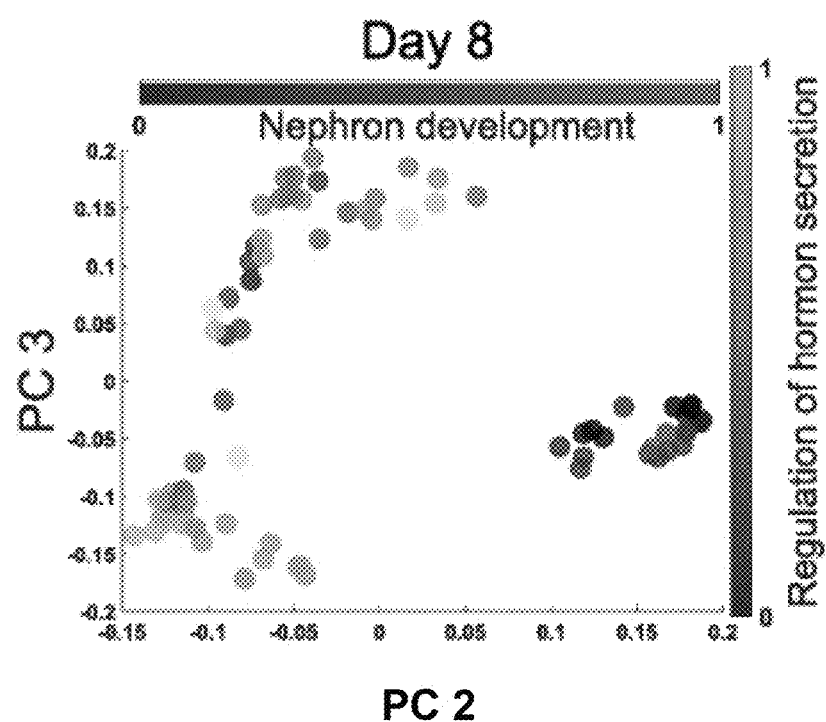

The clusters of lineage-specific proteins in FIGS. 2A-2D suggest that proteomes of distinct cell lineages have been quantified; thus, identification of cell clusters was attempted by projecting the proteomes of cells from day 8 onto their PCs and identifying sets of proteins that are concertedly regulated in each cluster (FIGS. 3D and 3E). The projection resulted in clusters of cells, whose identity is suggested by the dominant proteins in the singular vectors. Biological functions over-represented were identified (Franks A, Airoldi E, Slavov N. Post-transcriptional regulation across human tissues*PLoS Comput Biol*. 2017; 13(5):e1005535) within the distribution of PC loadings and color-coded each cell based on the average levels of proteins annotated to these functions. These results show that SCoPE-MS data can meaningfully classify cell identity for cells from complex and highly heterogeneous populations.

EXAMPLE 4

Coordinated mRNA and Protein Covariation in Single Cells

Figure 4A:
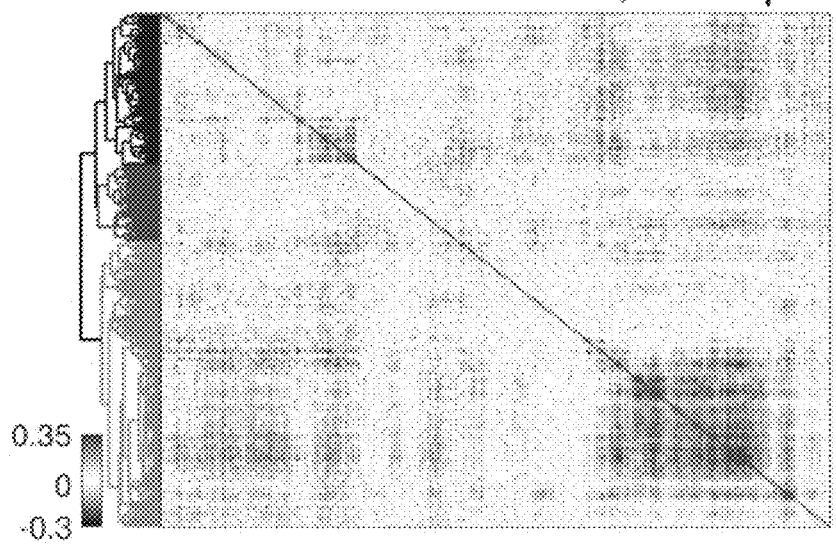
FIGS. 4A-4E provide example experimental data showing coordinated mRNA and protein covariation in differentiating ES cells.
Figure 4B:
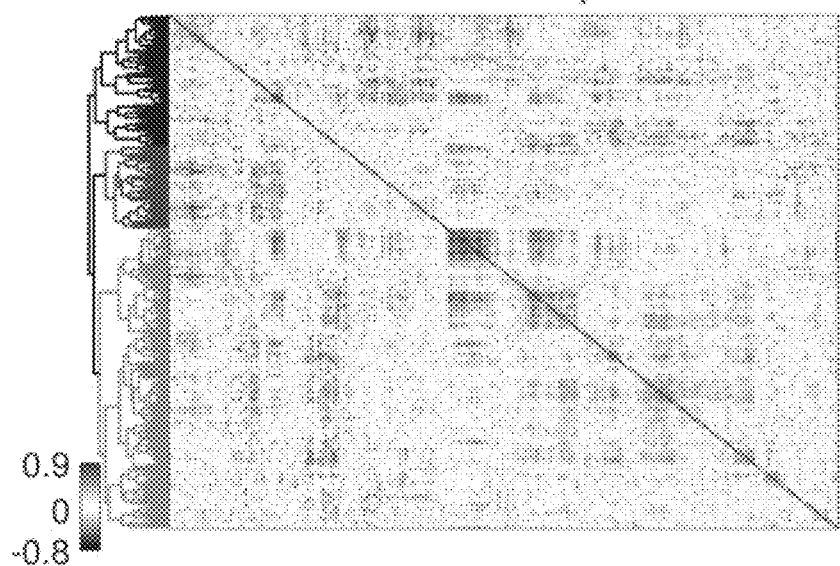
Figure 4C:
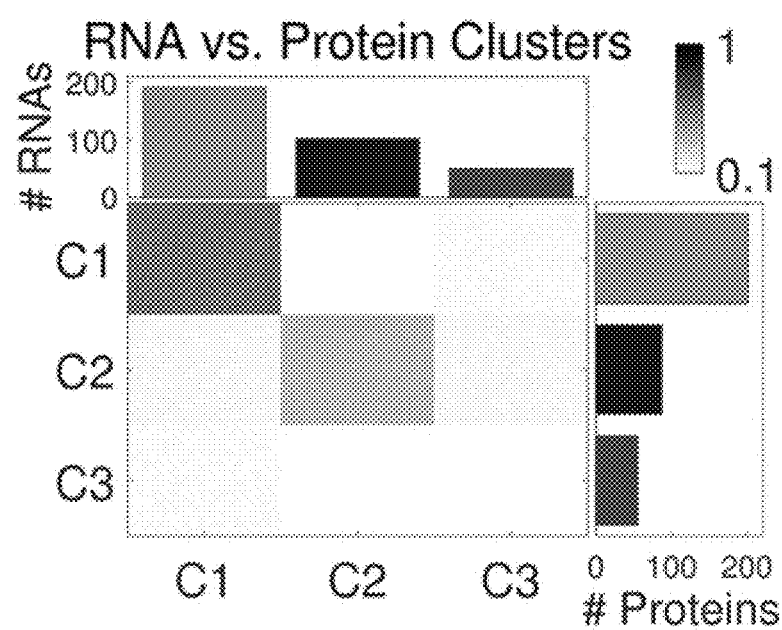
Figure 4D:
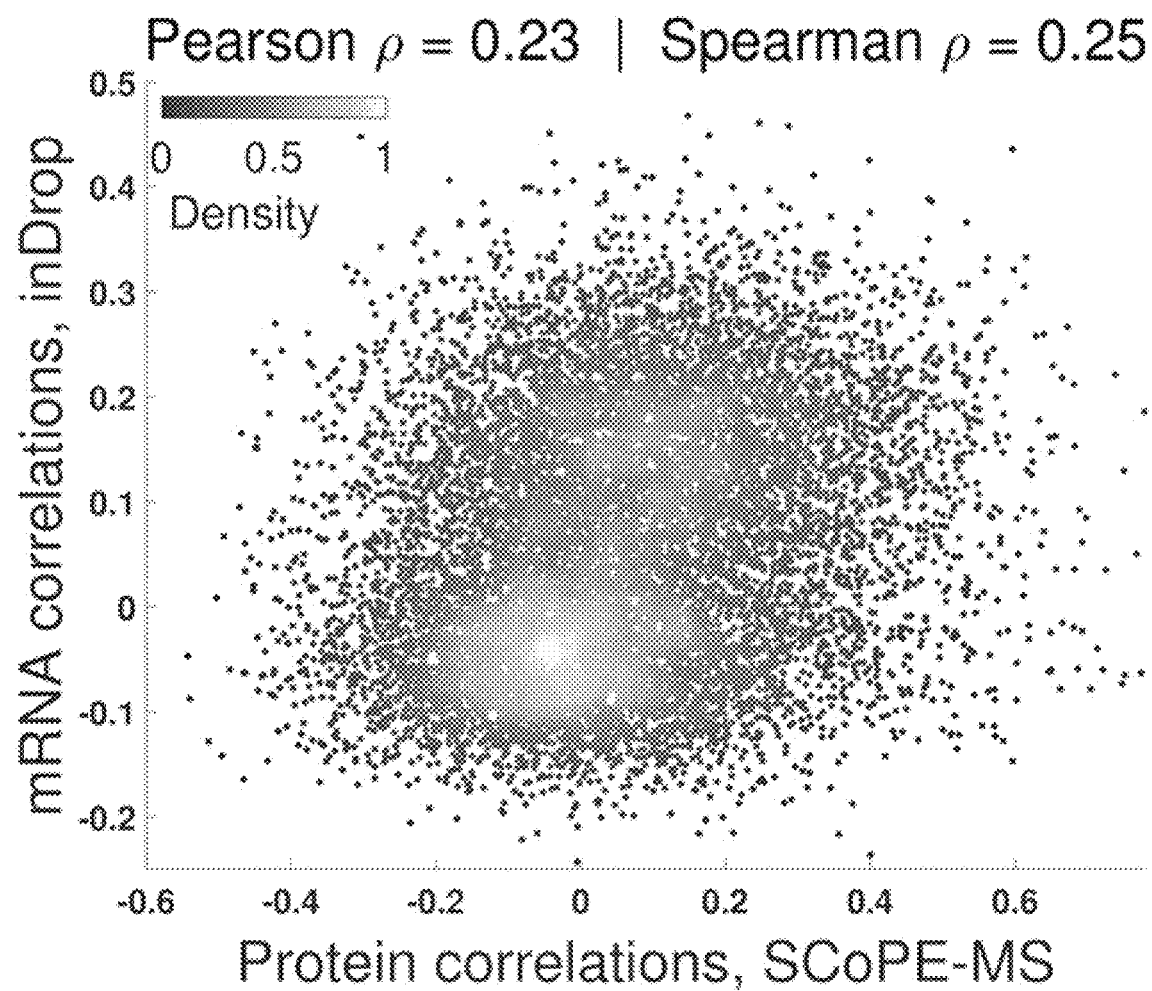

Klein et al. (Droplet barcoding for single-cell transcriptomics applied to embryonic stem cells. *Cell*. 2015; 161(5): 1187-201) recently quantified mRNA heterogeneity during ES differentiation, and their inDrop data was used to simultaneously analyze mRNA and protein covariation and to directly test whether genes co-expressed at the mRNA level are also co-expressed at the protein level. To this end, all pairwise correlations between RNAs (FIG. 4A) and proteins (FIG. 4B) for all genes quantified at both levels in cells undergoing differentiation for 7 and 8 days were computed. Clustering hierarchically the correlation matrices results in three clusters of genes. To compare these clusters, the pairwise Jaccard coefficients were computed, defined as the number of genes present in both classes divided by the number of genes present in either class, i.e., intersection/ union. The results (FIG. 4C) indicate that the largest (green) cluster is 55% identical and the medium (blue) cluster is 33% identical. This cluster stability is also reflected in a positive correlation between corresponding mRNA and protein correlations (FIG. 4D). The magnitude of this correlation is comparable to protein-mRNA correlations from bulk datasets (Wilhelm M, Schlegl J, Hahne H, Gholami A, Lieberenz M, et al. Mass-spectrometry-based draft of the human proteome. *Nature*. 2014; 509:582-7; Franks A, Airoldi E, Slavov N. Post-transcriptional regulation across human tissues. *PLoS Comput Biol*. 2017; 13(5): e1005535) and testifies to the quantitative accuracy of both inDrop and SCoPE-MS.

Figure 4E:
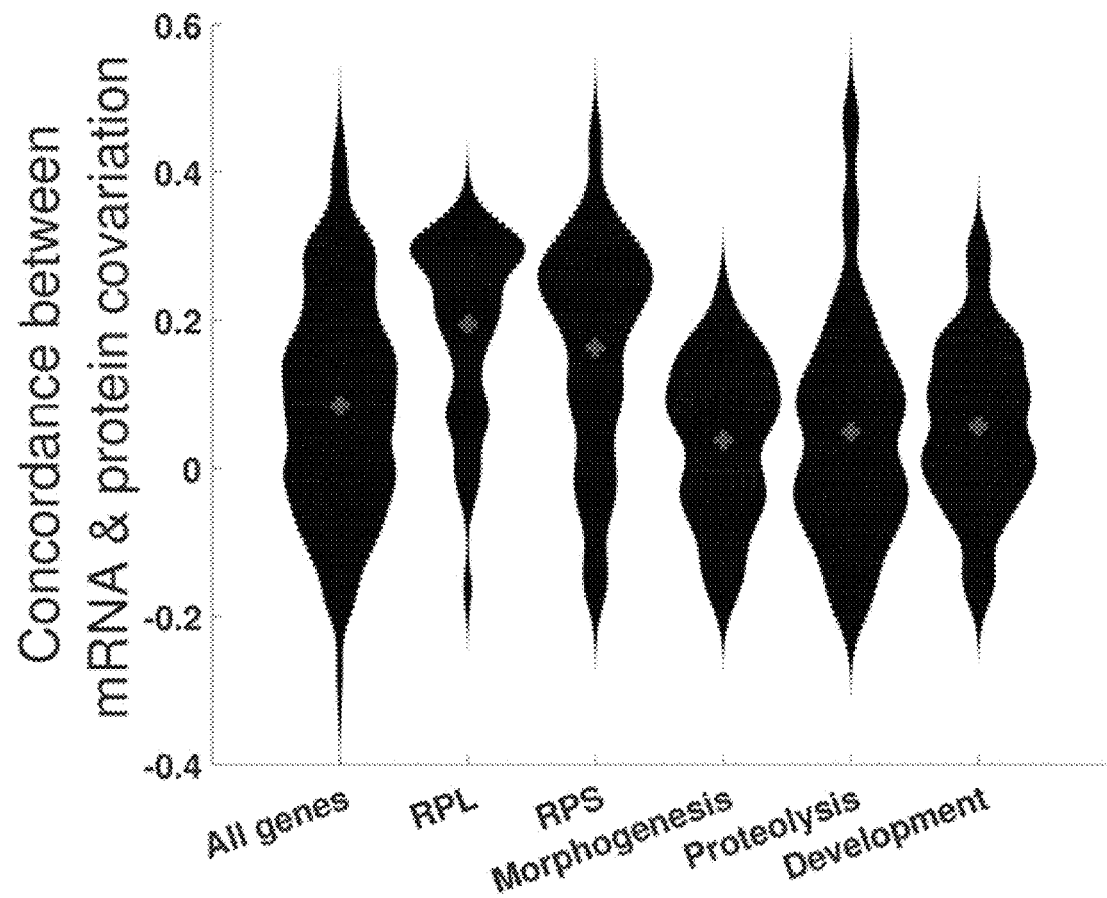

Having established a good overall concordance between mRNA and protein covariation, it was next explored whether and how much this concordance varies between genes with different biological functions. The covariation concordance of a gene was estimated as the similarity of its mRNA and protein correlations, using as a similarity metric the correlation between the corresponding correlation vectors as Applicants have done previously (Slavov N, Dawson K A. Correlation signature of the macroscopic states of the gene regulatory network in cancer. *Proc Natl Acad Sci*. 2009; 106(11):4079-84; Silverman S J, Petti A A, Slavov N, Parsons L, Briehof R, Thiberge S Y, et al. Metabolic cycling in single yeast cells from unsynchronized steady-state populations limited on glucose or phosphate. *Proc Natl Acad Sci*. 2010; 107(15):6946-51). The median concordance of ribosomal proteins of both the 60S (RPL) and 40S (RPS) is significantly higher than for all genes (FIG. 4E). This result indicates that RPL and RPS genes have significantly ($p<10^{-20}$) more similar gene-gene correlations at the mRNA and the protein levels than the other quantified genes. In contrast to RPs, genes functioning in tissue morphogenesis, proteolysis, and development have significantly ($p<10^{-3}$) lower concordance at the mRNA and protein levels than all genes (FIG. 4E). This difference may reflect both differences in the degree of post-transcriptional regulation or measurement noise for the different sets of genes (Franks A, Airoldi E, Slavov N. Post-transcriptional regulation across human tissues. *PLoS Comput Biol*. 2017; 13(5):e1005535).

EXAMPLE 5

Method of Lysing Cells in Pure Water

A method for lysing cells in pure water that is high-throughput, inexpensive, easily-automated, compatible with small lysis volumes and only uses common, inexpensive, commercial laboratory equipment was sought. The LCMS/ MS compatibility of lysis methods developed for other applications was evaluated and it was found that protein extraction was rather incomplete compared to methods validated for LC-MS/MS that use detergents and chaotropic chemicals. Among these methods, freeze-thaw cycles in pure water showed the most promise, and Applicants iteratively optimized it to increase its robustness and the efficiency of delivering peptides for LC-MS/MS analysis while preserving the physiological state of the analyzed cells. These efforts culminated in mPOP, a method that lyses culture-grown mammalian cells by a freeze-heat cycle (−80° C. to 90° C.) in small droplets of pure water, as illustrated in FIG. 9A.

For bottom-up proteomics, the cell lysate is then digested in 10 ng/μL of the protease trypsin. This simple procedure allowed the design of a proteomics sample preparation using only a MS-compatible digestion buffer (Triethylammonium bicarbonate, pH 8.0), trypsin, and formic acid. Crucially, mPOP allows minimizing volumes, which reduces sample losses and reagents used. It also allows sample preparation in 96/384 well-plates, which enabled simultaneous processing of many samples in parallel. Furthermore, the obviation of cleanup allowed for the easy automation of mPOP sample preparation with inexpensive PCR thermocyclers and liquid dispensers.

EXAMPLE 6

Evaluating the Completeness of Lysis and Protein Extraction

Applicants sought to directly compare the lysis efficiency of mPOP to that of standard 6M urea lysis using the experimental design in FIG. 1b. Urea was chosen because it is a widely-used lysis method for LC-MS/MS that compares favorably to other methods and its accessibility facilitates replication (Huang, E. L. et al. SNaPP: simplified nanoproteomics platform for reproducible global proteomic analysis of nanogram protein quantities. *Endocrinology* 157, 1307-1314 (2016)). Applicants lysed samples of FACS sorted U-937 cells with either mPOP or urea, FIG. 9B. Each sample was comprised of 10,000 cells having either light SILAC or heavy SILAC label. Samples of 10,000 cells were chosen to provide enough proteins so that clean-up losses by StageTip (Rappsilber, J., Mann, M. & Ishihama, Y. Protocol for micro-purification, enrichment, prefractionation and storage of peptides for proteomics using StageTips.en. *Nature Protocols* 2, 1896-1906. ISSN: 1754-2189, 1750-2799 (August 2007)) (which is required by urea lysis) are affordable and lysis efficiency can be evaluated independently from cleanup-losses. Light cells lysed by urea were mixed with heavy cells lysed by mPOP, FIG. 9B. To control for possible biases, Applicants also performed a label swap in which heavy cells lysed by urea were mixed with light cells lysed by mPOP. The mixtures of light and heavy cell-lysates were cleaned-up by StageTip to remove urea. This design incurred unnecessary clean-up losses from the mPOP lysates (since they do not need to be cleaned), but it allowed us to evaluate the lysis efficiency of mPOP to that of 6M urea independently of cleanup losses since the cleanup losses in this experiment occur after the mixing and are identical for both lysis methods. These samples were analyzed by LC-MS/MS, and the relative abundance of each peptide between the heavy and light lysates quantified with its SILAC ratio. The distributions of SILAC ratios for all peptides (FIG. 9C) indicate that most peptides have higher abundances in samples lysed by mPOP, suggesting that mPOP allows delivering peptides to MS analysis at least as efficiently as urea lysis. To examine potential bias in the extraction of proteins, Applicants analyzed the distribution of SILAC ratios partitioned by cellular compartment, including both compartments expected to be difficult and easy to lyse, FIG. 9C. The results indicate that mPOP lysis outperforms urea lysis for proteins residing in the cytosol, mitochondrion, nucleus, and the cell membrane. Indeed, no gene sets with greater than two unique proteins favor urea lysis over mPOP.

EXAMPLE 7

Evaluating Quantification Accuracy

Having established that mPOP lyses cells efficiently, Applicants sought to evaluate the reproducibility of relative protein quantification between mPOP and urea lysis using the experimental design outlined in FIG. 9E. FACS-sorted samples of 10,000 heavy SILAC Jurkat cells were combined with 10,000 light SILAC U937 cells in the same tube. These sample were lysed with either mPOP or urea. All cell-lysates were digested by trypsin (urea-containing samples after dilution to <1M) for either 3 or 18 hours. Then, trypsin was quenched with 1% by volume formic acid, FIG. 9E. To remove the urea, samples were cleaned-up by StageTip. All samples were analyzed on a Orbitrap Lumos, and the relative protein levels between Jurkat and U937 cells estimated with the corresponding SILAC ratios computed by MaxQuant. To compare the consistency of quantification within and between lysis methods, Applicants compared the pairwise correlations between the SILAC ratios of all samples, FIGS. 9E and 9F. The correlations ranged between 0.78 and 1, indicating excellent reproducibility both within and across lysis methods. Furthermore, Applicants found the mean coefficient of variation of peptide SILAC ratios to be <10% for both mPOP and urea replicates, FIGS. 12A-12B. Since Applicants did not mix the samples lysed by mPOP and by urea, Applicants could compare proteome coverage between the two methods (FIG. 9H). The number of proteins identified and quantified using urea lysis is comparable to that from similar label-free studies (Dhabaria, A., Cifani, P., Reed, C., Steen, H. & Kentsis, A. A high-efficiency cellular extraction system for biological proteomics. *Journal of proteome research* 14, 3403-3408 (2015)). Almost all of these proteins were identified and quantified by mPOP as well (2,438 proteins), but mPOP samples contained an additional 953 proteins (FIG. 9H).

EXAMPLE 8

Combining mPOP and SCoPE-MS

The results with 10,000 cells demonstrate that mPOP performs as well or better than urea lysis in terms of (i) efficiency of proteome extraction (FIGS. 9A-9D), (ii) quantification accuracy (FIGS. 9E-9G), and (iii) depth of proteome coverage (FIG. 9F). Next, Applicants turn to the key advantages of mPOP, namely parallel and automated preparation of samples that are too small to be cleaned-up without significant losses. To further reduce losses during nano liquid chromatography (nLC), enhance sequence identification, and increase throughput, Applicants used the carrier design that Applicants introduced with SCoPE-MS (Budnik, B., Levy, E., Harmange, G. & Slavov, N. Mass-spectrometry of single mammalian cells quantifies proteome heterogeneity during cell differentiation. *bioRxiv*1, DOI:10.1101/102681 (2017)) but lysed the cells with mPOP instead by FAS. Introducing mPOP allowed reduction in lysis volumes 10-fold, from 10 μl to 1 μl, to reduce the cost of consumables and equipment over 100-fold, and to increase throughput of sample preparation over 100-fold by preparing many samples in parallel.

EXAMPLE 9

Benchmarking Instrument Noise with SCoPE-MS Design

Figure 10A:
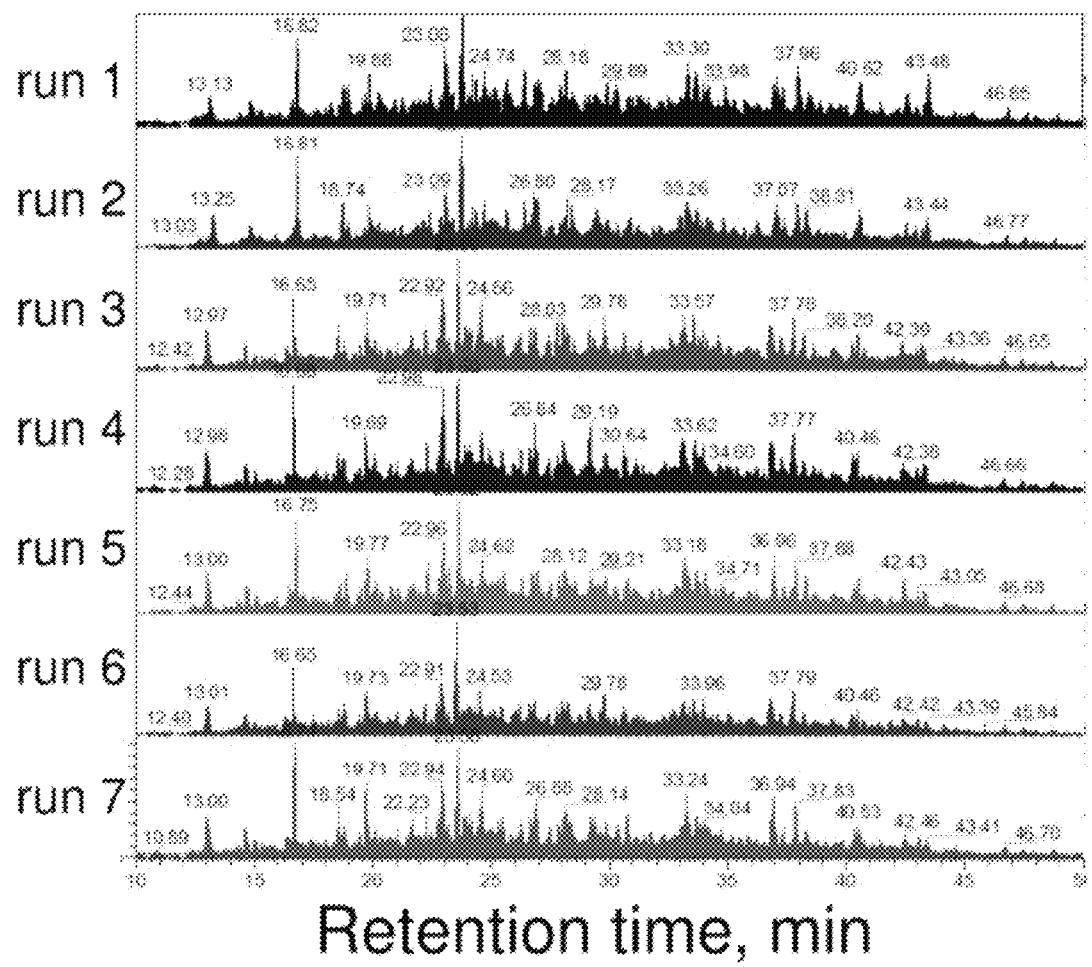
FIGS. 10A-10F show example results of experiments for benchmarking diluted SCoPE-MS sets prepared by mPOP.
Figure 10B:
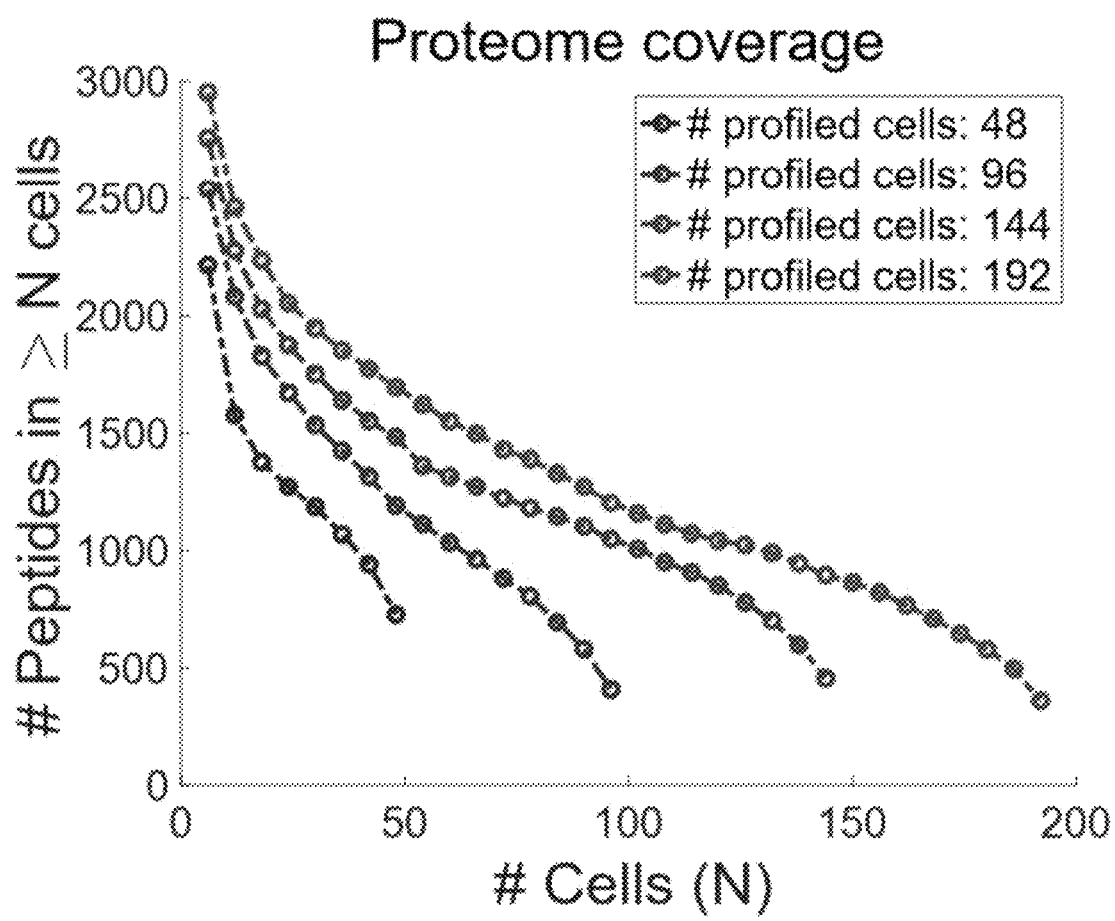

Before applying mPOP to prepare and analyze single-cell proteomes, Applicants sought to estimate the instrument measurement noise in the context of SCoPE-MS sets. This estimate is motivated by the concern that factors unique to ultra-low abundance samples, such as counting noise (Levy, E. & Slavov, N. Single cell protein analysis for systems biology. *Essays In Biochemistry* 62.doi:10.1042/EBC20180014 (4 2018); Specht, H. & Slavov, N. Transformative opportunities for single-cell proteomics. *Journal of Proteome Research* 17, 2563-2916 (8 Jun. 2018)), may undermine measurement accuracy. To isolate the noise in instrument (Q-exactive) measurement from noise due to biological variation and sample preparation, Applicants used mPOP to prepare a 100×M SCoPE-MS sample with two carrier channels (126C—Jurkat cells; 127N—U-937 cells) and 6 interleaved single-cell channels (3 Jurkat and 3 U-937 cells), as shown in FIG. 12A. Thus 1% dilution (1×M) represented the protein abundances expected for single-cell SCoPE-MS set; see FIG. 12A. Although Applicants did not clean the sample, the 1×M dilutions were clean enough to be analyzed by direct injection using a commercial Waters column, and resulted in robust, ion-rich spectra, FIG. 10A. Each 1×M injection was analyzed for only 60 minutes since our goal was to optimize the number of proteins quantified across many cells, rather than the number of proteins quantified per injection (Specht, H. & Slavov, N. Transformative opportunities for single-cell proteomics. *Journal of Proteome Research* 17, 2563-2916 (8 Jun. 2018)). Indeed, Applicants find that the number of peptides quantified across many cells, and thus suitable for biological analysis, increases with the number of analyzed cells, FIG. 10B. The number of confidently identified proteins can be increased up to 50% by applying DART-ID, a data-driven Bayesian framework that uses retention time evidence to enhance peptide sequence identification (Chen, A., Franks, A. & Slavov, N. DART-ID increases single-cell proteome coverage. *bioRxiv*. doi:10.1101/399121 (2018)). Taken together, these results show that mPOP supports the preparation of SCoPE-MS sets from low-input samples.

Figure 10C:
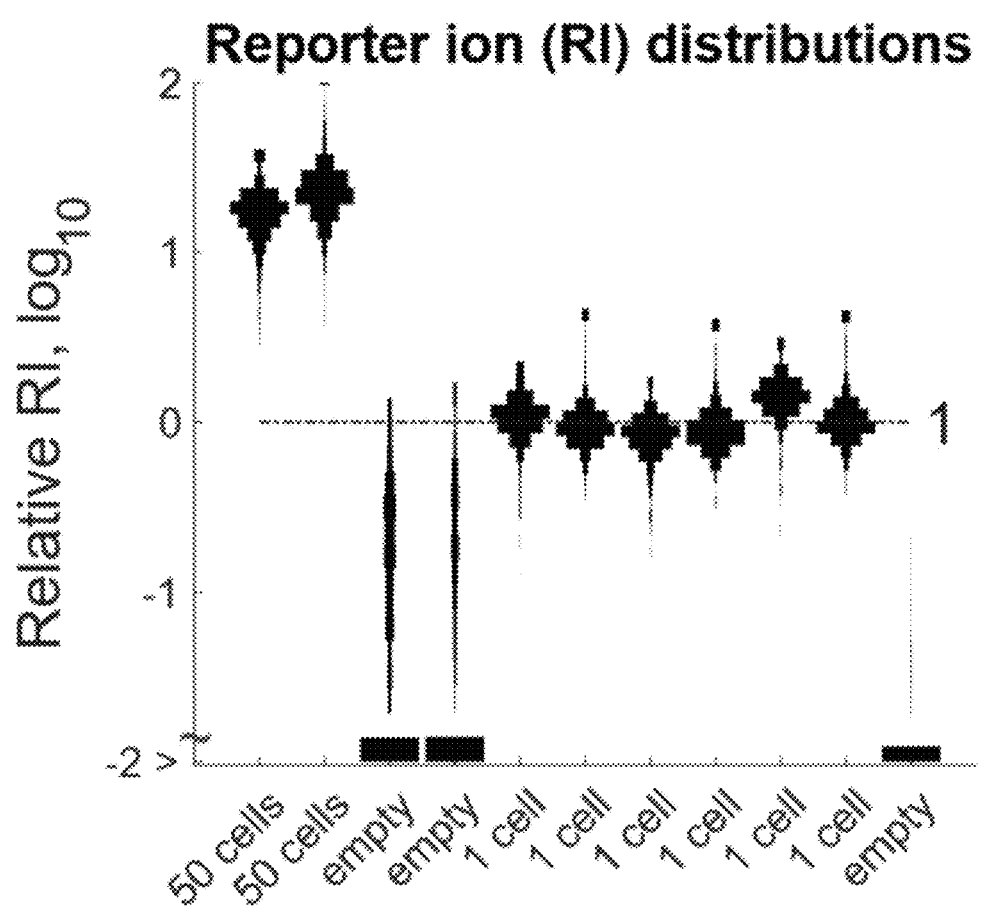
Figure 10D:
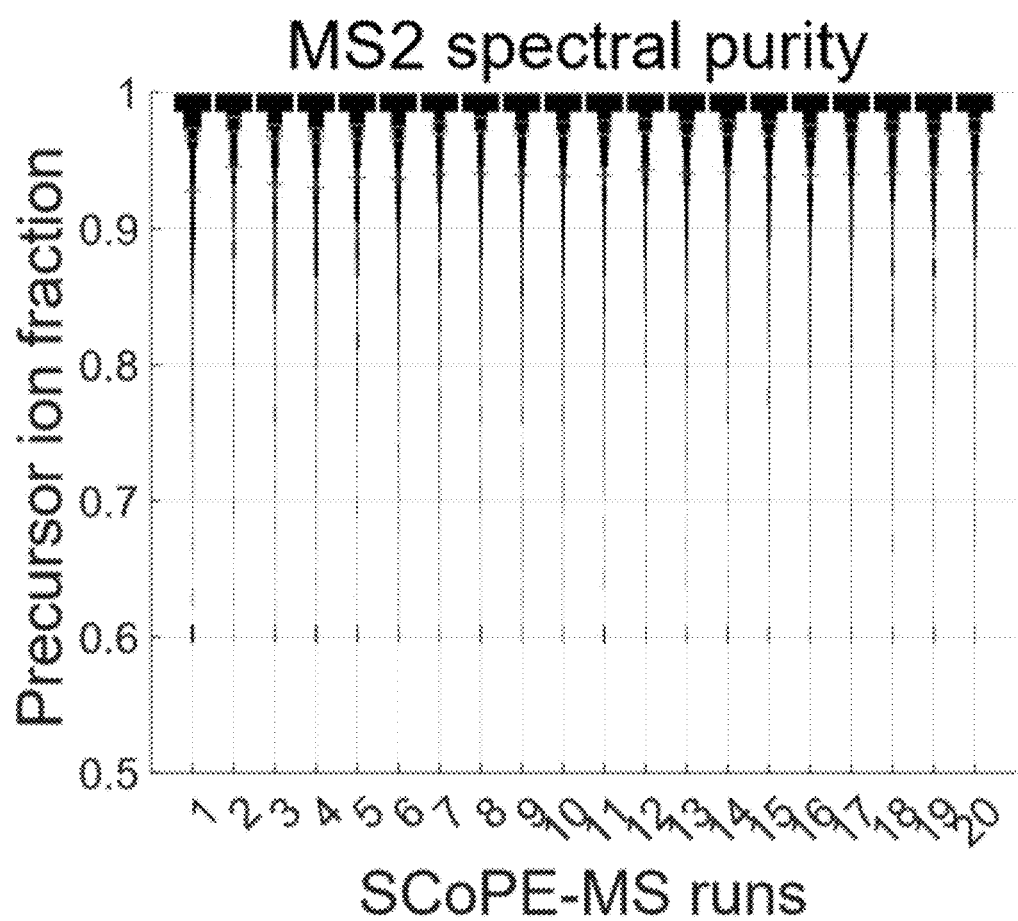
Figure 10E:
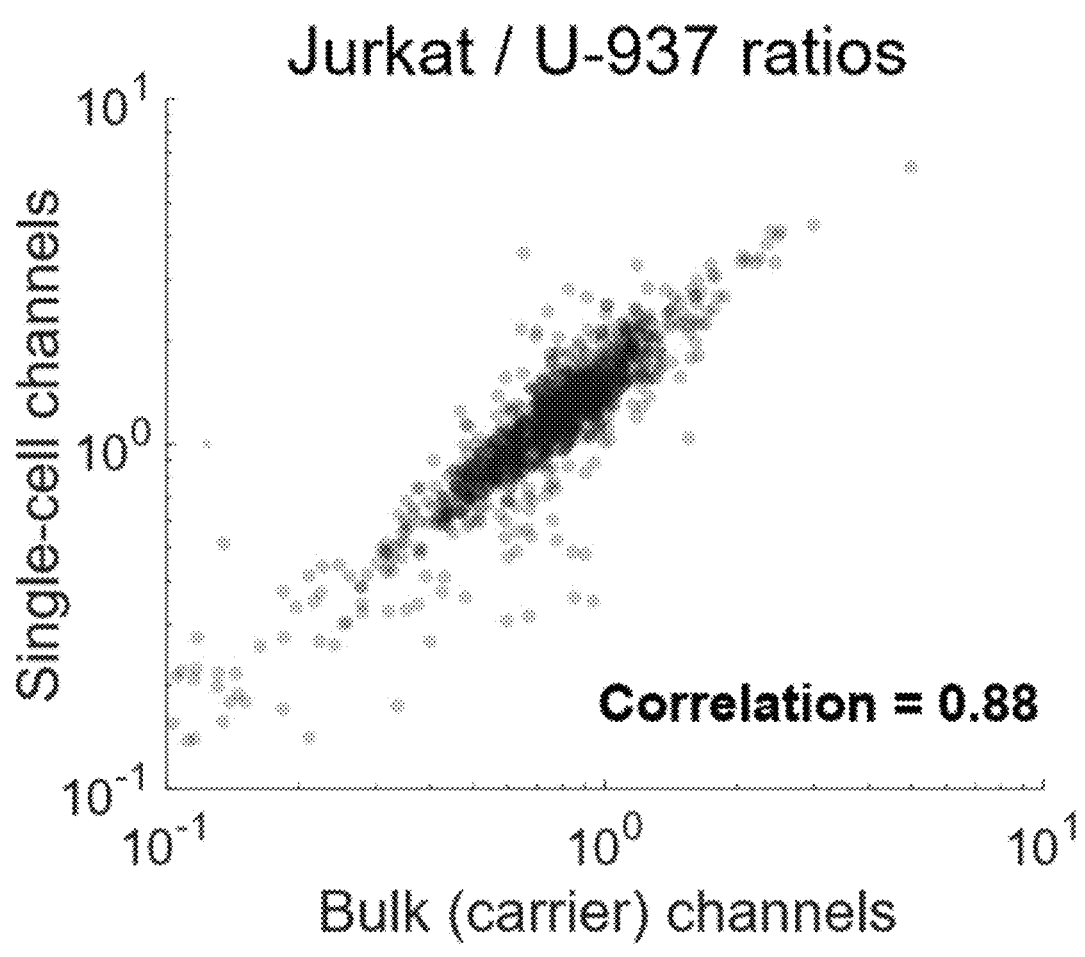
Figure 10F:
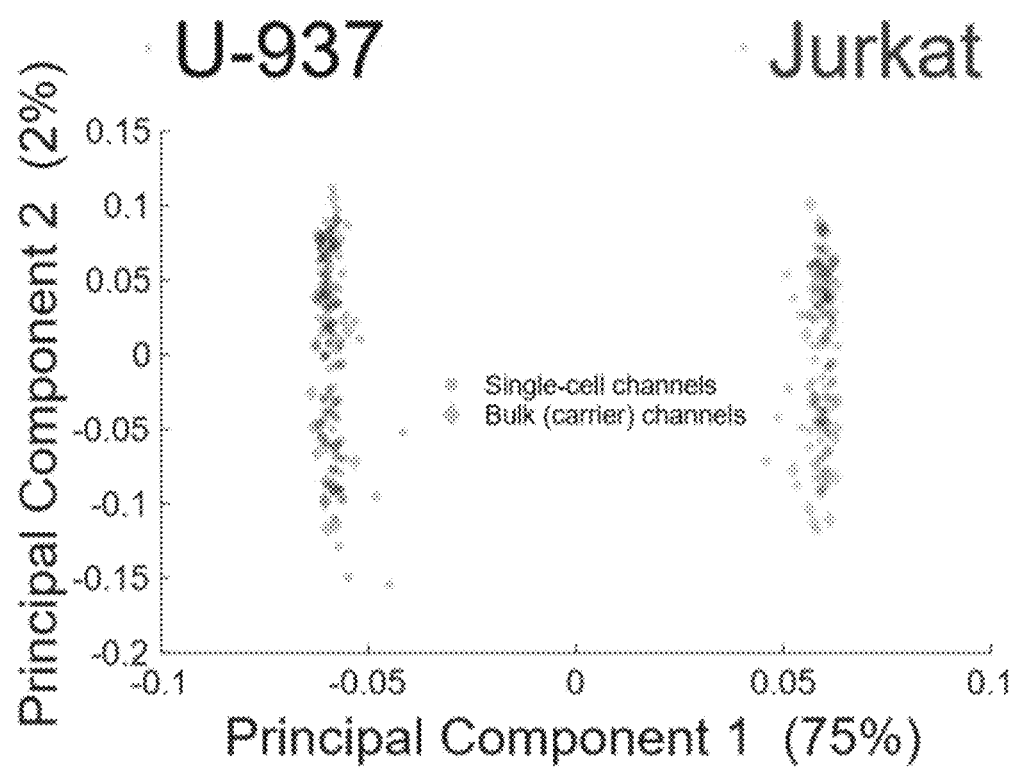

Next, Applicants benchmarked the signal to noise ratio (SNR) and the relative quantification from the single-cell channels in the 1×M samples. To evaluate the SNR, Applicants compared the distributions of relative reporter (RI) ion ratios from single-cell channels and for empty channels (FIG. 10C). Applicants found that the majority of the peptides have orders of magnitude lower signal in the empty channels compared to the single-cell channels, despite the low level of isotopic contamination from the carrier channels (FIG. 10C). This observation and the high purity of the MS2 spectra shown in FIG. 10D suggest that the single-cell Ms contain peptide signal. To evaluate whether this signal is quantitative, Applicants benchmarked the Jurkat/U-937 ratios estimated from single-cell channels against the corresponding ratios estimated from the carrier channels (FIG. 10E). The high concordance of these estimates (Spearman $\rho=0.88$) strongly indicate that the instrument (Q-exactive) noise in quantifying single-cell-level peptides as part of the SCoPE-MS samples is small, consistent with our arguments that the abundance of proteins in mammalian single cells is high-enough to minimize the sampling (counting) noise (Specht, H. & Slavov, N. Transformative opportunities for single-cell proteomics. *Journal of Proteome Research* 17, 2563-2916 (8 Jun. 2018)). To further evaluate relative quantification, beyond the results for a single SCoPE-MS set displayed in FIG. 10E, Applicants consolidated the data from 34 SCoPE-MS sets and computed all pairwise correlations among single-cell and carrier channels. This 272-dimensional matrix was projected just on its first two principal components (PC). When the carrier and single-cell channels are normalized, PCI separates perfectly all channels corresponding to Jurkat or U-937 cells, accounting for the majority of the variance (75%) in the data. Without the normalization, PCI still perfectly separates the measurements by cell type, and PC2 separates the single-cell channels from the carrier channels (see FIG. 12B). Crucially, the single-cell channels separate the same way as the carrier channels, indicating that all single-cell channels were correctly quantified in our work-flow.

EXAMPLE 10

Quantifying Single Cell Proteomes

Figure 11A:
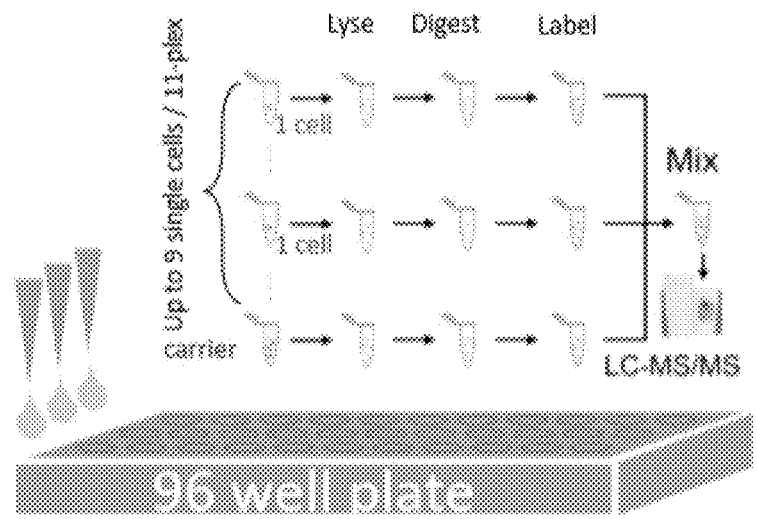
FIGS. 11A-11D provide results of experiments showing that mPOP enables proteomic analysis of cancer cell lines and the mouse embryonic cell cycle from asynchronous single cells.
Figure 11B:
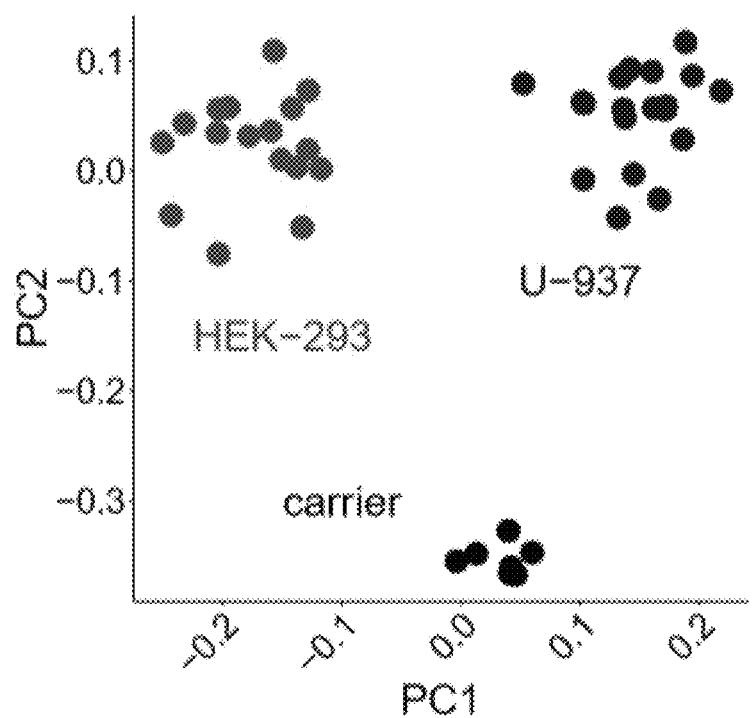
Figure 11C:
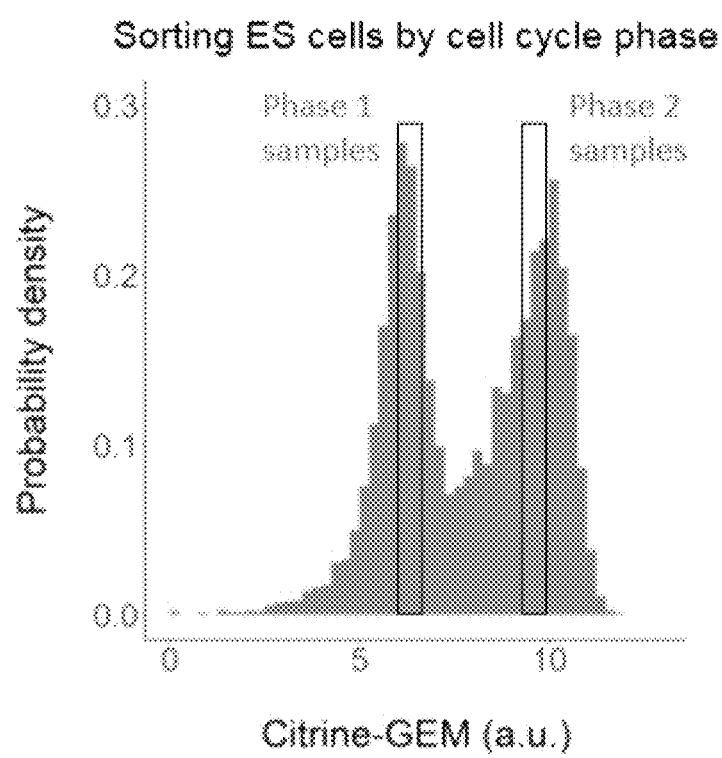
Figure 11D:
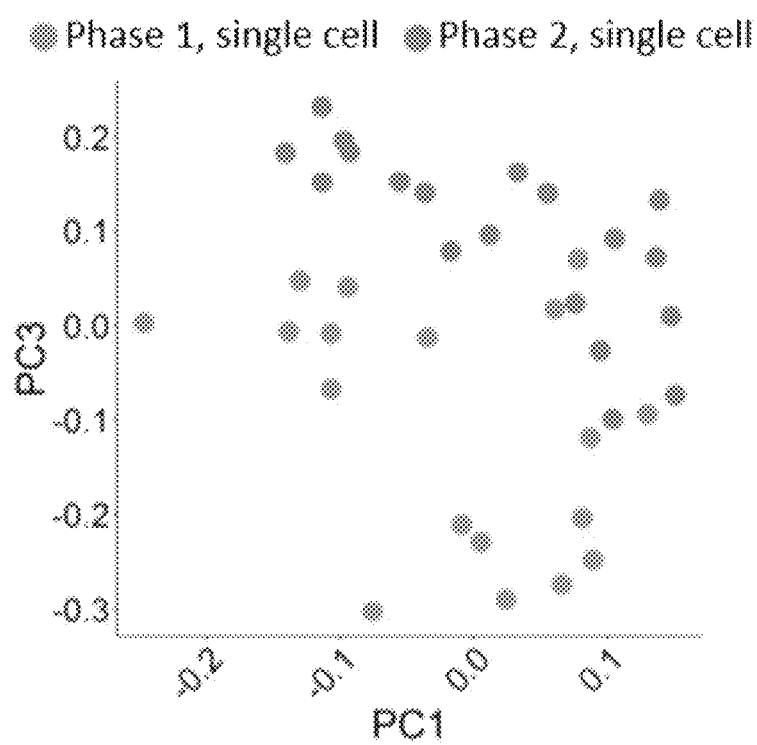

Having demonstrated that 1×M sets can be analyzed with low noise by LC-MS/MS on Q-exactive, Applicants next applied mPOP to the analysis of single cells that were FACS sorted into 96-well plates, one cell per well (FIG. 11A). Unlike the results from FIGS. 10A-10F that characterize just technical variability, this analysis of single cells includes additional variability due to the handing of single cells and due to biological differences between single cells. As a first proof of principle, Applicants again sorted HEK293 and U-937 cells, and found that when processed by mPOP and SCoPE-MS, their proteomes separate along the first principal component of PCA analysis (FIG. 11B). To further test the the ability of mPOP and SCoPE-MS to quantify proteins in single cells, Applicants sorted mouse embryonic stem (ES) cells based on the phase of their cell division cycle (CDC) (FIG. 11C). To this end, Applicants used a fluorescent protein Citrine fused to partial sequences of Geminin that is a ubiquitin-target of the anaphase promoting complex, and thus Citrine is degraded periodically during the CDC (Sladitschek, H. L. & Neveu, P. A. MXS-chaining: a highly efficient cloning platform for imaging and flow cytometry approaches in mammalian systems. *PloS one* 10, e0124958 (2015)). Using this system, known as FUCCI, Applicants sorted ES from the G1 and the G2 phase of the CDC and quantified their proteomes. PCA analysis of the proteins exhibiting the gradient variation across the single cells separated these cells into clusters consistent with the CDC phase determined by the FUCCI system (FIG. 11C). Examining the proteins driving this separation, Applicants found that, consistent with expectations, these proteins are enriched for CDC functions.

Until now, the power of LC-MS/MS proteomics has been circumscribed to samples comprised of many cells. Indeed, the TMT™ manufacturer recommends 100 μg of protein per channel, almost $10^6$ more than the protein content of a typical mammalian cell (Milo R, Jorgensen P, Moran U, Weber G, Springer M. BioNumbers—the database of key numbers in molecular and cell biology. *Nucleic Acids Res.* 2010; 38: D750-3). The methods described herein, e.g., SCoPE-MS, bridged this gap by clean sample preparation and by introducing TMT™-labeled carrier cells. These innovations open the gates to many further improvements (e.g., increased multiplexing) that will make single-cell MS proteomics increasingly powerful (Specht H, Slavov N. Transformative opportunities for single-cell proteomics. *J Proteome Res.* 2018; 17:2563-916).

Answering exciting biological questions demands quantifying proteins in many thousands of single cells, and it is believed that embodiments of the invention described and demonstrated herein will make such throughput practical and affordable (Specht H, Slavov N. Transformative opportunities for single-cell proteomics. *J Proteome Res.* 2018; 17:2563-916). At the moment, the cost per cell is about $15-30, but it can be reduced to $1-2 per cell if Covaris tubes are washed and reused and the MS analysis is done on an in-house MS instrument. It is expected that automation and improvements in sample preparation as well as increased number of tandem mass tags can reduce the cost well below $1 per cell. Also, the fraction of missing data can be substantially reduced by using targeted MS approaches (Specht H, Slavov N. Transformative opportunities for single-cell proteomics. *J Proteome Res.* 2018; 17:2563-916) and by using retention time (RT) evidence to increase the confidence in correct peptide-spectrum matches (Chen A, Franks A, Slavov N. DART-ID increases single-cell proteome coverage. *bioRxiv.* 2018).

The floor of protein detectability and quantification with SCoPE-MS (as well as any other bottom-up MS method) depends not only on the abundance of a protein but also on its sequence, i.e., the number of peptides produced upon digestion and their propensities to be well separated by the chromatography and efficiently ionized by the electrospray. The implementation of SCoPE-MS in this work allowed quantification of mostly abundant proteins present at $\geq 10^5$ copies/cell and only a few proteins present at $\geq 10^4$ copies/cell (those producing the most flyable peptides); see the distribution of abundances of the quantified proteins shown in FIG. 3A. However, the core ideas underpinning SCoPE-MS can extend the sensitivity to most proteins in a mammalian cell, down to proteins present at ~1000 copies/cell. Such extension requires more efficient delivery of proteins to the MS instruments, and specific approaches have been disclosed that can increase the efficiency by orders of magnitude (Specht H, Slavov N. Transformative opportunities for single-cell proteomics. *J Proteome Res.* 2018; 17:2563-916). These approaches include reduced lysis volume and, thus, protein loss (Specht H, Harmange G, Perlman D H, Emmott E, Niziolek Z, Budnik B, Slavov N. Automated sample preparation for high-throughput single-cell proteomics. *bioRxiv.* 2018), and increased sampling of the elution peaks. Such increased sampling is very practical in the context of SCoPE-MS samples analyzed by MS targeting proteins of interest, e.g., transcription factors. Since proteins are substantially more abundant than mRNAs, estimates of their abundance are less likely to be undermined by sampling (counting) noise. Thus, it is believed that based on this disclosure, single-cell MS has the ability to accurately quantify most proteins in single mammalian cells, including lowly abundant ones (Specht H, Slavov N. Transformative opportunities for single-cell proteomics. *J Proteome Res.* 2018; 17:2563-916).

Minimizing sample losses and maximizing throughput is a major requirement for applying ultra-sensitive MS to biological problems (Levy, E. & Slavov, N. Single cell protein analysis for systems biology. *Essays In Biochemistry* 62.doi:10.1042/EBC20180014 (4 2018); Specht, H. & Slavov, N. Transformative opportunities for single-cell proteomics. *Journal of Proteome Research* 17,2563-2916 (8 Jun. 2018)). It has motivated many colleagues to develop sample preparation methods with minimal volumes and low cleanup losses (Zhu, Y. et al. Nanodroplet processing platform for deep and quantitative proteome profiling of 10-100 mammalian cells. *Nature communications* 9,882 (2018); Kulak, N. A., Pichler, G., Paron, I., Nagaraj, N. & Mann, M. Minimal, encapsulated proteomic sample processing applied to copy-number estimation in eukaryotic cells. *Nature methods* 11, 319 (2014)). However, mPOP is the only method that uses solely MS-compatible reagents and allows parallel preparation of hundreds of samples. Crucially, mPOP uses inexpensive equipment accessible to most labs. Furthermore, mPOP allowed us to reduce the sample preparation volume for SCoPE-MS and reduce losses while massively increasing the throughput and the consistency of the data.

Thus, mPOP empowers automated preparation of SCoPE-MS sets at much lower cost than what was possible by focused acoustic sonication. This allows to increase the number of analyzed single cell with affordable resources.

SCoPE-MS enabled the classification of cells and the ability to explore the relationship between mRNA and protein levels in single mammalian cells. This first foray into single mammalian proteomes demonstrates that mRNA covariation is predictive of protein covariation even in single cells. It further establishes the promise of SCoPE-MS to quantitatively characterize single-cell gene regulation and classify cell types based on their proteomes.

The relevant teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of identifying and quantifying labeled test peptides in a test sample comprising a single cell, the method comprising:
    mechanically lysing the test sample to obtain a cell lysate;
    digesting proteins released from the cell lysate to obtain test peptides;
    labeling the test peptides to produce labeled test peptides;
    mixing the labeled test peptides from the test sample with labeled carrier peptides from a carrier sample to form a mixture, wherein the carrier sample is obtained from at least about 10-fold more cells than the test sample, and wherein the labeled test peptides and the labeled carrier peptides have different labels; and
    performing liquid chromatography and tandem mass spectroscopy (LC-MS/MS) on the mixture to obtain an analysis of the labeled test peptides,
    thereby identifying and quantifying the labeled test peptides.

2. The method of claim 1, wherein the carrier sample is obtained from the same type of cell as the test sample.

3. The method of claim 1, wherein the carrier sample is obtained from 100 or more cells.

4. The method of claim 1, wherein the analysis comprises obtaining a relative quantification of labeled test peptides.

5. The method of claim 1, wherein the analysis comprises sequencing of the labeled test peptides.

6. The method of claim 1, wherein mechanically lysing the test sample comprises freezing the test sample to about −80 degrees Celsius and then heating the test sample to about 90 degrees Celsius.

7. The method of claim 1, wherein the test peptides and the carrier peptides are labeled with different isobaric tags.

8. The method of claim 1, wherein the single cell is a single mammalian cell.

9. A method of identifying and quantifying labeled post-translationally modified test peptides in a test sample comprising a single cell, the method comprising:
    mechanically lysing the test sample to obtain a lysate;
    digesting proteins released from the lysate to obtain post-translationally modified test peptides;
    labeling the post-translationally modified test peptides to produce labeled post- translationally modified test peptides;
    mixing labeled post-translationally modified test peptides from the test sample with labeled post-translationally modified carrier peptides from a carrier sample to form a mixture, wherein the carrier sample is obtained from at least about 10-fold more cells than the test sample, and wherein the labeled post-translationally modified test peptides and the labeled post-translationally modified carrier peptides have different labels; and performing liquid chromatography and tandem mass spectroscopy (LC-MS/MS) on the mixture to obtain an analysis of the labeled post-translationally modified test peptides, thereby identifying and quantifying the labeled post-translationally modified test peptides.

10. The method of claim 9, wherein the carrier sample is obtained from the same type of cell as the test sample.

11. The method of claim 9, wherein the carrier sample is obtained from 100 or more cells.

12. The method of claim 9, wherein the analysis comprises obtaining a relative quantification of labeled post-translationally modified test peptides.

13. The method of claim 9, wherein the analysis comprises sequencing of labeled post-translationally modified test peptides.

14. The method of claim 9, wherein the post-translational modification is selected from the group consisting of phosphorylation, acetylation, ubiquitination, O-glycosylation, N-glycosylation, sumoylation, methylation and combinations thereof.

15. The method of claim 9, wherein the post-translationally modified test peptides and the carrier peptides are labeled with different isobaric tags.

16. The method of claim 9, wherein the single cell is a single mammalian cell.

17. The method of claim 9, wherein mechanically lysing the test sample comprises freezing the test sample to about −80 degrees Celsius and then heating the test sample to about 90 degrees Celsius.

* * * * *